United States Patent
Baker et al.

(10) Patent No.: US 11,975,018 B2
(45) Date of Patent: *May 7, 2024

(54) METHODS FOR TREATMENT OR PREVENTION OF DAMAGE RESULTING FROM RADIATION, TRAUMA OR SHOCK

(71) Applicant: SYNEDGEN, INC., Claremont, CA (US)

(72) Inventors: Shenda M. Baker, Upland, CA (US); William P. Wiesmann, Chevy Chase, MD (US)

(73) Assignee: SYNEDGEN, INC., Claremont, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 17/150,406

(22) Filed: Jan. 15, 2021

(65) Prior Publication Data

US 2021/0386774 A1 Dec. 16, 2021

Related U.S. Application Data

(63) Continuation of application No. 16/896,562, filed on Jun. 9, 2020, now abandoned, which is a continuation of application No. 16/007,503, filed on Jun. 13, 2018, now Pat. No. 10,716,803, which is a continuation of application No. 14/033,332, filed on Sep. 20, 2013, now Pat. No. 10,022,393.

(60) Provisional application No. 61/737,576, filed on Dec. 14, 2012, provisional application No. 61/703,703, filed on Sep. 20, 2012.

(51) Int. Cl.
*A61K 31/726* (2006.01)

(52) U.S. Cl.
CPC ............. *A61K 31/726* (2013.01); *Y02A 50/30* (2018.01)

(58) Field of Classification Search
CPC ........ A61K 31/726; A61P 17/02; A61P 29/00; A61P 31/00
USPC ...................................................... 514/54, 55
See application file for complete search history.

(56) References Cited

U.S. PATENT DOCUMENTS

| | | | |
|---|---|---|---|
| 4,409,205 A | 10/1983 | Shively | |
| 5,610,184 A | 3/1997 | Shahinian, Jr. | |
| 6,323,189 B1 | 11/2001 | Hardinge-Lyme | |
| 10,022,393 B2 * | 7/2018 | Baker | A61P 17/02 |
| 10,716,803 B2 * | 7/2020 | Baker | A61P 31/00 |
| 2009/0202430 A1 | 8/2009 | Hoemann et al. | |
| 2011/0206654 A1 | 8/2011 | Hodin et al. | |
| 2011/0263504 A1 * | 10/2011 | Cerami | A61P 9/00 435/320.1 |
| 2013/0164311 A1 | 6/2013 | DeCarlo et al. | |
| 2013/0210761 A1 | 8/2013 | Baker et al. | |

FOREIGN PATENT DOCUMENTS

| | | | |
|---|---|---|---|
| CN | 1965650 A | 5/2007 | |
| KR | 20180025649 A | 3/2018 | |
| WO | 00/30609 A1 | 6/2000 | |
| WO | 2007/142704 A3 | 5/2008 | |
| WO | WO 2011/127144 A1 * | 10/2011 | A61K 9/66 |
| WO | 2016/040899 A1 | 3/2016 | |
| WO | 2018202783 A1 | 11/2018 | |

OTHER PUBLICATIONS

Thuijls et al., Netherlands Journal of Critical Care, 2011, 15(4), 199-203.*
Mitsuyama K, et al. "Interleukin-10 in the Pathophysiology of Inflammatory Bowel Disease: Increased Serum Concentrations During the Recovery Phase," Mediators of inflammation (2006) Article ID 26875, pp. 1-7.
Lin W, et al. "Effects of crab shell's chitosan administration on cytokine secretion by lipopolysaccharide-stimulated splenocytes from BALB/c mice," Taiwan Nongye Huaxue Yu Shipin Kexue (2009), vol. 47, No. 3, pp. 119-125 (abstract).
Burns et al. (Docum. Ophthal. Proc. Series, vol. 18, 245-251; Hockwin et al. (eds.), Progress in Anterior Eye Segment Research and Practice © Dr W. Junk b.v. Publishers 1979).
Junping Li, et al. "Drug-Induced Ocular Disorders", Drug Safety 2008; 31 (2); p. 127-141.
Wolfgang Bernauer, Ocular surface problems following topial medication, Klin Monatsbl Augenheilkd 2002; 219: 240-242.
International Search Report and Written Opinion for corresponding International Application No. PCT/US2017/22698 dated Jun. 9, 2017.
Extended European Search Report for EP17767522 dated Aug. 26, 2019 (4 pages).
Tang, H et al., "Antibacterial action of a novel functionalized chitosan-arginine against Gram-negative bacteria" Acta Biomaterialia 2010, vol. 6, Issue 7, pp. 2562-2571.
Pfister et al., "Topical ascorbate decreases the incidence of corneal ulceration after experimental al-kali burns", Investigative Ophthalmology & Visual Science (1978), 17( 10), 1019-24.
Pharmaceutical Solutions for Oral Administration (Chapter 1, pp. 1-24; 2008).

* cited by examiner

*Primary Examiner* — Ganapathy Krishnan
(74) *Attorney, Agent, or Firm* — Goodwin Procter LLP

(57) ABSTRACT

Described herein are methods of treating a subject that has been or will be exposed to radiation, trauma or shock, the method comprising identifying a subject that has been or will be exposed to radiation, and treating the subject with a compound that treats, reduces the severity or delays the onset of sepsis or reduces the likelihood of mortality in a subject upon administration of a therapeutically effective amount the compound to the subject.

19 Claims, 30 Drawing Sheets

METHODS FOR TREATMENT OR PREVENTION OF DAMAGE RESULTING FROM RADIATION, TRAUMA OR SHOCK

CLAIMS OF PRIORITY

This application is a continuation of U.S. Ser. No. 16/896,562 filed on Jun. 9, 2020, which is a continuation of U.S. Ser. No. 16/007,503 filed on Jun. 13, 2018, which is a continuation of U.S. Ser. No. 14/033,332 filed on Sep. 20, 2013, which claims priority to U.S. Ser. No. 61/703, 703, filed Sep. 20, 2012 and U.S. Ser. No. 61/737,576, filed Dec. 14, 2012, the entire contents of which are incorporated herein by reference.

FIELD OF THE INVENTION

The invention relates to the use of polyglucosamines to treat or prevent damage resulting from radiation, trauma or shock.

BACKGROUND

Environmental or physical stresses and stimuli, for example, from radiation, trauma or shock, can result in biological damage or otherwise trigger a series of intricate biological events that can increase the morbidity and mortality rate in a subject.

SUMMARY OF THE INVENTION

Methods of treating a subject that has been or will be exposed to radiation, trauma or shock are described herein. Exemplary methods described herein include, for example, methods of treating a subject that has been exposed to radiation, trauma or shock with a compound that reduces sepsis or mortality; methods of reducing the severity of sepsis or a symptom thereof or decreasing the likelihood of mortality of a subject that has been or will be exposed to radiation, trauma or shock.

In an aspect, the invention features a method of treating a subject, the method comprising identifying a subject that has been exposed to radiation, trauma or shock, and treating the identified subject by administering to the identified subject a therapeutically effective amount of a compound to the subject, wherein the compound is a compound of Formula (I):

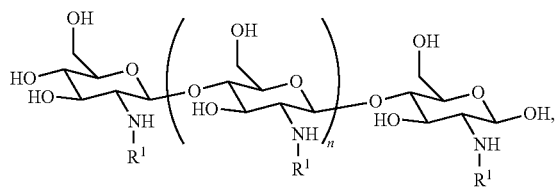

Formula (I)

wherein n is an integer between 20 and 6000; and each $R^1$ is independently selected for each occurrence from hydrogen, acetyl,

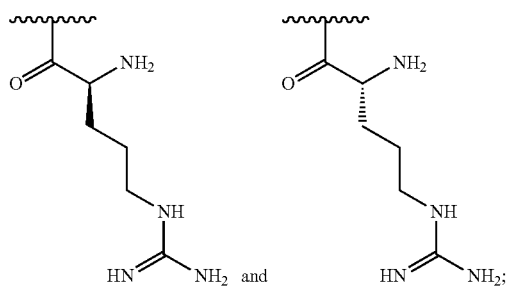 [SMILES: *C(=O)[C@@H](N)CCCNC(=N)N ; *C(=O)[C@H](N)CCCNC(=N)N]

wherein at least 25% of $R^1$ substituents are H, at least 1% of $R^1$ substituents are acetyl, and at least 2% of $R^1$ substituents are

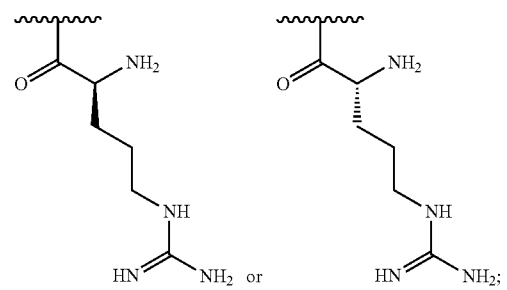 [SMILES: *C(=O)[C@@H](N)CCCNC(=N)N ; *C(=O)[C@H](N)CCCNC(=N)N]

wherein upon administration of the compound, the compound treats, reduces the severity or delays the onset of sepsis or reduces the likelihood of mortality in the subject, thereby treating the subject.

In some embodiments, the subject has a bacterial infection, chemical damage or radiation damage, e.g., resulting in leaky gut and/or damage to the GI tract. In some embodiments, the infection or damage results in leaky gut.

In some embodiments, the method reduces the severity of sepsis or a symptom thereof or decreases the likelihood of mortality from the radiation, trauma or shock relative to a subject not administered with the compound.

In some embodiments, the subject has sepsis or a symptom of sepsis resulting from radiation, trauma or shock. In some embodiments, the sepsis is caused by leaky gut (e.g., mucosal lesions). In some embodiments, the subject is at risk of developing sepsis as a result of exposure to radiation, trauma or shock.

In some embodiments, the radiation, trauma or shock results in reduced integrity of the GI tract of the subject or leaky gut (e.g., mucosal lesions in the GI tract) in a subject.

In some embodiments, the trauma or shock is a bacterial, viral, or fungal infection resulting in GI damage. In some embodiments, the bacterial infection is from one of the following bacteria: *Salmonella enterica* serovar *Typhimurium*, *Shigella flexneri*, *E. coli* and *P. aeruginosa*.

In some embodiments, the subject has been exposed to radiation in an amount sufficient to produce 30% to 80% lethality, e.g., at 30% to 80% lethal dose, at LD30 to LD80.

In some embodiments, the method reduces inflammation in the subject from the radiation, trauma or shock. In some embodiments, the method mitigates the inflammatory response in the GI tract. In some embodiments, the method mitigates the inflammatory response and reduces mortality due to bacterial infection, bacterial translocation or chemical damage or radiation damage in the GI tract of a subject relative to a subject not administered with the compound.

In some embodiments, the method protects epithelial cells from bacterial invasion. In some embodiments, the method reduces translocation of bacteria across the GI tract, e.g., by up to 80%. In some embodiments, the compound acts through mucoadhesive substantivity (e.g., adhesion, affinity). In some embodiments, the method reduces crypt degeneration. In some embodiments, the method promotes the health of villous epithelium (e.g. reduces loss or blunting of villi).

In some embodiments, the method reduces mortality after exposure of the GI tract of a subject to ionizing radiation relative to a subject not administered with the compound. In some embodiments, the radiation is from a dirty bomb, accidental nuclear incident or therapeutic radiation not related to the treatment of cancer. In some embodiments, the radiation is targeted to therapeutic treatment requiring destruction of the immune system, e.g., bone marrow transplant therapy or other elective exposure to radiation.

In some embodiments, the trauma results from exposure to a toxic chemical or poison. In some embodiments, the toxic chemical or poison is ingested.

In some embodiments, the trauma results from multi-organ failure from physical damage and trauma to the body, burns, blast injury, systemic infection, blood loss (hypotension), and traumatic brain injury.

In some embodiments, the shock is physical shock not resulting in a wound. In some embodiments, the shock results from excessive stimuli, e.g. pathogens, commensals, injury, heat, autoantigens, tumors, necrotic cells. In some embodiments, the trauma results from a commensal or a pathogen translocating to an organ or tissue that is usually free of bacteria (e.g., an organ or tissue that is free of bacteria in the absence of trauma).

In some embodiments, the subject has or is at risk of hypotension and/or reduced blood pressure as a physical manifestation of radiation, trauma or shock.

In some embodiments, the subject has suffered reperfusion injury, e.g., treated to restore blood circulation.

In some embodiments, the subject has or is at risk of having reduced nutrient absorption, pain, nausea, diarrhea, and/or weight loss resulting from radiation, trauma or shock.

In some embodiments, the subject has necrotizing enterocolitis, necrotic enteritis, short bowel syndrome or short gut syndrome.

In some embodiments, the method returns the GI tract to normal homeostasis. In some embodiments, the method improves absorption of nutrients from the GI tract.

In some embodiments, the method reduces traumatic insult.

In some embodiments, the method reduces overstimulation of the immune system. In some embodiments, the method regulates the initiation of regenerative pathways.

In some embodiments, the method promotes survival. In some embodiments, the method improves mortality.

In some embodiments, the method reduces damage to the GI tract. In some embodiments, the method improves healing of the epithelia and or the villi in the GI tract. In some embodiments, the method returns the GI tract to normal homeostasis. In some embodiments, the method reduces bacterial translocation across the GI tract. In some embodiments, the method improves absorption of nutrients from the GI tract.

In some embodiments, the method reduces local inflammation. In some embodiments, the method reduces systemic inflammation.

In some embodiments, the method reduces pain and suffering in the subject.

In some embodiments, the compound is administered at regular intervals. In some embodiments, the compound is administered periodically at regular intervals (e.g., 1, 2, 3, 4, 5, 6, 7, 8, 9, 10 or more times every 1, 2, 3, 4, 5, or 6 days).

In some embodiments, the compound is administered at a predetermined interval (e.g., 1, 2, 3, 4, 5, 6, 7, 8, 9, 10 or more times every 1, 2, 3, 4, 5, or 6 days). In some embodiments, the compound is administered once daily. In some embodiments, the compound is administered from about 1 to about 5 times per day. In some embodiments, the compound is administered from about 1 to about 3 times per day.

In some embodiments, the subject is treated for up to 3 weeks, 2 weeks, 1 week, 6 days, 5 days, 4 days, 3 days, 2 days, or 1 day.

In some embodiments, the subject is treated for 3 weeks, 2 weeks, 1 week, 6 days, 5 days, 4 days, 3 days, 2 days, or 1 day.

In some embodiments, the subject is treated within 1 hour, 2 hours, 3 hours, 4 hours, 5 hours, 6 hours, 8 hours, 10 hours, 12 hours, 16 hours, 20 hours, 24 hours, 2 days, 3 days, 4 days, 5 days, 6 days, 1 week, or 2 weeks after exposure to radiation, trauma, shock, or infection (e.g., bacterial or viral infection).

In some embodiments, the derivatized chitosan is functionalized at between 18% and 30%.

In some embodiments, the molecular weight of the derivatized chitosan is from 50 to 150 kDa (e.g., between 50 and 125 kDa, e.g., between 60 to 100 kDa, e.g., about 90 kDa).

In some embodiments, the polydispersity index of the derivatized chitosan is from 1.0 to 2.5. In some embodiments, the polydispersity index of the derivatized chitosan is from 1.5 to 2.0.

In one aspect, the invention features a method of treating a subject, the method comprising identifying a subject that will be exposed to radiation, trauma or shock; and prior to exposure to radiation, trauma or shock, treating the subject by administering a therapeutically effective amount of a compound to the subject, wherein the compound is a compound of Formula (I):

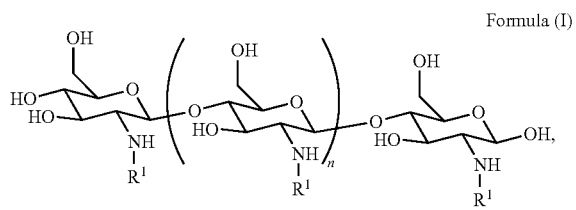

Formula (I)

wherein n is an integer between 20 and 6000; and each $R^1$ is independently selected for each occurrence from hydrogen, acetyl,

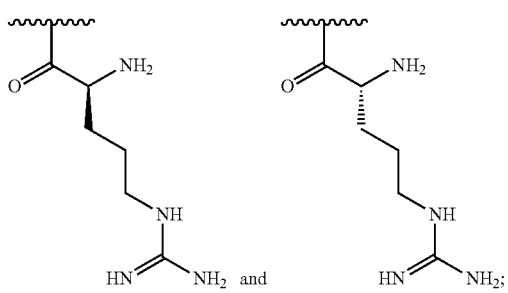 [SMILES: *C(=O)[C@@H](N)CCCNC(=N)N ; *C(=O)[C@H](N)CCCNC(=N)N]

wherein at least 25% of $R^1$ substituents are H, at least 1% of $R^1$ substituents are acetyl, and at least 2% of $R^1$ substituents are

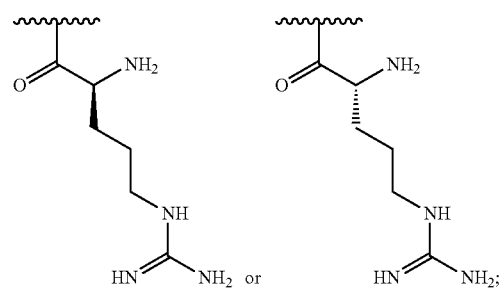

wherein upon administration of the compound, the compound treats, reduces the severity or delays the onset of sepsis or reduces the likelihood of mortality, thereby prophylactically treating the subject.

In some embodiments, the permeability is a result of shock, trauma, or exposure to infection in the GI.

In some embodiments, the subject has a bacterial infection, chemical damage or radiation damage, e.g., resulting in leaky gut and/or damage to the GI tract. In some embodiments, the infection or damage results in leaky gut.

In some embodiments, the method reduces the severity of sepsis or a symptom thereof or decreases the likelihood of mortality from the radiation, trauma or shock relative to a subject not administered with the compound.

In some embodiments, the subject has sepsis or a symptom of sepsis resulting from radiation, trauma or shock. In some embodiments, the sepsis is caused by leaky gut (e.g., mucosal lesions). In some embodiments, the subject is at risk of developing sepsis as a result of exposure to radiation, trauma or shock.

In some embodiments, the radiation, trauma or shock results in reduced integrity of the GI tract of the subject or leaky gut (e.g., mucosal lesions in the GI tract) in a subject.

In some embodiments, the trauma or shock is a bacterial, viral, or fungal infection resulting in GI damage. In some embodiments, the bacterial infection is from one of the following bacteria: *Salmonella enterica* serovar *Typhimurium, Shigella flexneri, E. coli* and *P. aeruginosa*.

In some embodiments, the subject has been exposed to radiation in an amount sufficient to produce 30% to 80% lethality, e.g., at 30% to 80% lethal dose, at LD30 to LIMO.

In some embodiments, the method reduces inflammation in the subject from the radiation, trauma or shock. In some embodiments, the method mitigates the inflammatory response in the GI tract. In some embodiments, the method mitigates the inflammatory response and reduces mortality due to bacterial infection, bacterial translocation or chemical damage or radiation damage in the GI tract of a subject relative to a subject not administered with the compound.

In some embodiments, the method protects epithelial cells from bacterial invasion. In some embodiments, the method reduces translocation of bacteria across the GI tract, e.g., by up to 80%. In some embodiments, the compound acts through mucoadhesive substantivity (e.g., adhesion, affinity). In some embodiments, the method reduces crypt degeneration. In some embodiments, the method promotes the health of villous epithelium (e.g. reduces loss or blunting of villi).

In some embodiments, the method reduces mortality after exposure of the GI tract of a subject to ionizing radiation relative to a subject not administered with the compound. In some embodiments, the radiation is from a dirty bomb, accidental nuclear incident or therapeutic radiation not related to the treatment of cancer. In some embodiments, the radiation is targeted to therapeutic treatment requiring destruction of the immune system, e.g., bone marrow transplant therapy or other elective exposure to radiation.

In some embodiments, the trauma results from exposure to a toxic chemical or poison. In some embodiments, the toxic chemical or poison is ingested.

In some embodiments, the trauma results from multi-organ failure from physical damage and trauma to the body, burns, blast injury, systemic infection, blood loss (hypotension), and traumatic brain injury.

In some embodiments, the shock is physical shock not resulting in a wound. In some embodiments, the shock results from excessive stimuli, e.g. pathogens, commensals, injury, heat, autoantigens, tumors, necrotic cells. In some embodiments, the trauma results from a commensal or a pathogen translocating to an organ or tissue that is usually free of bacteria (e.g., an organ or tissue that is free of bacteria in the absence of trauma).

In some embodiments, the subject has or is at risk of hypotension and/or reduced blood pressure as a physical manifestation of radiation, trauma or shock.

In some embodiments, the subject has suffered reperfusion injury, e.g., treated to restore blood circulation.

In some embodiments, the subject has or is at risk of having reduced nutrient absorption, pain, nausea, diarrhea, and/or weight loss resulting from radiation, trauma or shock.

In some embodiments, the subject has necrotizing enterocolitis, necrotic enteritis, short bowel syndrome or short gut syndrome.

In some embodiments, the method returns the GI tract to normal homeostasis. In some embodiments, the method improves absorption of nutrients from the GI tract.

In some embodiments, the method reduces traumatic insult.

In some embodiments, the method reduces overstimulation of the immune system. In some embodiments, the method regulates the initiation of regenerative pathways.

In some embodiments, the method promotes survival. In some embodiments, the method improves mortality.

In some embodiments, the method reduces damage to the GI tract. In some embodiments, the method improves healing of the epithelia and or the villi in the GI tract. In some embodiments, the method returns the GI tract to normal homeostasis. In some embodiments, the method reduces bacterial translocation across the GI tract. In some embodiments, the method improves absorption of nutrients from the GI tract.

In some embodiments, the method reduces local inflammation. In some embodiments, the method reduces systemic inflammation.

In some embodiments, the method reduces pain and suffering in the subject.

In some embodiments, the compound is administered at regular intervals. In some embodiments, the compound is administered periodically at regular intervals (e.g., 1, 2, 3, 4, 5, 6, 7, 8, 9, 10 or more times every 1, 2, 3, 4, 5, or 6 days).

In some embodiments, the compound is administered at a predetermined interval (e.g., 1, 2, 3, 4, 5, 6, 7, 8, 9, 10 or more times every 1, 2, 3, 4, 5, or 6 days). In some embodiments, the compound is administered once daily. In some embodiments, the compound is administered from about 1 to about 5 times per day. In some embodiments, the compound is administered from about 1 to about 3 times per day.

In some embodiments, the subject is treated for up to 3 weeks, 2 weeks, 1 week, 6 days, 5 days, 4 days, 3 days, 2 days, or 1 day.

In some embodiments, the subject is treated for 3 weeks, 2 weeks, 1 week, 6 days, 5 days, 4 days, 3 days, 2 days, or 1 day.

In some embodiments, the subject is treated within 1 hour, 2 hours, 3 hours, 4 hours, 5 hours, 6 hours, 8 hours, 10 hours, 12 hours, 16 hours, 20 hours, 24 hours, 2 days, 3 days, 4 days, 5 days, 6 days, 1 week, or 2 weeks after exposure to radiation, trauma, shock, or infection (e.g., bacterial or viral infection).

In some embodiments, the derivatized chitosan is functionalized at between 18% and 30%.

In some embodiments, the molecular weight of the derivatized chitosan is from 50 to 150 kDa (e.g., between 50 and 125 kDa, e.g., between 60 to 100 kDa, e.g., about 90 kDa).

In some embodiments, the polydispersity index of the derivatized chitosan is from 1.0 to 2.5. In some embodiments, the polydispersity index of the derivatized chitosan is from 1.5 to 2.0.

In one aspect, the invention features a method of reducing permeability (e.g., tissue damage) of the gastrointestinal tract of a subject, the method comprising identifying a subject that has been exposed to radiation, trauma or shock, and treating the subject by administering a therapeutically effective amount of a compound to the subject, wherein the compound is a compound of Formula (I):

Formula (I)

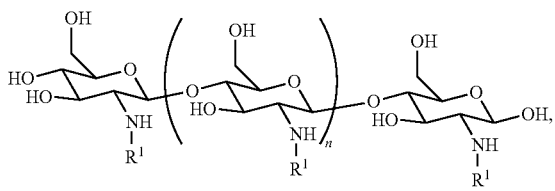

wherein n is an integer between 20 and 6000; and each $R^1$ is independently selected for each occurrence from hydrogen, acetyl,

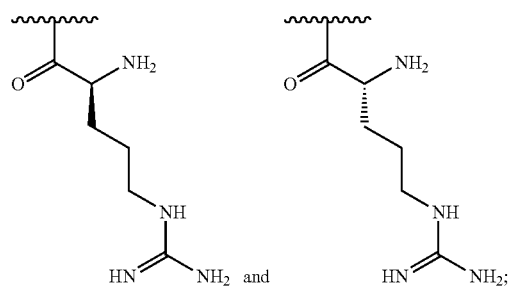 [SMILES: *C(=O)[C@@H](N)CCCNC(=N)N ; *C(=O)[C@H](N)CCCNC(=N)N]

wherein at least 25% of $R^1$ substituents are H, at least 1% of $R^1$ substituents are acetyl, and at least 2% of $R^1$ substituents are

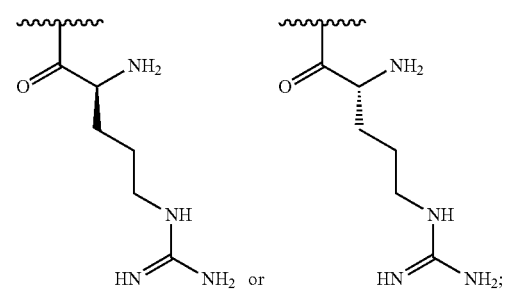 [SMILES: *C(=O)[C@@H](N)CCCNC(=N)N ; *C(=O)[C@H](N)CCCNC(=N)N]

wherein upon administration of the compound, the compound reduces permeability of the gastrointestinal tract of a subject, thereby treating the subject.

In some embodiments, the permeability is a result of shock, trauma, or exposure to infection in the GI.

In some embodiments, the subject has a bacterial infection, chemical damage or radiation damage, e.g., resulting in leaky gut and/or damage to the GI tract. In some embodiments, the infection or damage results in leaky gut.

In some embodiments, the method reduces the severity of sepsis or a symptom thereof or decreases the likelihood of mortality from the radiation, trauma or shock relative to a subject not administered with the compound.

In some embodiments, the subject has sepsis or a symptom of sepsis resulting from radiation, trauma or shock. In some embodiments, the sepsis is caused by leaky gut (e.g., mucosal lesions). In some embodiments, the subject is at risk of developing sepsis as a result of exposure to radiation, trauma or shock.

In some embodiments, the radiation, trauma or shock results in reduced integrity of the GI tract of the subject or leaky gut (e.g., mucosal lesions in the GI tract) in a subject.

In some embodiments, the trauma or shock is a bacterial, viral, or fungal infection resulting in GI damage. In some embodiments, the bacterial infection is from one of the following bacteria: *Salmonella enterica* serovar *Typhimurium*, *Shigella flexneri*, *E. coli* and *P. aeruginosa*.

In some embodiments, the subject has been exposed to radiation in an amount sufficient to produce 30% to 80% lethality, e.g., at 30% to 80% lethal dose, at LD30 to LD80.

In some embodiments, the method reduces inflammation in the subject from the radiation, trauma, or shock. In some embodiments, the method mitigates the inflammatory response in the GI tract. In some embodiments, the method mitigates the inflammatory response and reduces mortality due to bacterial infection, bacterial translocation or chemical damage or radiation damage in the GI tract of a subject relative to a subject not administered with the compound.

In some embodiments, the method protects epithelial cells from bacterial invasion. In some embodiments, the method reduces translocation of bacteria across the GI tract, e.g., by up to 80%. In some embodiments, the compound acts through mucoadhesive substantivity (e.g., adhesion, affinity). In some embodiments, the method reduces crypt degeneration. In some embodiments, the method promotes the health of villous epithelium (e.g. reduces loss or blunting of villi).

In some embodiments, the method reduces mortality after exposure of the GI tract of a subject to ionizing radiation relative to a subject not administered with the compound. In some embodiments, the radiation is from a dirty bomb, accidental nuclear incident or therapeutic radiation not related to the treatment of cancer. In some embodiments, the radiation is targeted to therapeutic treatment requiring destruction of the immune system, e.g., bone marrow transplant therapy or other elective exposure to radiation.

In some embodiments, the trauma results from exposure to a toxic chemical or poison. In some embodiments, the toxic chemical or poison is ingested.

In some embodiments, the trauma results from multiorgan failure from physical damage and trauma to the body, burns, blast injury, systemic infection, blood loss (hypotension), and traumatic brain injury.

In some embodiments, the shock is physical shock not resulting in a wound. In some embodiments, the shock results from excessive stimuli, e.g. pathogens, commensals, injury, heat, autoantigens, tumors, necrotic cells. In some embodiments, the trauma results from a commensal or a pathogen translocating to an organ or tissue that is usually free of bacteria (e.g., an organ or tissue that is free of bacteria in the absence of trauma).

In some embodiments, the subject has or is at risk of hypotension and/or reduced blood pressure as a physical manifestation of radiation, trauma or shock.

In some embodiments, the subject has suffered reperfusion injury, e.g., treated to restore blood circulation.

In some embodiments, the subject has or is at risk of having reduced nutrient absorption, pain, nausea, diarrhea, and/or weight loss resulting from radiation, trauma or shock.

In some embodiments, the subject has necrotizing entercolitis, necrotic enteritis, short bowel syndrome or short gut syndrome.

In some embodiments, the method returns the GI tract to normal homeostasis. In some embodiments, the method improves absorption of nutrients from the GI tract.

In some embodiments, the method reduces traumatic insult.

In some embodiments, the method reduces overstimulation of the immune system. In some embodiments, the method regulates the initiation of regenerative pathways.

In some embodiments, the method promotes survival. In some embodiments, the method improves mortality.

In some embodiments, the method reduces damage to the GI tract. In some embodiments, the method improves healing of the epithelia and or the villi in the GI tract. In some embodiments, the method returns the GI tract to normal homeostasis. In some embodiments, the method reduces bacterial translocation across the GI tract. In some embodiments, the method improves absorption of nutrients from the GI tract.

In some embodiments, the method reduces local inflammation. In some embodiments, the method reduces systemic inflammation.

In some embodiments, the method reduces pain and suffering in the subject.

In some embodiments, the compound is administered at regular intervals. In some embodiments, the compound is administered periodically at regular intervals (e.g., 1, 2, 3, 4, 5, 6, 7, 8, 9, 10 or more times every 1, 2, 3, 4, 5, or 6 days).

In some embodiments, the compound is administered at a predetermined interval (e.g., 1, 2, 3, 4, 5, 6, 7, 8, 9, 10 or more times every 1, 2, 3, 4, 5, or 6 days). In some embodiments, the compound is administered once daily. In some embodiments, the compound is administered from about 1 to about 5 times per day. In some embodiments, the compound is administered from about 1 to about 3 times per day.

In some embodiments, the subject is treated for up to 3 weeks, 2 weeks, 1 week, 6 days, 5 days, 4 days, 3 days, 2 days, or 1 day.

In some embodiments, the subject is treated for 3 weeks, 2 weeks, 1 week, 6 days, 5 days, 4 days, 3 days, 2 days, or 1 day.

In some embodiments, the subject is treated within 1 hour, 2 hours, 3 hours, 4 hours, 5 hours, 6 hours, 8 hours, 10 hours, 12 hours, 16 hours, 20 hours, 24 hours, 2 days, 3 days, 4 days, 5 days, 6 days, 1 week, or 2 weeks after exposure to radiation, trauma, shock, or infection (e.g., bacterial or viral infection).

In some embodiments, the derivatized chitosan is functionalized at between 18% and 30%.

In some embodiments, the molecular weight of the derivatized chitosan is from 50 to 150 kDa (e.g., between 50 and 125 kDa, e.g., between 60 to 100 kDa, e.g., about 90 kDa).

In some embodiments, the polydispersity index of the derivatized chitosan is from 1.0 to 2.5. In some embodiments, the polydispersity index of the derivatized chitosan is from 1.5 to 2.0.

In one aspect, the invention features a method of treating a subject, the method comprising identifying a subject that has been exposed to radiation, trauma or shock and treating the subject with one of the following:
  a) a compound described herein, such as a polysaccharide described herein such as a polyglucosamine, e.g., a compound of Formula (I); or
  b) a compound that protects the mucosal lining of the gastrointestinal tract (GI) tract from translocation of bacteria across the gut, wherein the radiation, trauma or shock results in reduced integrity of the GI tract (e.g., leaky gut) of the subject,
  wherein upon administration of the compound to the subject, the compound treats, reduces the severity or delays the onset of sepsis or reduces the likelihood of mortality in a subject upon administration of a therapeutically effective amount of the compound to the subject, thereby treating the subject.

In some embodiments, the method reduces GI permeability and tissue damage after shock or trauma or after exposure to bacteria. In some embodiments, the method reduces GI damage or improves GI integrity after shock or trauma or after exposure to bacteria. In some embodiments, the method reduces damage to the subject from the radiation. In some embodiments, the method reduces inflammation, e.g., systemic inflammation, in the subject from the radiation.

In some embodiments, the method mitigates the inflammatory response in the GI tract. In some embodiments, the method reduces translocation of bacteria by up to 80%. In some embodiments, the method mitigates the systemic inflammatory response by reducing translocation of bacteria across the GI tract through mucoadhesive substantivity (e.g., adhesion, affinity) of the compound. In some embodiments, the method mitigates the inflammatory response by protecting epithelial cells from bacterial invasion. In some embodiments, the method reduces inflammation.

In some embodiments, the method promotes healing in a subject.

In some embodiments, the method reduces the severity or delays the onset of sepsis or reduces the likelihood of mortality in a subject relative to a subject not administered with the compound.

In some embodiments, the method mitigates inflammation and reduces mortality due to bacterial infection, bacterial translocation or chemical damage or radiation damage in the GI tract of a subject relative to a subject not administered with the compound.

In some embodiments, the method reduces mortality after exposure of the GI tract of a subject to ionizing radiation relative to a subject not administered with the compound.

In some embodiments, the method reduces crypt degeneration. In some embodiments, the method promotes the health of villous epithelium (e.g. reduces loss or blunting of villi).

In some embodiments, the source of radiation is a dirty bomb, accidental nuclear incident or therapeutic radiation, e.g. other than that related to the treatment of cancer. In some embodiments, the radiation causes physiologic changes in the GI tract. In some embodiments, the subject has been exposed to radiation in an amount sufficient to produce 30% to 80% lethality, e.g., at 30% to 80% lethal dose, at LD30 to LD80.

In some embodiments, the source of radiation is targeted to therapeutic treatment requiring destruction of the immune system, e.g., bone marrow transplant therapy or other elective exposure to radiation. In some embodiments, the therapeutic treatment causes the GI tract to become leaky or to lose integrity.

In some embodiments, the source of the trauma is exposure to a toxic chemical or poison. In some embodiments, the toxic chemical or poison is ingested.

In some embodiments, the source of the trauma is multiorgan failure due to accepted modes of failure, e.g., physical damage and trauma to the body, burns, blast injury, systemic infection, blood loss (hypotension), and traumatic brain injury.

In some embodiments, the source of shock is physical shock not resulting in a wound. In some embodiments, the source of shock is excessive stimuli, e.g. pathogens, commensals, injury, heat, autoantigens, tumors, necrotic cells. In some embodiments, the trauma results from a commensal or a pathogen translocating to an organ or tissue that is usually free of bacteria (e.g., an organ or tissue that is free of bacteria in the absence of trauma).

In some embodiments, the subject has a bacterial infection, chemical damage or radiation damage in the GI tract. In some embodiments, the subject has been exposed to sufficient radiation to cause a leaky GI tract or mucosal lesions. In some embodiments, the subject has been exposed to radiation in an amount sufficient to produce 30% to 80% lethality, e.g., at 30% to 80% lethal dose, at LD30 to LD80.

In some embodiments, the subject has leaky gut, wherein the leaky gut is a result of exposure to radiation, trauma or shock.

In some embodiments, the subject has sepsis or a symptom of sepsis resulting from radiation, trauma or shock. In some embodiments, the sepsis is caused by leaky gut. In some embodiments, the subject is at risk of developing sepsis as a result of exposure to radiation, trauma or shock.

In some embodiments, the subject has or is at risk of hypotension, e.g., reduced blood pressure as a physical manifestation of radiation, trauma or shock. In some embodiments, the subject has suffered reperfusion injury, e.g., treated to restore blood circulation.

In some embodiments, the subject has or is at risk of having reduced nutrient absorption, pain, nausea, diarrhea, and/or weight loss resulting from radiation, trauma or shock.

In some embodiments, the subject has necrotizing enterocolitis, necrotic enteritis, short bowel syndrome or short gut syndrome.

In some embodiments, the subject has a bacterial infection wherein the bacteria is *Salmonella enterica* serovar *Typhimurium, Shigella flexneri, E. coli* or *P. aeruginosa*.

In some embodiments, the compound is a polyglucosamine. Exemplary polyglucosamines include those soluble at acid, physiological pH or more basic pH (e.g., the pH of the digestive tract), e.g., the pH of the intestine (e.g., small intestine or large intestine) or colon; and or a charged polyglucosamine, e.g., poly (acetyl, arginyl) glucosamine (PAAG). In some embodiments, the polyglucosamine is a chitosan, e.g., a chitosan soluble at physiological pH.

In some embodiments, the soluble polyglucosamine comprises a polyglucosamine of the following Formula (I):

$$\text{Formula (I)}$$

wherein n is an integer between 20 and 6000; and each $R^1$ is independently selected for each occurrence from hydrogen, acetyl, and either a) a group of Formula (II):

$$\text{Formula (II)}$$

wherein $R^2$ is hydrogen or amino; and $R^3$ is amino, guanidino, $C_1$-$C_6$ alkyl substituted with an amino or guanidino moiety, or a natural or unnatural amino acid side chain; or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of Formula (II) or are taken together with the nitrogen to which they are attached to form a guanidine moiety.

In some embodiments, the soluble polyglucosamine comprises a polyglucosamine of the following Formula (I), wherein at least 90% by number or weight of $R^1$ moieties are as defined in Formula (I) (e.g., at least about 95%, at least about 96%, at least about 97%, at least about 98%, or at least about 99%):

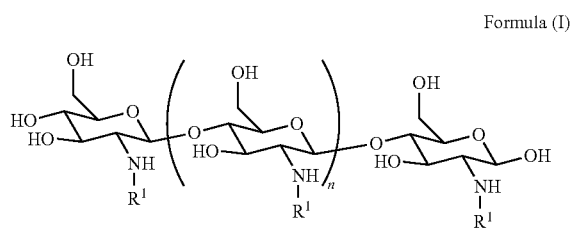

Formula (I)

wherein n is an integer between 20 and 6000; and each $R^1$ is independently selected for each occurrence from hydrogen, acetyl, and either a) a group of Formula (II):

Formula (II)

wherein $R^2$ is hydrogen or amino; and $R^3$ is amino, guanidino, $C_1$-$C_6$ alkyl substituted with an amino or guanidino moiety, or a natural or unnatural amino acid side chain; or b) $R^1$, when taken together with the nitrogen to which it is attached, forms a guanidine moiety; wherein at least 25% of $R^1$ substituents are H, at least 1% of $R^1$ substituents are acetyl, and at least 2% of $R^1$ substituents are a group of Formula (II) or are taken together with the nitrogen to which they are attached to form a guanidine moiety.

In some embodiments, between 25-95% of $R^1$ substituents are hydrogen. In some embodiments, between 55-90% of $R^1$ substituents are hydrogen.

In some embodiments, between 1-50% of $R^1$ substituents are acetyl. In some embodiments, between 4-20% of $R^1$ substituents are acetyl.

In some embodiments, between 2-50% of $R^1$ substituents are a group of Formula (II). In some embodiments, between 4-30% of $R^1$ substituents are a group of Formula (II).

In some embodiments, 55-90% of $R^1$ substituents are hydrogen, 4-20% of $R^1$ substituents are acetyl, 4-30% of $R^1$ substituents are a group of Formula (II).

In some embodiments, $R^2$ is amino and $R^3$ is an arginine side chain.

In some embodiments, $R^1$ is selected from one of the following:

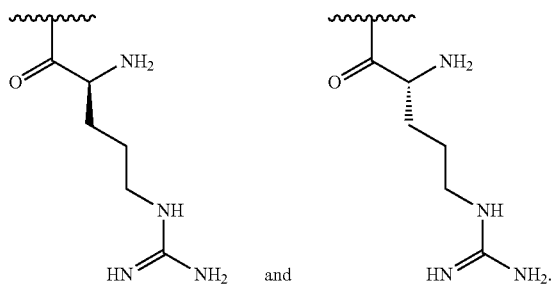 [SMILES: *C(=O)[C@@H](N)CCCNC(=N)N ; "and" ; *C(=O)[C@H](N)CCCNC(=N)N]

In some embodiments, $R^2$ is amino and $R^3$ is a lysine side chain.

In some embodiments, $R^1$ is selected from one of the following:

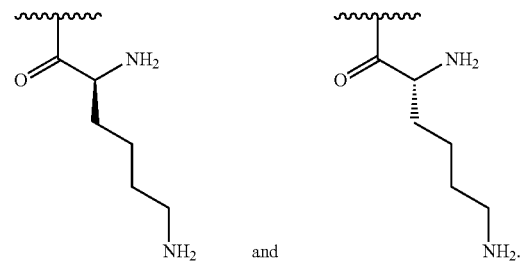 [SMILES: *C(=O)[C@@H](N)CCCCN ; "and" ; *C(=O)[C@H](N)CCCCN]

In some embodiments, $R^2$ is amino and $R^3$ is a histidine side chain.

In some embodiments, $R^1$ is selected from one of the following:

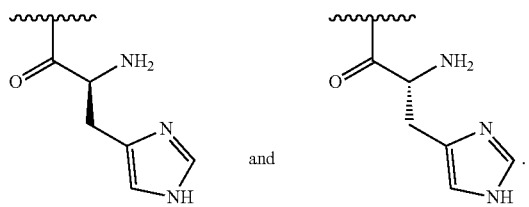 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

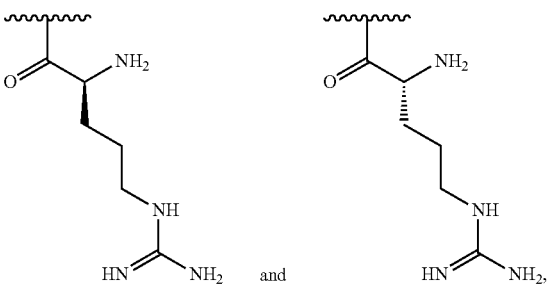 [SMILES: *C(=O)[C@@H](N)CCCNC(=N)N ; "and" ; *C(=O)[C@H](N)CCCNC(=N)N]

and at least 1% of $R^1$ substituents are selected from the following:

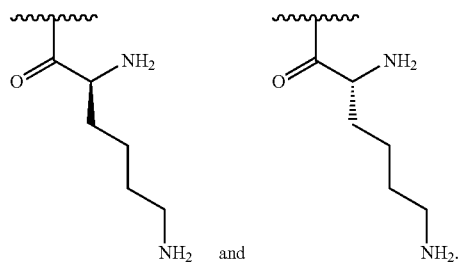 [SMILES: *C(=O)[C@@H](N)CCCCN ; "and" ; *C(=O)[C@H](N)CCCCN]

In some embodiments, $R^2$ is amino and $R^3$ is a substituted $C_1$-$C_6$ alkyl.

In some embodiments, $R^3$ is $C_1$-$C_6$ alkyl substituted with an amino group. In some embodiments, $R^3$ is $C_1$ alkyl substituted with an amino group. In some embodiments, $R^3$ is $C_2$ alkyl substituted with an amino group. In some embodiments, $R^3$ is $C_3$ alkyl substituted with an amino group. In some embodiments, $R^3$ is $C_4$ alkyl substituted with an amino group. In some embodiments, $R^3$ is $C_5$ alkyl substituted with an amino group. In some embodiments, $R^3$ is $C_6$ alkyl substituted with an amino group. In some embodiments, $R^1$ is selected from one of the following:

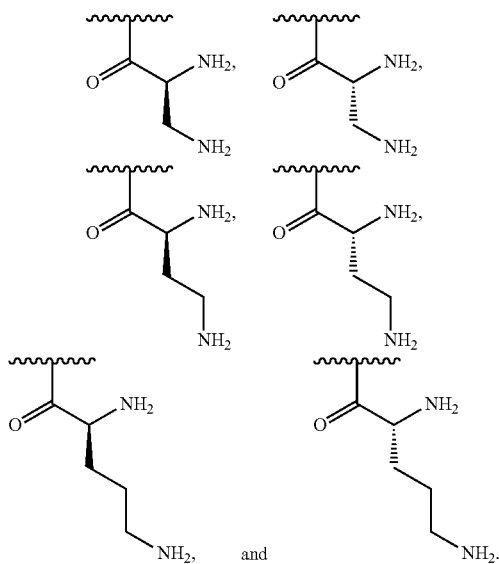

In some embodiments, $R^3$ is $C_1$-$C_6$ alkyl substituted with a guanidino group. In some embodiments, $R^3$ is $C_1$ alkyl substituted with a guanidino group. In some embodiments, $R^3$ is $C_2$ alkyl substituted with a guanidino group. In some embodiments. $R^3$ is $C_3$ alkyl substituted with a guanidino group. In some embodiments, $R^3$ is $C_4$ alkyl substituted with a guanidino group. In some embodiments, $R^3$ is $C_5$ alkyl substituted with a guanidino group. In some embodiments, $R^3$ is $C_6$ alkyl substituted with a guanidino group. In some embodiments, $R^1$ is selected from one of the following:

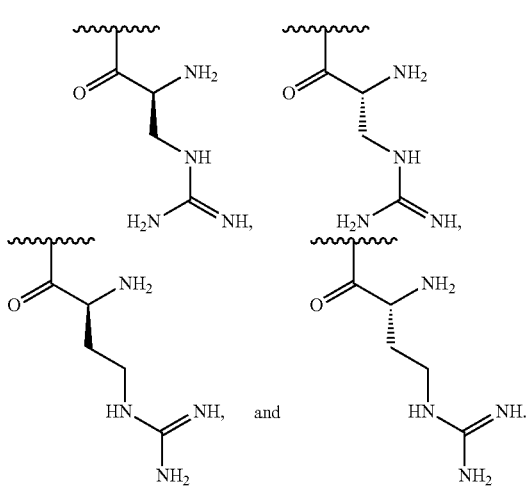

In some embodiments, wherein $R^2$ is amino that is substituted with a nitrogen protecting group prior to substitution (e.g., functionalization) on the polyglucosamine and removed subsequent to substitution (e.g., functionalization) on the polyglucosamine.

In some embodiments, the nitrogen protecting group is tert-butyloxycarbonyl (Boc).

In some embodiments, a nitrogen protecting group is used in the synthetic process, which can provide an intermediate polymer having a nitrogen protecting group such as Boc.

In some embodiments, $R^2$ is amino.
In some embodiments, $R^2$ is hydrogen and $R^3$ is amino.
In some embodiments, $R^2$ is hydrogen and $R^3$ is guanidino.

In some embodiments, $R^2$ is hydrogen and $R^3$ is a substituted $C_1$-$C_6$ alkyl. In some embodiments, $R^3$ is $C_1$-$C_6$ alkyl substituted with an amino group. In some embodiments, $R^3$ is $C_1$ alkyl substituted with an amino group. In some embodiments, $R^3$ is $C_2$ alkyl substituted with an amino group. In some embodiments, $R^3$ is $C_3$ alkyl substituted with an amino group. In some embodiments, $R^3$ is $C_4$ alkyl substituted with an amino group. In some embodiments, $R^3$ is $C_5$ alkyl substituted with an amino group. In some embodiments, $R^3$ is $C_6$ alkyl substituted with an amino group. In some embodiments, $R^1$ is selected from one of the following:

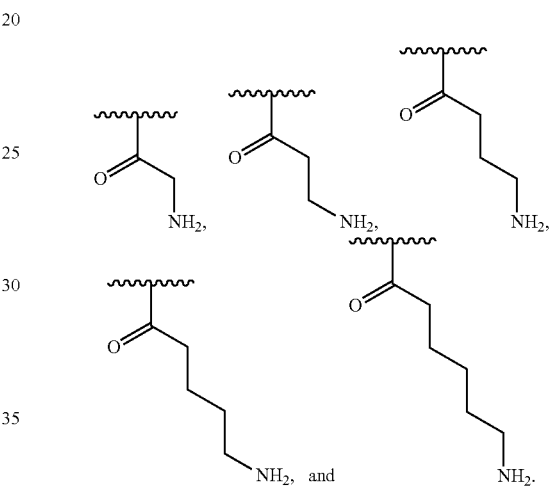

In some embodiments, $R^3$ is $C_1$-$C_6$ alkyl substituted with a guanidino group. In some embodiments, $R^3$ is $C_1$ alkyl substituted with a guanidino group. In some embodiments, $R^3$ is $C_2$ alkyl substituted with a guanidino group. In some embodiments, $R^3$ is $C_3$ alkyl substituted with a guanidino group. In some embodiments, $R^3$ is $C_4$ alkyl substituted with a guanidino group. In some embodiments, $R^3$ is $C_5$ alkyl substituted with a guanidino group. In some embodiments, $R^3$ is $C_6$ alkyl substituted with a guanidino group. In some embodiments, $R^1$ is selected from one of the following:

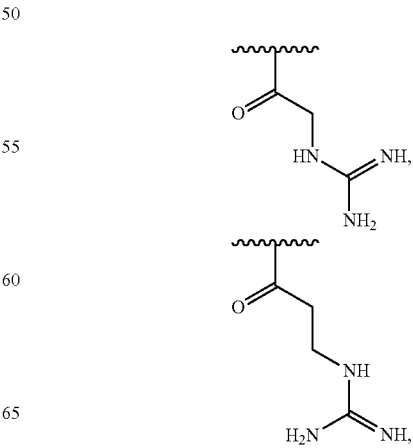

-continued

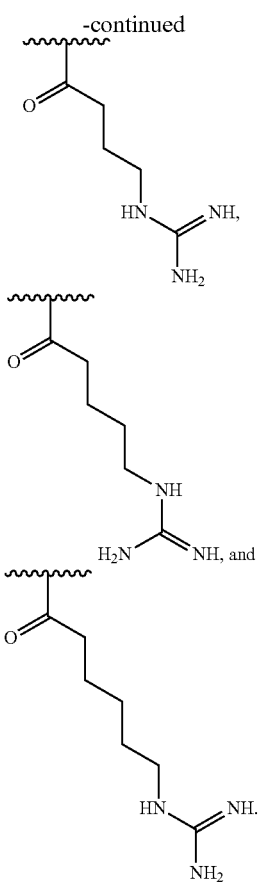

In some embodiments, at least 25% of $R^1$ substituents are H, at least 1% of $R^1$ substituents are acetyl, and at least 2% of $R^1$ substituents are independently selected from any of the formulae specifically shown above.

In some embodiments, the functionalized polyglucosamine of Formula (I) may be further derivatized (i.e., functionalized) on the free hydroxyl moieties.

In some embodiments, the molecular weight of the functionalized polyglucosamine is between 5and 1,000 kDa. In some embodiments, the molecular weight of the functionalized polyglucosamine is between 10 and 350 kDa. In some embodiments, the molecular weight of the functionalized polyglucosamine is between 15 and 200 kDa. In some embodiments, the molecular weight of the functionalized polyglucosamine is between 25 and 175 kDa. In some embodiments, the molecular weight of the functionalized polyglucosamine is between 50 and 150 kDa (e.g., between 50 and 125 kDa, e.g., between 60 to 100 kDa, e.g., about 90 kDa).

In some embodiments, the functionalized polyglucosamine is soluble in aqueous solution between pH 3 and 11. In some embodiments, the functionalized polyglucosamine is soluble in aqueous solution between pH 2 and 10. In some embodiments, the functionalized polyglucosamine is soluble in aqueous solution between pH 5 and 9. In some embodiments, the functionalized polyglucosamine is soluble in aqueous solution between pH 6.8 and pH 7.4.

In some embodiments, the functionalized polyglucosamine is soluble in aqueous solution at all physiological pH ranges.

In some embodiments, the functionalized polyglucosamine is soluble in aqueous solution at all pH ranges of the gastrointestinal tract, e.g., pH 3.

In some embodiments, the functionalized polyglucosamine is soluble in aqueous solution at all pH ranges of the intestinal tract, e.g., small intestine, e.g., at up to pH 8.

In some embodiments, the polyglucosamine is functionalized at between 5% and 50%. In some embodiments, the polyglucosamine is functionalized at between 15% and 35%.

In some embodiments, the degree of deacetylation (% DDA) of the derivatized (i.e., functionalized) polyglucosamine is between 75% and 99%. In some embodiments, the degree of deacetylation (% DDA) of the derivatized (i.e., functionalized) polyglucosamine is between 80% and 98%.

In some embodiments, the polydispersity index (PDT) of the derivatized (i.e., functionalized) polyglucosamine is between 1.0 and 2.5. In some embodiments, the polydispersity index (PDI) of the derivatized (i.e., functionalized) polyglucosamine is between 1.2 and 1.8.

In some embodiments, the functionalized polyglucosamine is substantially free of other impurities.

In some embodiments, the compound is administered orally.

In some embodiments, the compound is administered by enema.

In some embodiments, the compound is administered to the GI tract of the subject.

In some embodiments, the compound is administered to the subject after 24 hours of the subject's exposure to radiation, trauma or shock.

In some embodiments, the compound is administered to the subject within 24 hours of the subject's exposure to radiation, trauma or shock.

In some embodiments, the compound is administered to the subject prior to the subject's exposure to radiation, trauma or shock.

In some embodiments, the compound is administered in a therapeutically effective amount. In some embodiments, the therapeutically effective amount is up to 100 mg/kg. In another embodiment, the effective amount is 5 to 500 mg/kg. In another embodiment, the effective amount is 1 to 50 mg/kg. In another embodiment, the effective amount is 5 to 50 mg/kg with additional dosing of 100 to 500 µg/ml in solution.

In another embodiment, the therapeutically effective amount is up to 100 ug/kg.

In some embodiments, the compound is administered for 1 day, 2 days, 4 days, 1 week, 2 weeks, 4 weeks or until symptoms cease.

In another embodiment, the effective amount is 40 µg/kg thrice daily.

In some embodiments, the treatment reduces traumatic insult. In some embodiments, the treatment reduces overstimulation of the immune system. In some embodiments, the treatment regulates the initiation of regenerative pathways. In some embodiments, the treatment promotes survival. In some embodiments, the treatment reduces damage to the GI tract. In some embodiments, the treatment improves healing of the epithelia and or the villi in the GI tract. In some embodiments, the treatment improves mortality. In some embodiments, treatment returns the GT tract to normal homeostasis. In some embodiments, the treatment reduces bacterial translocation across the GI tract. In some embodiments, the treatment improves absorption of nutrients from the GI tract.

In some embodiments, the treatment reduces local inflammation. In some embodiments, the treatment reduces systemic inflammation.

In some embodiments, the treatment reduces the World Health Organization (WHO) mucositis score. In some embodiments, the method reduces the percentage of animals with a WHO mucositis score greater than or equal to 3. In some embodiments, the method reduces ulceration 10% or more in a subject.

In one aspect, the invention features a method of prophylactic treatment of a subject, the method comprising identifying a subject that will be exposed to radiation, trauma or shock; and prior to exposure to radiation, trauma or shock, treating the subject with one of the following:
 a) a compound described herein, such as a polysaccharide described herein such as a polyglucosamine, e.g., a compound of Formula (I); or
 b) a compound that protects the mucosal lining of the gastrointestinal tract (GI) tract from translocation of bacteria across the gut, wherein the radiation, trauma or shock results in reduced integrity of the GI tract (e.g., leaky gut) of the subject,
wherein upon administration of the compound to the subject, the compound treats, reduces the severity or delays the onset of sepsis or reduces the likelihood of mortality in a subject upon administration of a therapeutically effective amount the compound to the subject, thereby prophylactically treating the subject.

In one aspect, the invention features a method of reducing the severity or delaying the onset of sepsis or decreasing the likelihood of mortality of a subject that has been exposed to radiation, trauma or shock; the method comprising administering to the subject one of the following:
 a) a compound described herein, such as a polysaccharide described herein such as a polyglucosamine, e.g., a compound of Formula (I); or
 b) a compound that protects the mucosal lining of the gastrointestinal tract (GI) tract from translocation of bacteria across the gut, wherein the radiation, trauma or shock results in reduced integrity of the GI tract (e.g., leaky gut) of the subject,
wherein upon administration of the compound to the subject, the compound reduces the severity or delays the onset of sepsis or reduces the likelihood of mortality in a subject upon administration of a therapeutically effective amount the compound to the subject, thereby treating the subject.

In one aspect, the invention features a method of reducing the severity or delaying the onset of sepsis or decreasing the likelihood of mortality of a subject that will be exposed to radiation, trauma or shock; the method comprising prophylactic administration to the subject one of the following:
 a) a compound described herein, such as a polysaccharide described herein such as a polyglucosamine, e.g., a compound of Formula (I); or
 b) a compound that protects the mucosal lining of the gastrointestinal tract (GI) tract from translocation of bacteria across the gut, wherein the radiation, trauma or shock results in reduced integrity of the GI tract (e.g., leaky gut) of the subject,
wherein upon administration of the compound to the subject, the compound reduces the severity or delays the onset of sepsis or reduces the likelihood of mortality in a subject upon prophylactic administration of a therapeutically effective amount of the compound to the subject, thereby treating the subject.

In one aspect, the invention features a method of treating mucositis (e.g., in the gastrointestinal (GI) tract) in a subject exposed to radiation, trauma or shock, the method comprising identifying a subject that has been exposed to radiation, trauma or shock; and treating the subject with one of the following:
 a) a compound described herein, such as a polysaccharide described herein such as a polyglucosamine, e.g., a compound of Formula (I); or
 b) a compound that protects the mucosal lining of the GI tract from translocation of bacteria across the gut, wherein the radiation, trauma or shock results in reduced integrity of the GI tract (e.g., leaky gut) of the subject,
wherein upon treating the subject with a therapeutically effective amount of the compound to the subject, the compound treats mucositis in a subject that has been exposed to radiation, trauma or shock, thereby treating the subject.

DETAILED DESCRIPTION

Figure 1:
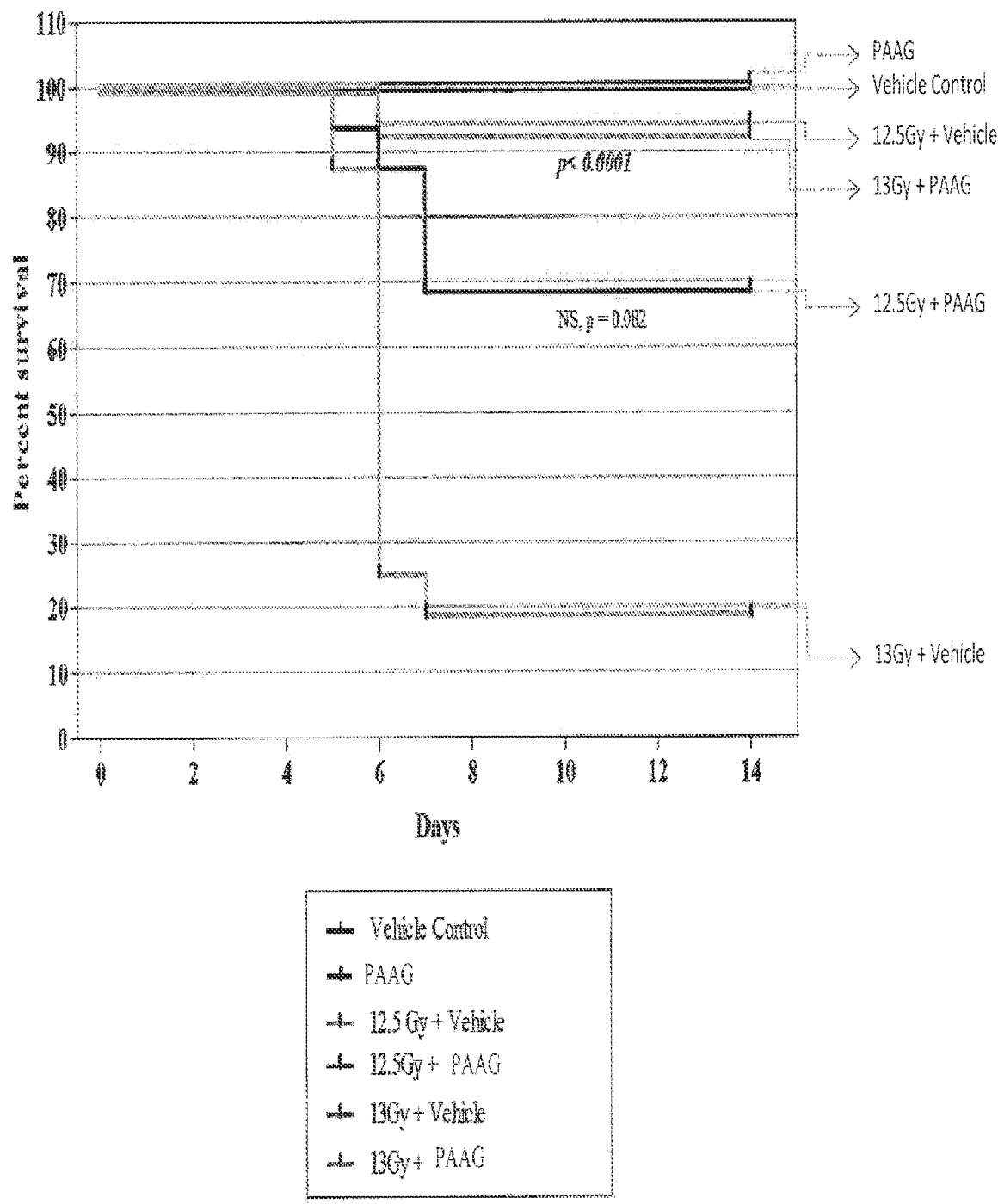
FIG. 1 depicts an exemplary effect of PAAG and radiation treatment on survival.

Described herein are methods of treating a subject, for example, either prior to or subsequent to when the subject has been exposed to or experienced radiation, trauma, or shock. In some embodiments, the methods of treating a subject can help treat and/or prevent leaky gut in a subject. In some embodiments, the methods of treating a subject can help prevent the subject from experiencing sepsis, or reduce the severity of the sepsis. This can be achieved by administering to the subject a compound described herein. Examples of such compounds include polysaccharides, including polyglucosamines such as those described herein (e.g., a compound of Formula (I)). In some embodiments, the treatment can reduce the severity of a symptom or decrease the likelihood of mortality of a subject that has been or will be exposed to radiation, trauma or shock. In some embodiments, the compound protects the mucosal lining of the GI tract from allowing bacterial translocation across the gut. In some embodiments, the compound inhibits binding of bacteria or toxins, endotoxins, mitochondria, pathogen associated molecular patterns (PAMPs), damage associated molecular patterns (DAMPs), and chemotherapy and radiation associated molecular patterns (CRAMPs) in the subject with an innate immune receptor such as Toll-like Receptor 4 (TLR4). In some embodiments, the compound reduces TNF-expression in response to Lipopolysaccharide (LPS). In some embodiments, the compound reduces IL-8 production in response to PAMP or CRAMP stimuli. In some embodiments, the compound inhibits bacterial adhesion to cells of the mucosal lining of the GI tract of the subject.

Treatment

The compositions and compounds described herein (e.g., a compound that protects the mucosal lining or integrity of the GI tract, such as a soluble polyglucosamine or a derivatized (i.e., functionalized) polyglucosamine described herein) can be administered to a tissue, e.g. in vitro or ex vivo, or to a subject, e.g., in vivo, to treat and/or prevent a variety of conditions resulting from radiation, trauma or shock, including those described herein below.

As used herein, the term "treat" or "treatment" is defined as the application or administration of a composition or compound (e.g., a compound described herein (e.g., a compound that protects the mucosal lining of the GI tract such as a soluble or derivatized (i.e., functionalized) polyglucosamine described herein)) to a subject, e.g., a patient, or application or administration of the composition or compound to an isolated tissue, from a subject, e.g., a patient, who has been exposed to radiation, trauma or shock, with the purpose to cure, heal, alleviate, relieve, alter, remedy, ameliorate, improve and/or affect the subject, one or more symptoms of a disorder described herein or the predisposition toward a disorder described herein (e.g., to prevent at least one symptom of the disorder described herein and/or to delay onset of at least one symptom of the disorder described herein), and/or a side or adverse effect of radiation, trauma or shock. A subject is successfully "treated" if, after receiving an effective amount of one or more active agents described herein, the subject shows observable and/or measurable reduction in or absence of morbidity and/or mortality, improvement in nutrient adsorption, reduction of pain, reduction of nausea, reduction of diarrhea, reduction in weight loss and/or improvement in quality of life issues.

As used herein, the term "prevent" or "prevention" is defined as the application or administration of a composition or compound (e.g., a compound described herein (e.g., a soluble or derivatized (i.e., functionalized) polyglucosamine)) to a subject, e.g., a subject who is at risk for a disorder (e.g., a disorder described herein), or has a disposition toward a disorder described herein, or application or administration of the compound to an isolated tissue from a subject, e.g., a subject who is at risk for a disorder (e.g., a disorder as described herein), or has a predisposition toward a disorder described herein, with the purpose to avoid or preclude the disorder described herein, or affect the predisposition toward the disorder described herein (e.g., to prevent at least one symptom of the disorder described herein or to delay onset of at least one symptom of the disorder described herein). "Preventing" a disease may also be referred to as "prophylaxis" or "prophylactic treatment."

As used herein, an amount of a composition or compound effective to treat a disorder described herein, or a "therapeutically effective amount" refers to an amount of the composition or compound which is effective, upon single or multiple dose administration to a subject, in treating a tissue, or in curing, alleviating, relieving or improving a subject with a disorder described herein beyond that expected in the absence of such treatment.

As used herein, an amount of a composition or compound effective to prevent a disorder described herein, or "a prophylactically effective amount" of the composition or compound refers to an amount effective, upon single- or multiple-dose administration to the subject, in preventing or delaying the occurrence of the onset or recurrence of a disorder described herein or a symptom of the disorder described herein. Typically, because a prophylactic dose is used in subjects prior to or at an earlier stage of disease, the prophylactically effective amount will be less than the therapeutically effective amount.

As used herein, "administered in combination" or a combined administration of two agents means that two or more agents (e.g., compounds described herein) are administered to a subject at the same time or within an interval such that there is overlap of an effect of each agent on the patient. Preferably they are administered within 60, 30, 15, 10, 5, or 1 minute of one another. Preferably the administrations of the agents are spaced sufficiently close together such that a combinatorial (e.g., a synergistic) effect is achieved. The combinations can have synergistic effect when used to treat a subject having a bacterial infection. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject. Alternately, the soluble polyglucosamine or polyglucosamine derivative can be administered topically, intranasally, via pulmonary aerosol or orally, and the second agent can be administered systemically.

In an embodiment, the agents are administered essentially simultaneously, for example two unit dosages administered at the same time, or a combined unit dosage of the two agents. In another embodiment, the agents are delivered in separate unit dosages. The agents can be administered in any order, or as one or more preparations that includes two or more agents. Alternatively, the second agent can be administered systemically and can be available systemically during the administration of the first agent. In an embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 1.25, 1.5, 2, 4, 10, 20, 40, or 100, 1000, 100000, or 100000 times greater than additive.

Trauma can be an injury e.g., a physical injury or insult, caused by an external source, e.g., from a fracture or blow. Trauma is the sixth leading cause of death worldwide, accounting for 10% of all mortalities, and is therefore a serious public health problem with significant social and economic costs. Trauma can lead to significant and rapid blood loss, which can result in phyisological shock. Trauma can also be a result of infection, e.g., bacterial, viral, or fungal infection.

Shock is a failure of the circulatory system to supply sufficient blood to peripheral tissues to meet basic needs including metabolic requirements for oxygen and nutrients and incomplete removal of metabolic wastes from the affected tissues. Shock is usually caused by hemorrhage or overwhelming infection and is characterized in most cases by a weak, rapid pulse; low blood pressure; and cold, sweaty skin. Shock may result from a variety of physiological mechanisms, including sudden reductions in the total blood volume such as severe hemorrhage; sudden reductions in cardiac output, as in myocardial infarction (heart attack); and widespread dilation of the blood vessels, as in some forms of infection. Typical signs of shock include low blood pressure, a rapid heartbeat and signs of poor end-organ perfusion or "decompensation" (such as low urine output, confusion or loss of consciousness). However, a subject's blood pressure may also remain stable and still be in circulatory shock. Shock can include circulatory shock, which can be a life-threatening medical condition that occurs due to inadequate substrate for aerobic cellular respiration. Circulatory shock can be a life-threatening medical emergency and one of the most common causes of death for critically ill people. Shock can have a variety of effects, all with similar outcomes, but all relate to a problem with the body's circulatory system. For example, shock may lead to hypoxemia (a lack of oxygen in arterial blood) or cardiac arrest.

Subject

The subject can be a human or a non-human animal. Suitable human subjects includes, e.g., a human patient that has been or will be exposed to radiation, trauma or shock or damage as a result of exposure to radiation, trauma or shock described herein or a normal subject. The term "non-human animals" of the invention includes all vertebrates, e.g., non-mammals (such as chickens, amphibians, reptiles) and mammals, such as non-human primates, e.g., elephant, sheep, dog, cat, cow, and pig. Suitable animal subjects include: but are not limited to, wild animals, farm animals, zoo animals, circus animals, companion (pet) animals, domesticated and/or agriculturally useful animals. Suitable animal subjects include primates, rodents, and birds. Examples of said animals include, but are not limited to, elephants, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), waterfowl, ostriches, chickens, turkeys, ducks, and geese or free flying bird.

In some embodiments, the subject has been exposed to radiation, e.g., from a dirty bomb, accidental nuclear incident or therapeutic radiation, e.g. other than that related to the treatment of cancer. In some embodiments, the subject has been exposed to a chemical, biological or radiological agent, or has suffered chemical, biological, or radiological injury. In some embodiments, the source of the trauma is exposure to a toxic chemical or poison. In some embodiments, the toxic chemical or poison is ingested. In some embodiments, the subject is at risk for sepsis and/or death resulting from the radiation, trauma or shock.

In some embodiments, the source of radiation is targeted to therapeutic treatment requiring destruction of the immune system, e.g., bone marrow transplant therapy or other elective exposure to radiation. In some embodiments, the subject has been exposed to radiation in an amount sufficient to produce 30% to 80% lethality, e.g., at 30% to 80% lethal dose, at LD30 to LD80. In some embodiments, the radiation is 12 to 15 Gy radiation.

In some embodiments, the source of the trauma is multiorgan failure due to accepted modes of failure, e.g., physical damage and trauma to the body, burns, blast injury, systemic infection, blood loss (hypotension), traumatic brain injury.
Sepsis Methods of treating a subject who has sepsis or displays symptoms of sepsis are described herein. In some embodiments, the subject is at risk of sepsis as a result of exposure to radiation, trauma or shock. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "bacteremia" includes occult bacteremia observed in young febrile children with no apparent foci of infection. The term "sepsis" also encompass that caused by fungemia (i.e., fungi in the blood), viremia (i.e., viruses or virus particles in the blood), and parasitemia (i.e., helminthic or protozoan parasites in the blood). Gram-negative sepsis is a common type of sepsis and is caused by *Escherichia coli*, *Klebsiella pneumonia* and *Pseudomonas aeruginosa*. Gram-positive pathogens such as the Staphylococci and Streptococci also causes of sepsis. A third major group that causes sepsis includes fungi.

Phenotypes associated with septicemia and septic shock (acute circulatory failure resulting from septicemia often associated with multiple organ failure and a high mortality rate) are symptoms of sepsis. Symptoms of sepsis in a subject include but are not limited to, increased respiration, increased heart rate, reduced arterial $CO_2$ saturation, arterial hypotension, metabolic acidosis, fever, decreased systemic vascular resistance, tachypnea and organ dysfunction (as manifest by, but not limited to, elevated transaminase, creatinine, and blood urea nitrogen).

Chemical Warfare Agents and Injury

Methods of treating a subject who has been exposed to a chemical warfare agent or has suffered a chemical warfare injury are described herein. Chemical agents that can cause chemical injury in a subject and/or be used as a chemical warfare agent include, e.g., harassing agents (e.g., tear agents or lachrymatory agents (e.g., α-chlorotoluene, benzyl bromide, bromoacetone (BA), bromobenzylcyanide (CA), bromomethyl ethyl ketone, capsaicin (OC), chloracetophenone (MACE; CN), chloromethyl chloroformate, dibenzoxazepine (CR), ethyl iodoacetate, ortho-chlorobenzylidene malononitrile (super tear gas; CS), trichloromethyl chloroformate, and xylyl bromide), vomiting agents (e.g., adamsite (DM), diphenylchloroarsine (DA), diphenylcyanoarsine (DC))), incapacitating agents (e.g., psychological agents (e.g., 3-quinuclidinyl benzilate (BZ), phencyclidine (SN), lysergic acid diethylamide (K)), KOLOKOL-1 (tranquilizer)), lethal agents (e.g., blister agents (e.g., vesicants (e.g., nitrogen mustards (e.g., bis(2-chloroethyl)ethylamine (HN1), bis(2-chloroethyl)methylamine (HN2), tris(2-chloroethyl)amine (HN3), sulfur mustards (e.g., 1,2-bis(2-chloroethylthio) ethane (Sesquimustard; Q), 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide (mustard gas; HD), bis(2-chloroethylthio) methane, bis(2-chloroethylthiomethyl) ether, bis(2-chloroethylthioethyl) ether (0 mustard; T)), arsenicals (e.g., ethyldichloroarsine (ED), methyldichloroarsine (MD), phenyldichloroarsine (PD), 2-chlorovinyldichloroarsine (Lewisite; L))), urticants (e.g., phosgene oxime (CX))), blood agents (e.g., cyanogen chloride (CK), hydrogen cyanide (AC), arsine (SA)), choking agents or pulmonary agents (e.g., chlorine (CL), chloropicrin (PS), diphosgene (DP), phosgene (CG)), nerve agents (e.g., G series (e.g., tabun (GA), sarin (GB), soman (GD), cyclosarin (GF)), GV series (e.g., novichok agents, GV (nerve agent)), V series (e.g., VE, VG, VM, VX)).

Leaky Gut

Methods of treating a subject who has leaky gut or symptoms of leaky gut are described herein. Leaky gut generally refers to intestinal or bowel hyperpermeability. The condition can allow toxins, bacteria, and food particles penetrate the lining of the intestinal tract and enter the body's blood stream. Leaky gut can refer to an acute condition resulting from exposure or insult (e.g., from radiation, trauma, shock, or infection (e.g., bacterial, viral, fungal infection). Leaky gut can result in sepsis. Acute conditions are generally severe and sudden in onset (e.g., a broken bone, an asthma attack). Leaky gut can lead to a condition of an altered or damaged bowel lining (e.g., mucosa of the intestinal tract is compromised) that is caused by increased permeability of the gut wall from e.g., toxins, poor diet, parasites, infection, or mediations. In some embodiments, the methods described herein treat an acute condition that can result in or be a symptom of leaky gut.

Research and clinical diagnostic tests are available but typically not relied upon for diagnosis of leaky gut. Probes of intermediate molecular weight (e.g., 150-400 g/mol, e.g., Cr EDTA, PEG 400, lactulose, mannitol, rhamnose) can be used to measure intestinal permeability and for analyzing urinary recovery. Measurement of the translocation of lipopolysaccharide molecules across the gut wall also may be used to characterize leaky gut.

Compounds for Treating or Prophylactically Treating a Subject

Methods for treating or prophylactically treating damage resulting from radiation, trauma or shock with a polyglucosamine compound or composition are described herein.

Soluble Polyglucosamines and Polyglucosamines Derivatives

The compounds described herein include polyglucosamines and polyglucosamine derivatives. Exemplary polyglucosamines include polyglucosamine compounds such as chitosan, e.g., a chitosan soluble in physiological pH.

Polyglucosamines can be derived from chitosan by deacetylation. Chitosan is an insoluble polymer derived from chitin, which is a polymer of N-acetylglucosamine that is the main component of the exoskeletons of crustaceans (e.g. shrimp, crab, lobster). Polyglucosamines are also found in various fungi and arthropods. Synthetic sources and alternate sources of β1-4 polyglucosamines may serve as the starting material for the polyglucosamine derivatives. The polyglucosamine derivatives described herein are generated by functionalizing the free amino groups with positively charged or neutral moieties, as described herein. Up to 50% of the amino groups are acetylated. For the purposes of this invention, if greater than 50% of the amino groups are acetylated, the polymer is considered a polyacetylglucosamine. The degrees of deacetylation and functionalization impart a specific charge density to the functionalized polyglucosamine derivative. The resulting charge density affects solubility and effectiveness of treatment. Thus, in accordance with the present invention, the degree of deacetylation, the functionalization and the molecular weight must be optimized for optimal efficacy. The derivatized (i.e., functionalized) polyglucosamines described herein have a number of properties which are advantageous including solubility at physiologic pH.

A soluble polyglucosamine as described herein refers to a water soluble chitosan or polyglucosamine that is not derivatized (i.e., functionalized) on the hydroxyl or amine moieties other than with acetyl groups. A soluble polyglucosamine is comprised of glucosamine and acetylglucosamine monomers. Generally, a water soluble polyglucosamine has a molecular weight of less than or equal to about 10,000 kDa (e.g., less than or equal to about 5,000 kDa, e.g., less than or equal to about 1,000 kDa) and a degree of deacetylation equal to or greater than 80%. In some embodiments, the molecular weight of the soluble polyglucosamine is between 5 and 1,000 kDa. In some embodiments, the molecular weight of the soluble polyglucosamine is between 10 and 350 kDa. In some embodiments, the molecular weight of the soluble polyglucosamine is between 15 and 200 kDa. In some embodiments, the molecular weight of the soluble polyglucosamine is between 25 and 175 kDa. In some embodiments, the molecular weight of the soluble polyglucosamine is between 50 and 150 kDa. The soluble polyglucosamines described herein are soluble at pH 2 to pH 11.

The polyglucosamine derivatives described herein are generated by functionalizing the resulting free amino and or hydroxyl groups with positively charged or neutral moieties, as described herein.

Polyglucosamines with any degree of deacetylation (DDA) greater than 50% are used in the present invention, with functionalization between 2% and 50% of the available amines. The degree of deacetylation determines the relative content of free amino groups to total monomers in the polyglucosamine polymer. Methods that can be used for determination of the degree of deacetylation of polyglucosamine include, e.g., ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble polyglucosamine or a derivatized (i.e., functionalized) polyglucosamine described herein is determined by quantitative infrared spectroscopy. Percent functionalization is determined as the % of derivatized (i.e., functionalized) amines relative to the total number of available amino moieties prior to reaction on the polyglucosamine polymer. Preferably, the percent functionalization of a derivatized (i.e., functionalized) polyglucosamine described herein is determined by H-NMR or quantitative elemental analysis. The degrees of deacetylation and functionalization impart a specific charge density to the functionalized polyglucosamine derivative. The resulting charge density affects solubility, and strength of interaction with cell membranes. The molecular weight is also an important factor in the tenacity of cell membrane interaction. Thus, in accordance with the present invention, these properties must be optimized for optimal efficacy. Exemplary polyglucosamine derivatives are described in U.S. Pat. No. 8,119,780, which is incorporated herein by reference in its entirety.

The polyglucosamine derivatives described herein have a range of polydispersity index (PDI) between about 1.0 to about 2.5. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g. chitin or chitosan from crab vs. shrimp vs. fungi) and can be affected by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble polyglucosamine or a derivatized (i.e., functionalized) polyglucosamine described herein is determined by HPLC and multi angle light scattering methods.

The polyglucosamine derivatives (i.e., derivatized polyglucosamines or functionalized polyglucosamines) described herein have a variety of selected molecular weights that are soluble at neutral and physiological pH, and include for the purposes of this invention molecular weights ranging from 5-1,000 kDa. Embodiments described herein are feature medium range molecular weight of derivatized (i.e., functionalized) polyglucosamines (25 kDa, e.g., from about 15 to about 300 kDa). In some embodiments, the molecular weight of the derivatized (i.e., functionalized) polyglucosamine is between 5 and 1,000 kDa. In some embodiments, the molecular weight of the derivatized (i.e., functionalized) polyglucosamine is between 10 and 350 kDa. In some embodiments, the molecular weight of the derivatized (i.e., functionalized) polyglucosamine is between 15 and 200 kDa. In some embodiments, the molecular weight of the functionalized polyglucosamine is between 25 and 175 kDa. In some embodiments, the molecular weight of the functionalized polyglucosamine is between 50 and 150 kDa (e.g., between 50 and 125 kDa, e.g., between 60 to 100 kDa, e.g., about 90 kDa).

The functionalized polyglucosamine derivatives described herein include the following:

(A) Polyglucosamine-arginine compounds;

(B) Polyglucosamine-natural amino acid derivative compounds;

(C) Polyglucosamine-unnatural amino acid compounds;

(D) Polyglucosamine-acid amine compounds;

(E) Polyglucosamine-guanidine compounds; and (F) Neutral polyglucosamine derivative compounds.

(A) Polyglucosamine-Arginine Compounds

In some embodiments, the present invention is directed to polyglucosamine-arginine compounds, where the arginine is bound through a peptide (amide) bond via its carbonyl to the primary amine on the glucosamines of polyglucosamine:

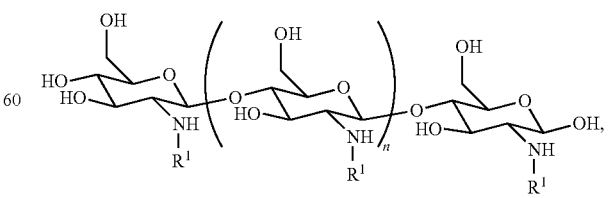

wherein each $R^1$ is independently selected from hydrogen, acetyl, and a group of the following formula:

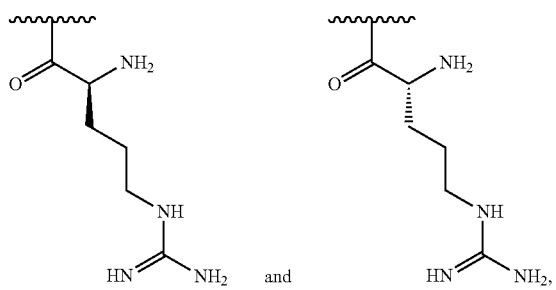

or a racemic mixture thereof, and wherein at least 25% of $R^1$ substituents are H, at least 1% are acetyl, and at least 2% are a group of the formula shown above.

In some embodiments, a polyglucosamine-arginine compound is of the following formula

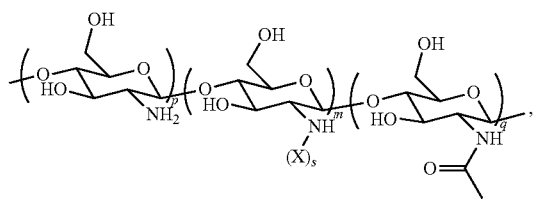

where m is 0.02-0.50; q is 0.50-0.01; s is 1; p+q+m=1; the percentage degree of functionalization is m·100%; and X is selected from the group consisting of:

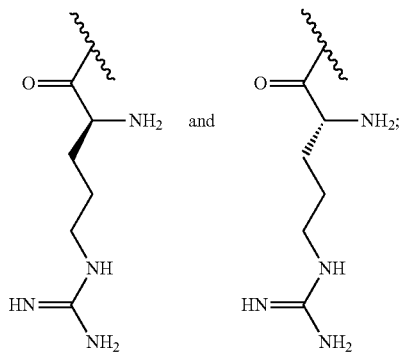 [SMILES: *C(=O)[C@@H](N)CCCNC(=N)N ; "and" ; *C(=O)[C@H](N)CCCNC(=N)N]

wherein the preparation is substantially free of compounds having a molecular weight of less than 5000 Da.

(B) Polyglucosamine-Natural Amino Acid Derivative Compounds

In some embodiments, the present invention is directed to polyglucosamine-natural amino acid derivative compounds, wherein the natural amino acid may be histidine or lysine. The amino is bound through a peptide (amide) bond via its carbonyl to the primary amine on the glucosamines of polyglucosamine:

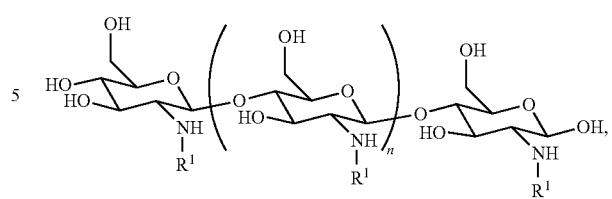

wherein each $R^1$ is independently selected from hydrogen, acetyl, and a group of the following formula:

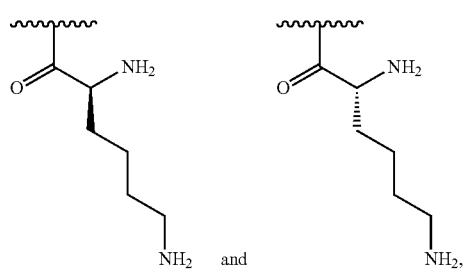 [SMILES: *C(=O)[C@@H](N)CCCCN ; "and" ; *C(=O)[C@H](N)CCCCN]

or a racemic mixture thereof, wherein at least 25% of $R^1$ substituents are H, at least 1% are acetyl, and at least 2% are a group of the formula shown above; or a group of the following formula:

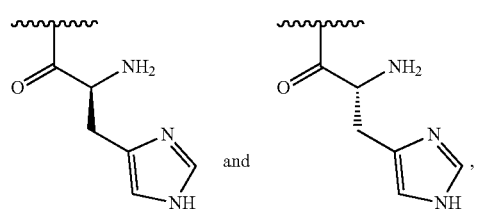 [SMILES: *C(=O)[C@@H](N)Cc1c[nH]cn1 ; *C(=O)[C@H](N)Cc1c[nH]cn1]

or a racemic mixture thereof, wherein at least 25% of $R^1$ substituents are H, at least 1% are acetyl, and at least 2% are a group of the formula shown above.

(C) Polyglucosamine-Unnatural Amino Acid Compounds

In some embodiments, the present invention is directed to polyglucosamine-unnatural amino acid compounds, where the unnatural amino acid is bound through a peptide (amide) bond via its carbonyl to the primary amine on the glucosamines of polyglucosamine:

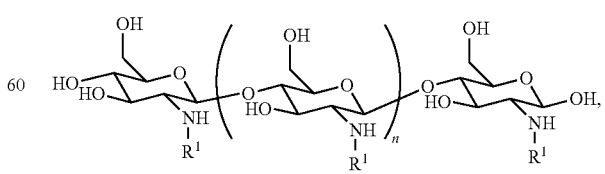

wherein each $R^1$ is independently selected from hydrogen, acetyl, and a group of the following formula:

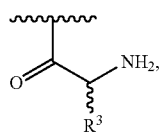

wherein R³ is an unnatural amino acid side chain, and wherein at least 25% of R¹ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acid coupled to polyglucosamine is selected from one of the following:

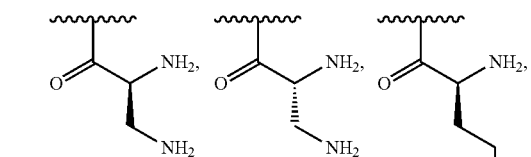

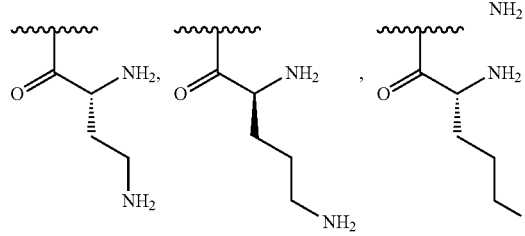

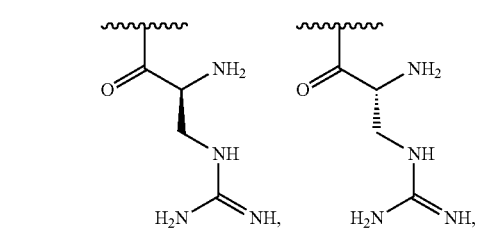

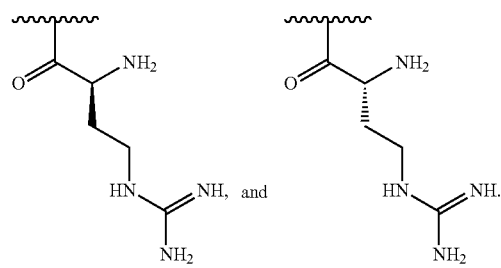

(D) Polyglucosamine-Acid Amine Compounds

In some embodiments, the present invention is directed to polyglucosamine-acid amine compounds, or their guanidylated counterparts. The acid amine is bound through a peptide (amide) bond via its carbonyl to the primary amine on the glucosamines of polyglucosamine:

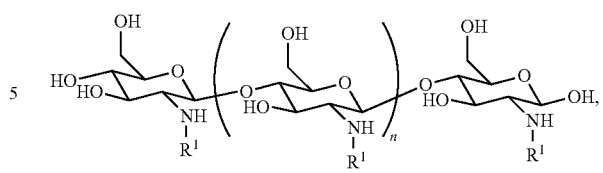

wherein each R¹ is independently selected from hydrogen, acetyl, and a group of the following formula:

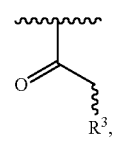

wherein R³ is selected from amino, guanidino, and $C_1$-$C_6$ alkyl substituted with an amino or a guanidino group, wherein at least 25% of R¹ substituents are H, at least 1% are acetyl, and at least 2% are a group of the formula shown above In some embodiments, R¹ is selected from one of the following:

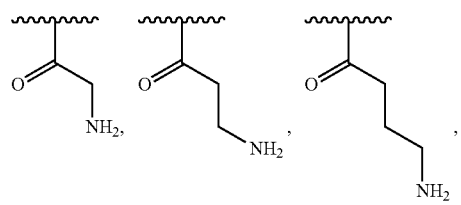

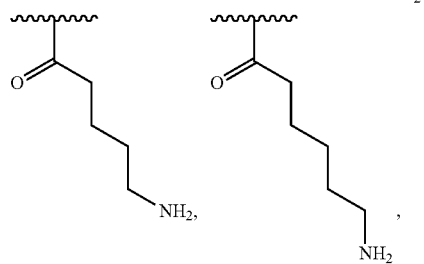

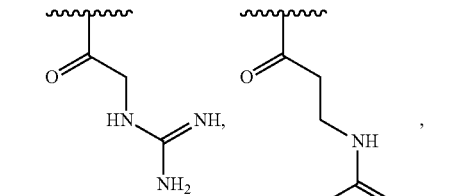

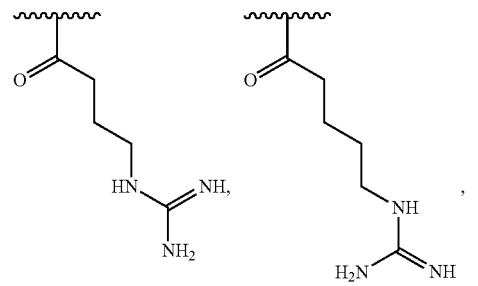

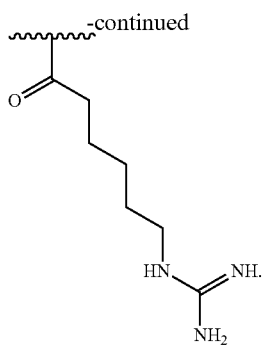

(E) Polyglucosamine-Guanidine Compounds

In some embodiments, the present invention is directed to polyglucosamine-guanidine compounds.

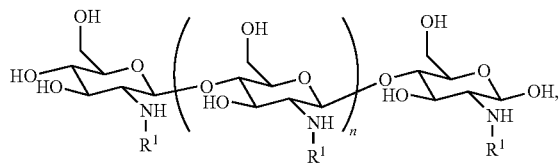

wherein each $R^1$ is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Polyglucosamine Derivative Compounds

In some embodiments, the present invention is directed to neutral polyglucosamine derivative compounds. Exemplary neutral polyglucosamine derivative compounds include those where one or more amine nitrogens of the polyglucosamine have been covalently attached to a neutral moiety such as a sugar:

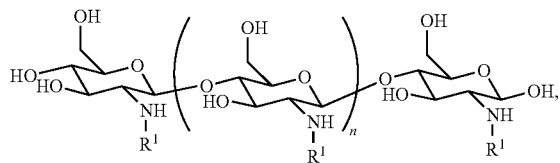

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellubiose, sucrose, amylose, glycogen, cellulose, gluconate, or pyruvate. Sugars can be covalently attached via a spacer or via the carboxylic acid, ketone or aldehyde group of the terminal sugar. Examples of α-hydroxy acids include glycolic acid, lactic acid, and citric acid. In some embodiments, the neutral polyglucosamine derivative is polyglucosamine-lactobionic acid compound or polyglucosamine-glycolic acid compound. Exemplary salts and coderivatives include those known in the art, for example, those described in U.S. Pat. No. 8,119,780, the contents of which is incorporated by reference in its entirety.

Formulations and Routes of Administration

The compounds described herein can be formulated in a variety of manners, including for topical delivery, oral delivery or delivery to the GI tract. For example, the compounds can be administered, e.g., topically (e.g., by solution (e.g., oral rinse, throat gargle, eye drop), lotion, cream, ointment, gel, foam, transdermal patch, powder, solid, ponge, tape, vapor, inhalation or intranasal spray (e.g., nasal spray, nasal mists, sinus spray, nebulizer), enema, eye drops), or enterally (e.g., orally, gastric feeding tube, duodenal feeding tube, gastrostomy, rectally, buccally). Inclusion in feed, water or an inhaled formulation is particularly desirable for use with animals. In some embodiments, a compound is formulated so as to allow the soluble polyglucosamine or soluble polyglucosamine derivative thereof to diffuse into a subject upon administration to the subject or to be ingested, inhaled or swabbed while incorporated into a time release formulation.

The compound described herein (e.g., a soluble polyglucosamine or a derivatized (i.e., functionalized) polyglucosamine) can be administered before, during or after the onset of the condition or disorder described herein. For example, the compound described herein can be administered in a subject who has been treated or is being treated with radiation therapy, e.g., other than that related to the treatment of cancer. The methods herein contemplate administration of an effective amount of compound or compound composition to achieve the desired or stated effect. The compounds can be administered as a continuous time-release or ad-libitim in water or food. Such administration can be used as an acute therapy (e.g., short-term treatment). The amount of active ingredient that may be combined with the carrier materials to produce a single dosage form will vary depending upon the subject treated and the particular mode of administration. A typical solution preparation will contain from about 1 μg/mL to about 1000 μg/mL, about 5 μg/mL to about 500 μg/mL, about 10 μg/mL to about 250 μg/mL, about 50 μg/mL to about 200 μg/mL, or about 100 μg/mL to about 200 μg/mL of a compound described herein, e.g., a compound of Formula (I). A typical solid diffusible preparation will contain from about 0.1% to about 10%, about 0.2% to about 10%, or about 0.05% to about 5% by weight of a compound described herein, e.g., a compound of Formula (I). A typical solid dissolvable preparation will contain from about 0.1% to about 95%, about 0.2% to about 70%, about 0.5% to about 40%, about 1% to about 10% by weight of a compound described herein, e.g., a compound of Formula (I).

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the type and nature of the bacteria, the patient's disposition to the disease, condition or symptoms, and the judgment of the treating physician.

In some embodiments, the compounds described herein (e.g., a soluble polyglucosamine or a derivatized (i.e., functionalized) polyglucosamine) can be formulated, e.g., as a solution, gel, ointment, or dressing, e.g., for treating a subject that has been or will be exposed to radiation therapy, e.g., other than that related to the treatment of cancer. In some embodiments, the dosage (e.g., solution dosage) is from about 10 μg/mL to about 1000 μg/mL, about 50 μg/mL to about 500 μg/mL, or about 100 μg/mL to about 300 μg/mL of a compound described herein, e.g., a compound of Formula (I), applied e.g., sufficiently to treat a subject that has been or will be exposed to radiation, trauma or shock. In some embodiments, the dosage (e.g., solution dosage) is from about 10 to about 1000 µg/mL, about 50 µg/mL to about 500 µg/mL, or about 100 µg/mL to about 300 µg/mL of a compound described herein, e.g., a compound of Formula (I), applied e.g., sufficiently to treat a subject that has been or will be exposed to radiation, trauma or shock at least 1, 2, 3, 4, 5 or 6 times daily. In some embodiments, the solid diffusible composition (dressing) is from about 0.1% to about 10%, about 0.2% to about 8%, or about 0.5% to about 5%, by weight of a compound described herein, e.g., a compound of Formula (I), applied e.g., sufficiently to treat a subject that has been or will be exposed to radiation, trauma or shock at least 1, 2, 3, 4, 5 or 6 times daily.

In some embodiments, the compounds described herein (e.g., a soluble polyglucosamine or a derivatized (i.e., functionalized) polyglucosamine) can be formulated, e.g., as a solution, encapsulated time release, gel, or enema, e.g., for treating area a subject that has been or will be exposed to radiation, trauma or shock, e.g., in the mucous membrane, e.g., in the GI tract. In some embodiments, the dosage is from about 10 µg/mL to about 1000 µg/mL, about 20 µg/mL to about 900 µs/mL, about 50 µg/mL to about 500 µg/mL, about 60 µg/mL to about 300 µg/mL, or about 50 to about 200 pg/mL of a compound described herein, e.g., a compound of Formula (I), in solution, e.g., ad libitum, e.g., in water or fluid. In some embodiments, the composition is administered at least 1, 2, 3, or 4 times daily. In some embodiments, the dosage is from about 1 mg/kg to about 200 mg/kg, about 2 mg/kg to about 100 mg/kg, about 4 mg/kg to about 75 mg/kg, or about 5 mg/kg to about 40 mg/kg body weight of a compound described herein, e.g., a compound of Formula (I), in an encapsulated time release, gel, capsule or enema. In some embodiments, the composition is administered at least 1, 2, 3, 4, 5 or 6 times daily.

In some embodiments, the compounds described herein (e.g., a soluble polyglucosamine or a derivatized (i.e., functionalized) polyglucosamine) can be formulated as a nebulized solution or powder, or lavage, e.g., for treating a subject that has been or will be exposed to radiation, trauma or shock, e.g., in respiratory tract. In some embodiments, the dosage is from about 500 µg to about 50000 µg, about 1000 µg to about 25000 µg, about 2000 µg to about 10000 µg, or about 4000 µg to about 6000 µg of a compound described herein, e.g., a compound of Formula (I), per kg body weight, every 2, 4, 6, 8, 10, 12, or 24 hours. In some embodiments, the composition is administered at least 1, 2, 3, 4, 5 or 6 times daily.

In some embodiments, the compounds described herein (e.g., a soluble polyglucosamine or a derivatized (i.e., functionalized) polyglucosamine) can be formulated, e.g., as a spray, ointment, gel or inhalant, e.g., for treating a disorder or condition described herein, e.g., in the GI tract, throat, ear, or nose. In some embodiments, the dosage is from about 10 µg/mL to about 1000 µs/mL, about 20 µg/mL to about 500 µg/mL, about 50 µg/mL to about 300 µg/mL of a compound described herein, e.g., a compound of Formula (I), in solution, about 0.1% to about 10%, about 0.5% to about 5%, or about 1% to about 2%, by weight of a compound described herein, e.g., a compound of Formula (I), in an ointment or gel. In some embodiments, the compound described herein, e.g., a compound of Formula (I), or composition is administered at least 1, 2, 3, 4, 5 or 6 times daily.

In some embodiments, the compounds described herein (e.g., a soluble polyglucosamine or a derivatized (i.e., functionalized) polyglucosamine) can be formulated, e.g., as a solution, or encapsulated time release (e.g., enteric coating), e.g., for treating an inflammatory gastrointestinal disorder, e.g., as described herein. In some embodiments, the dosage is from about 0.1 to about 100 mg/kg body weight, about 1 to about 90 mg/kg body weight, about 10 to about 80 mg/kg body weight, about 20 to about 70 mg/kg body weight, about 30 to about 60 mg/kg body weight, about 0.1 to about 1 mg/kg body weight, about 1 to about 10 mg/kg body weight, about 10 to about 20 mg/kg body weight, about 20 to about 40 mg/kg body weight, about 40 to about 60 mg/kg body weight, about 30 to about 50 mg/kg body weight (e.g., 40 mg/kg body weight), about 60 to about 80 mg/kg body weight, or about 80 to about 100 mg/kg body weight. In some embodiments, the composition is administered at least 1, 2, 3, 4, 5 or 6 times daily.

Course of Treatment

Inventive methods of the present invention contemplate single as well as multiple administrations of a therapeutically effective amount of a composition as described herein. Compounds as described herein, e.g., a compound of Formula (I), can be administered at regular intervals. In some embodiments, a composition described herein is administered in a single dose. In some embodiments, a composition described herein is administered in multiple doses.

In some embodiments, a therapeutically effective amount of a compound as described herein, e.g., a compound of Formula (I), may be administered periodically at regular intervals (e.g., L 2, 3, 4, 5, 6, 7, 8, 9, 10 or more times every 1, 2, 3, 4, 5, or 6 days).

In some embodiments, a compositions described herein is administered at a predetermined interval (e.g., 1, 2, 3, 4, 5, 6, 7, 8, 9, 10 or more times every 1, 2, 3, 4, 5, or 6 days). In some embodiments, a composition is administered once daily. In some embodiments, a composition is administered from about 1 to about 5 times per day. In some embodiments, a composition is administered from about 1 to about 3 times per day.

In some embodiments, the subject is treated for up to 3 weeks (e.g., up to 2 weeks, 1 week, 6 days, 5 days, 4 days, 3 days, 2 days, or 1 day).

In some embodiments, the subject is treated for 3 weeks, 2 weeks, 1 week, 6 days, 5 days, 4 days, 3 days, 2 days, or 1 day.

In some embodiments, the subject is treated within 1 hour, 2 hours, 3 hours, 4 hours, 5 hours, 6 hours, 8 hours, 10 hours, 12 hours, 16 hours, 20 hours, 24 hours, 2 days, 3 days, 4 days, 5 days, 6 days, 1 week, or 2 weeks after exposure to radiation, trauma, or shock.

It should also be understood that a specific dosage and treatment regimen of any particular patient will depend upon a variety of factors, including the activity of the specific compound employed, the age, body weight, general health, diet, time of administration, rate of excretion, drug combination, and the judgment of the treating physician and the severity of the disease or disorder treated. The amount of active ingredients will also depend upon the particular described compound and the presence or absence and the nature of the additional agent in the composition.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Subjects may, however, require intermittent treatment on a long-term basis upon any recurrence of disease symptoms.

Pharmaceutical compositions of this invention comprise a compound described herein, e.g., a compound of Formula (I), or a pharmaceutically acceptable salt thereof; an additional compound including for example, a steroid or an analgesic; and any pharmaceutically acceptable carrier, adjuvant or vehicle. Alternate compositions of this invention comprise a compound described herein, e.g., a compound of Formula (I), or a pharmaceutically acceptable salt thereof; and a pharmaceutically acceptable carrier, adjuvant or vehicle. The compositions delineated herein include a compound described herein, e.g., a compound of Formula (I), as well as additional therapeutic compounds if present, in amounts effective for achieving a modulation of disease or disease symptoms.

The compositions are generally made by methods including the steps of combining a compound described herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, chewing gum, dissolving gel, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

In some cases, the pH of the formulation may be adjusted with pharmaceutically acceptable acids, bases or buffers to enhance the stability of the formulated compound or its delivery form for delivery in particular regions of the body, such as the colon.

When the compositions of this invention comprise a combination of compounds described herein, both the compounds are generally present at dosage levels of between about 0.01 to 100%, and more preferably between about 1 to 95% of the dosage normally administered in a monotherapy regimen. Additionally, combinations of a plurality of compounds described herein are also envisioned. The compounds may be administered separately, as part of a multiple dose regimen, from the compounds of this invention. The compounds may be administered in a manner and dose where they act synergistically, e.g., as described in US Publication No. 2010-0130443, which is incorporated herein by reference in its entirety. Alternatively, those compounds may be part of a single dosage form, mixed together with the compounds of this invention in a single composition.

Kits and Medical Devices

A compound described herein (e.g., a soluble polyglucosamine or a derivatized (i.e., functionalized) polyglucosamine) can be provided in a kit. The kit includes (a) a composition that includes a compound described herein, and, optionally (b) informational material. The informational material can be descriptive, instructional, marketing or other material that relates to the methods described herein and/or the use of the compound described herein for the methods described herein.

The informational material of the kits is not limited in its form. In some embodiments, the informational material can include information about production of the compound, molecular weight of the compound, concentration, date of expiration, batch or production site information, and so forth. In some embodiments, the informational material relates to use of the compound described herein to treat a disorder described herein.

In some embodiments, the informational material can include instructions to administer the compound described herein in a suitable manner to perform the methods described herein, e.g., in a suitable dose, dosage form, or mode of administration (e.g., a dose, dosage form, or mode of administration described herein). In another embodiment, the informational material can include instructions to administer the compound described herein to a suitable subject, e.g., a human, e.g., a human having or at risk for a disorder or condition described herein. For example, the material can include instructions to administer the compound described herein to such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The compound described herein can be provided in any form, e.g., liquid, dried or lyophilized form. It may also be prepared as a capsule, pill, time-release or environment-release (e.g., pH sensitive) capsule or pill. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, dosing bottle, single-unit dosing preparation, pipette, measured spoon, dropper (e.g., eye dropper), swab (e.g., a cotton swab or wooden swab), or any such delivery device.

The composition described herein can be used in a medical device for treating a subject e.g., a mucosal surface of a subject, that has been or will be exposed to radiation, trauma or shock.

EXAMPLES

As provided in the Examples below, PAAG refers to poly(acetyl, arginyl) glucosamine with an average molecular weight of 86 kDa and 30% functionalized unless indicated otherwise. A fraction of the amines of the glucosamine on the polyglucosamine are reacted with a single arginine, as opposed to a dimer, trimer or larger polyarginine. This monoacetylation of each reacted amine is accomplished by using a protecting group on the primary amine of the arginine upon coupling as described in U.S. Pat. No. 8,119,780, the contents of which are incorporated herein by reference.

As shown in the Examples below, in vivo data (e.g., increased survival) suggest improved recovery and reduced morbidity. Furthermore, in vitro data (e.g., down-regulated IL-8) suggest the generation of a less pro-inflammatory environment.

These exemplary results demonstrate that PAAG has the ability to treat and prevent damage resulting from radiation, trauma or shock. Further, it enhances the healing rate of areas that have been exposed to radiation, trauma or shock.

Example 1: Total Body Irradiation Study

Methods

Male mice were exposed to an acute irradiation dose on Day 0 of 0, 12.5, or 13.0 Gy at a rate of 1 Gy/min with lead shielding to the left hind limb. Starting 24 hours after irradiation, the mice were untreated or treated with PAAG or vehicle control, given with 50 mg/kg via oral gavage daily and dosed ad libitum in the drinking water (200 ppm PAAG) from days 1 to 18. The treatment groups are summarized on TABLE 1.

TABLE 1

| Group | Male Mice (n) | Radiation Dose on Day 0 | Treatment | Dosing (p.o.) | Dosing (in drinking water) Days 1-18 | Measure Survival and Body Weight |
|---|---|---|---|---|---|---|
| 1 | 5 | None | None | None | None | Days 0-18 |
| 2 | 5 | None | PAAG 50 mg/kg | q.d. Days 1-18* | PAAG 200 ppm | Days 0-18 |
| 3 | 16 | 12.5 Gy | Vehicle Control | q.d. Days 1-18* | None | Days 0-18 |
| 4 | 16 | 12.5 Gy | PAAG 50 mg/kg | q.d. Days 1-18* | PAAG 200 ppm | Days 0-18 |
| 5 | 16 | 13.0 Gy | Vehicle Control | q.d. Days 1-18* | None | Days 0-18 |
| 6 | 16 | 13.0 Gy | PAAG 50 mg/kg | q.d. Days 1-18* | PAAG 200 ppm | Days 0-18 |

*The first dose was administered 24 hours after irradiation.

PAAG Treatment Reduces Mortality in Mice Dosed with Radiation

Figure 2:
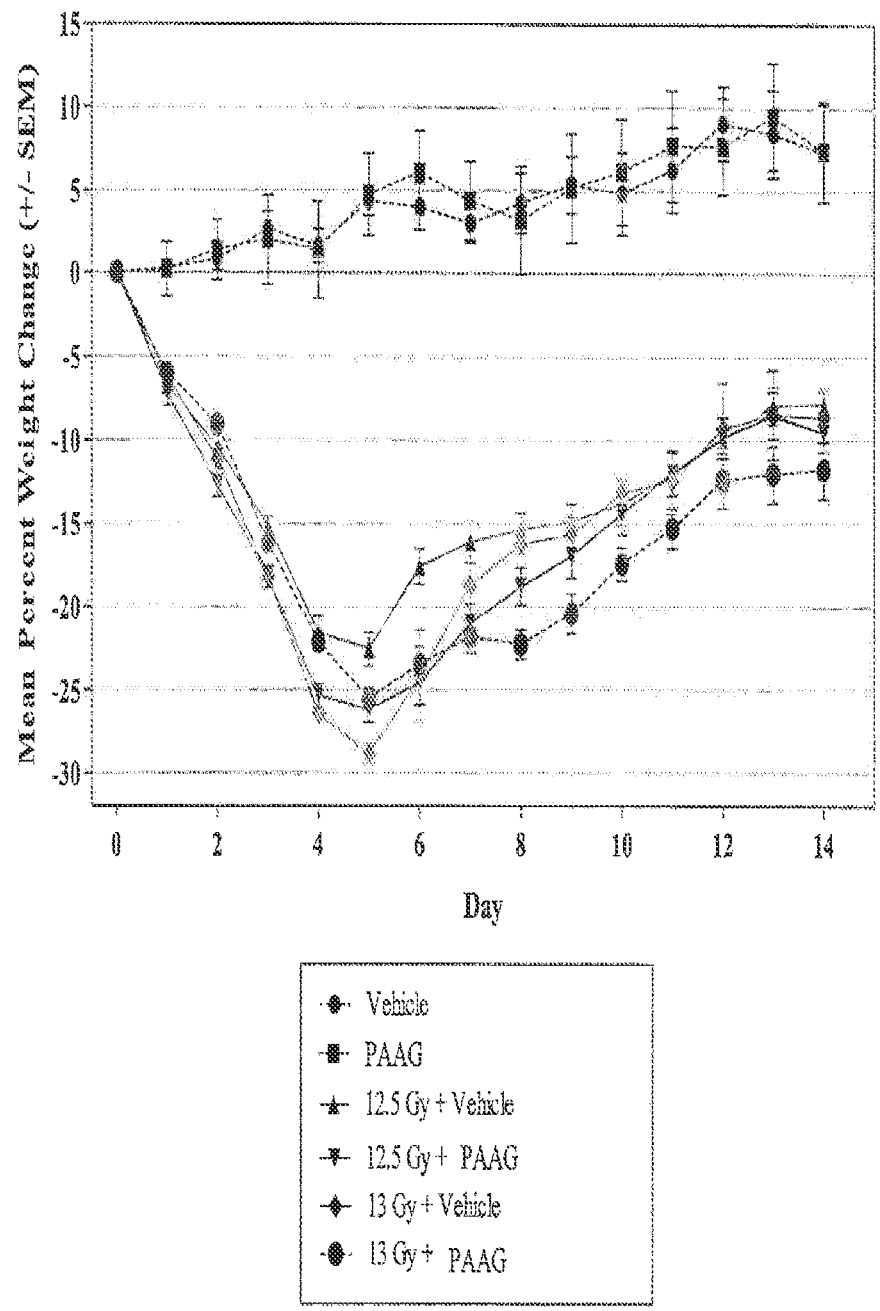
FIG. 2 depicts an exemplary effect of PAAG and radiation treatment on weight.

The total body irradiation study was performed as described above with control vehicle or PAAG (86 kDa and 30% functionalization) administered to the mice at the indicated final concentrations. The results of the study showed a dramatic reduction in mortality for mice exposed to an LD 80 dose of ionizing radiation. As shown in the Kaplan-Meier Survival Plot in FIG. 1, there was no mortality in animals that were not irradiated. No statistical difference was observed between the treated and untreated groups exposed to 12.5Gy of radiation (p=0.081), an LD 20. However, a very significant (p<0.0001) difference was observed in the LD 80 dose in mice given vehicle as compared to PAAG. In fact, 88% of the treated animals survived while only 19% of the untreated animals survived. As shown in FIG. 2, the corresponding plot of the mean percent weight change shows PAAG has no significant effect on weight change in animals as compared with untreated animals. The comparative mortality data from these experiments is tabulated on TABLE 2.

TABLE 2

| Group | Radiation | Treatment | Mice per Group (n) | No. of Death | Day of Death | Observation/ Action† | Percent Dead Per Group |
|---|---|---|---|---|---|---|---|
| 1 | None | None | None | 0 | — | — | 0 |
| 2 | None | Chitosan-Arginine | 5 | 0 | — | — | 0 |
| 3 | 12.5 Gy | Vehicle Control | 16 | 1 | Day 6 | Euthanized | 6.25 |
| 4 | 12.5 Gy | Chitosan-Arginine | 16 | 1 | Day 5 | Euthanized | 31.25 |
|  |  |  |  | 1 | Day 6 | Euthanized |  |
|  |  |  |  | 3 | Day 7 | Euthanized |  |
| 5 | 13.0 Gy | Vehicle Control | 16 | 2 | Day 5 | Euthanized | 81.25 |
|  |  |  |  | 5 | Day 6 | Euthanized |  |
|  |  |  |  | 5 | Day 6 | Found dead |  |
|  |  |  |  | 1 | Day 7 | Euthanized |  |
| 6 | 13.0 Gy | Chitosan-Arginine | 15* | 1 | Day 6 | Found dead | 13.33¶ |
|  |  |  |  | 1 | Day 18 | Euthanized |  |

*Group 6 had 1 animal excluded from analysis as a result of non-treatment related euthanasia due to oral gavage injury.
†Euthanasia due to moribund or body weight loss >30% from baseline.
¶Based on n = 15.

Example 2: Mucosal Radiation Dose Ranging Study

Methods

In a dose ranging study, an acute dose of irradiation of 40 Gy directed to the left buccal cheek pouch of Syrian Golden hamsters and the hamsters were treated t.i.d. with 50, 100, 250 and 500 µg/mL PAAG or vehicle control directly inserted into the pouch. Mean % weight change and mucositis score were recorded.

PAAG Modulated the Course of Oral Mucositis

Figure 3:
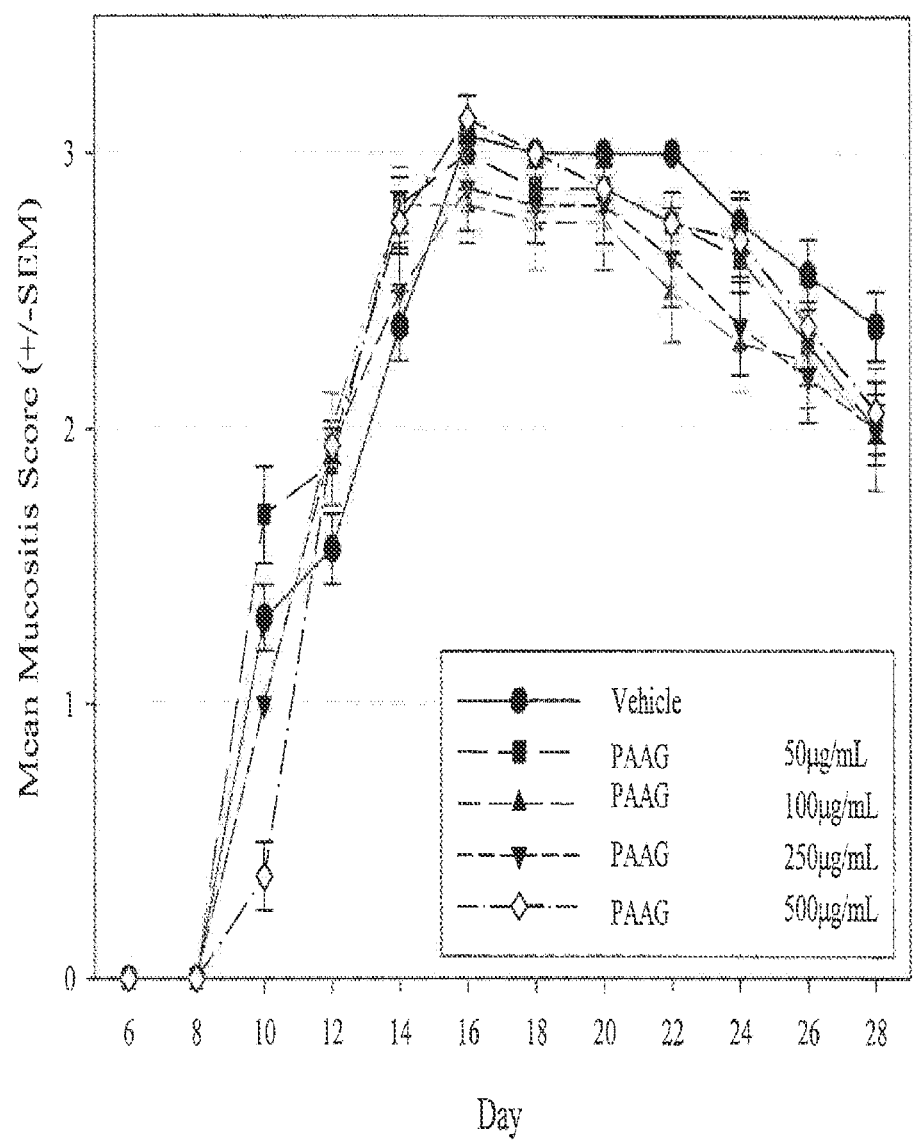
FIG. 3 depicts an exemplary comparison of mean oral mucositis scores for a vehicle control and four doses of PAAG.
Figure 4:
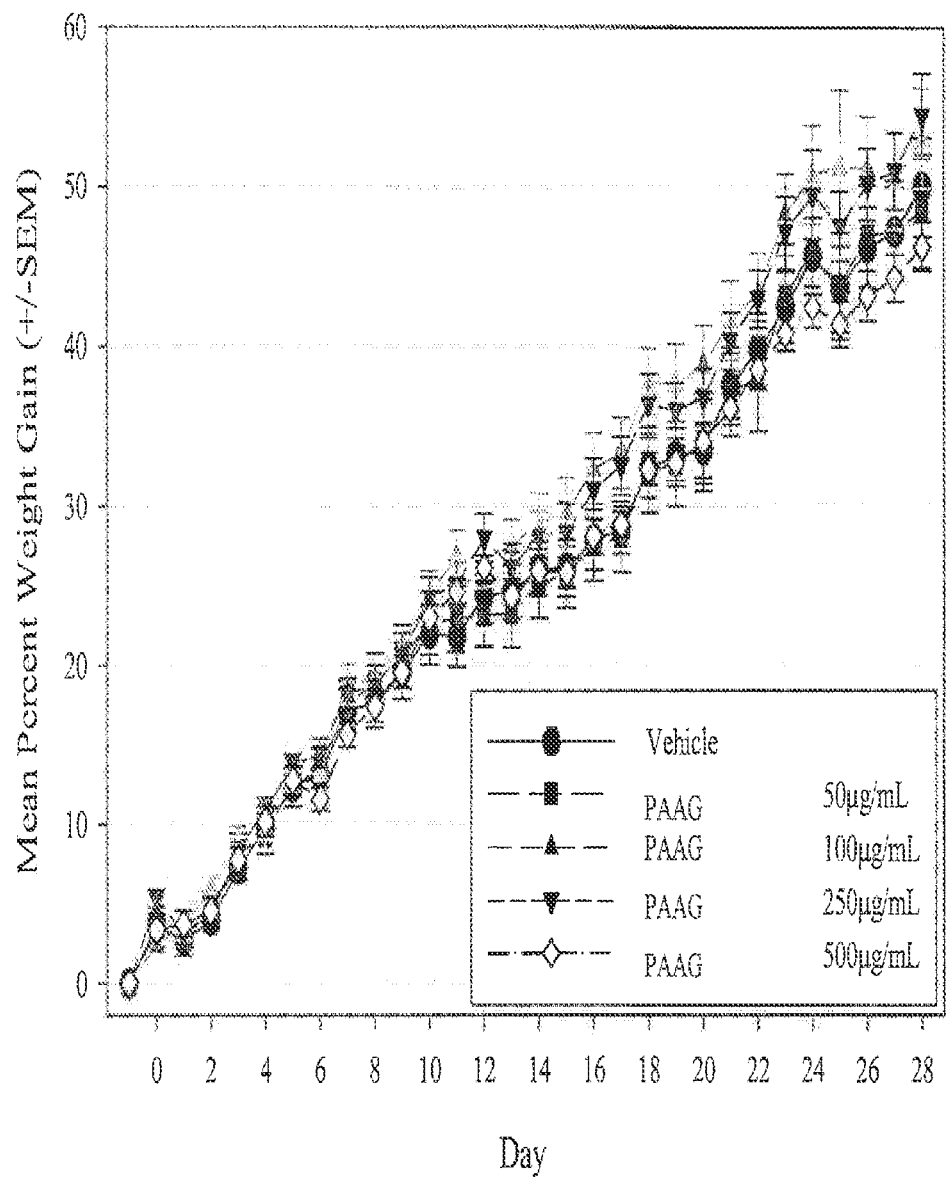
FIG. 4 depicts an exemplary comparison of weight change for a vehicle control and four doses of PAAG given as an oral rinse.
Figure 5:
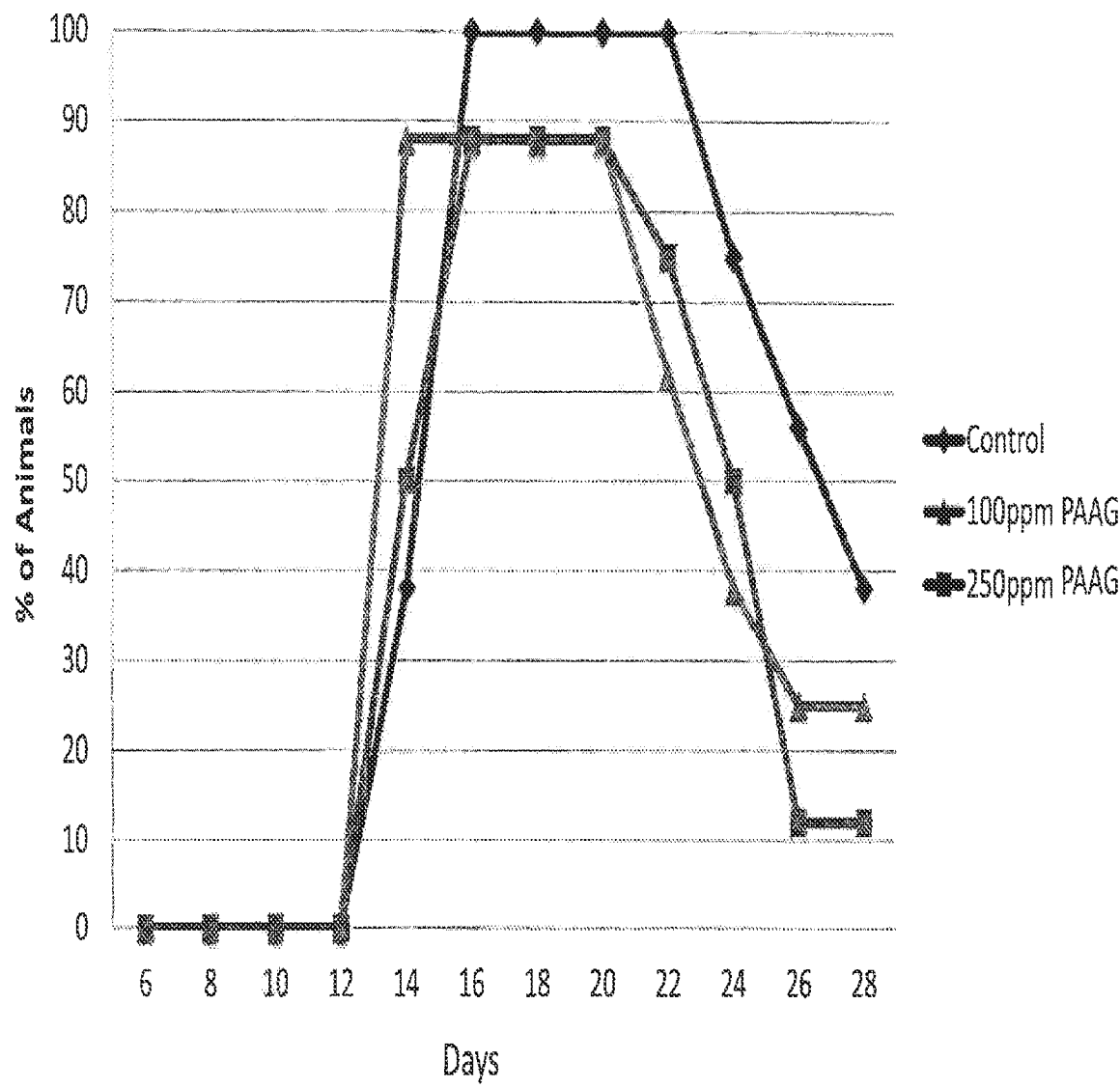
FIG. 5 depicts an exemplary comparison of the percentage of animals with an oral mucositis score of 3 or higher on a given day post irradiation for a vehicle control and two doses of PAAG.
Figure 6:
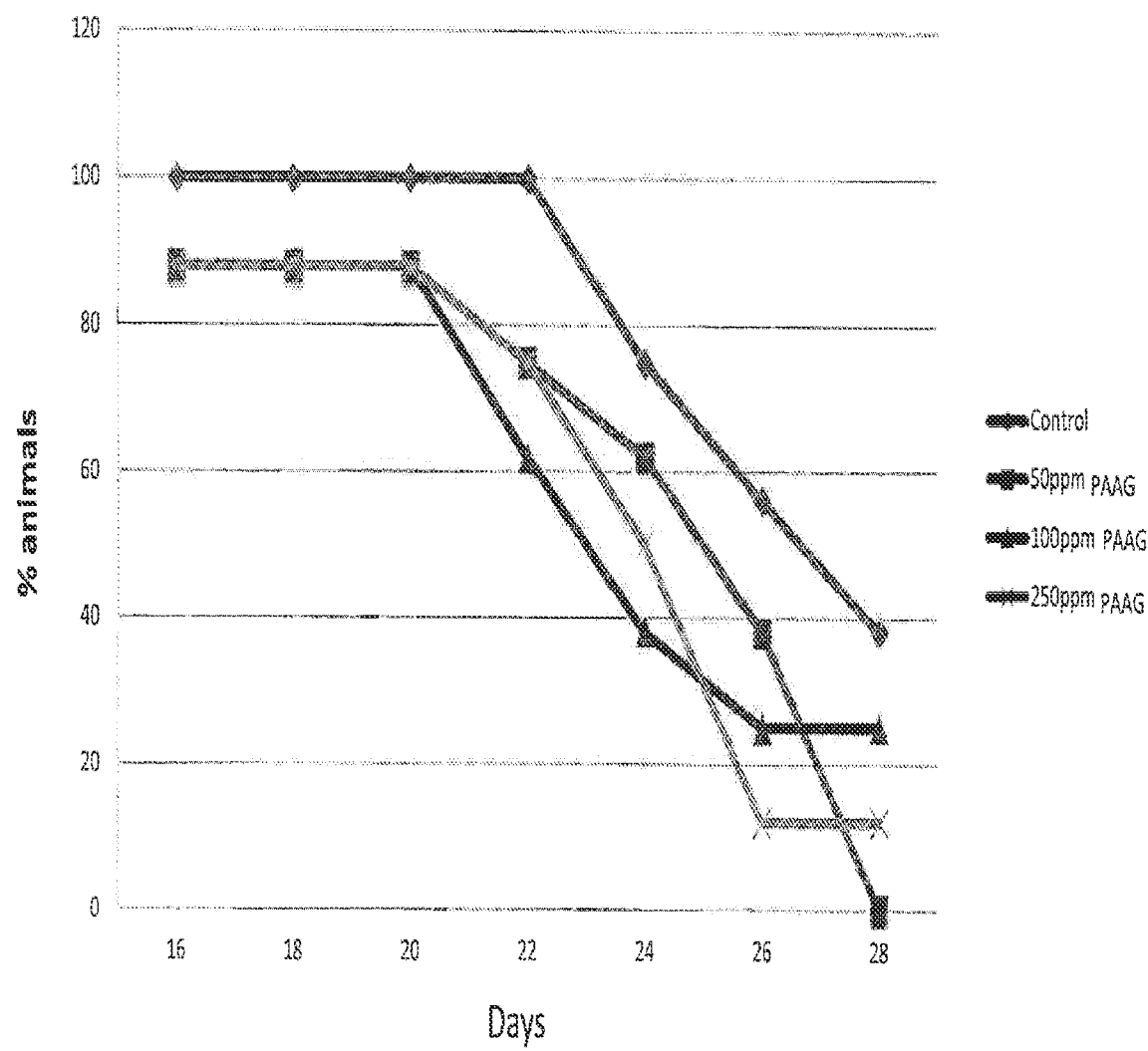
FIG. 6 depicts an exemplary comparison of the percentage of animals with a mucositis score of 3 or higher on a given day post irradiation for a vehicle control and three doses of PAAG.

The mucosal radiation dose ranging study was performed as described above with PAAG (86 kDa and 30% functionalization) added to the indicated final concentrations. Comparison of the mean mucositis scores for a vehicle control and four doses of PAAG are shown in FIG. 3. Consistent with its attenuation of chemically-induced intestinal injury (data not shown), PAAG modulated the course of oral mucositis. A comparison of the mean percent weight gain for mice dosed with vehicle control and four dosing concentrations of PAAG is shown in FIG. 4. Percent ulceration as shown by a plot of the percent of animals with a mucositis score of 3 or higher on a given day post irradiation for a vehicle control and two doses of PAAG is shown in FIG. 5. The healing effect of PAAG is shown in FIG. 6, which depicts the comparison of the percentage of animals with a mucositis score of 3 or higher on a given day post irradiation for a vehicle control and three doses of PAAG.

Example 3: Oral Mucositis Scheduling Study

Methods

In a scheduling study, an acute dose of irradiation of 40 Gy directed to the left buccal cheek pouch and the hamsters were treated t.i.d. with 200 µg/mL PAAG or vehicle control directly inserted into the pouch. Schedules included PAAG treatment Day −7 to 36, Day −1 to 36, Day −1 to 14, and Day 10-36. Mean % weight change and mucositis score were recorded.

Optimization of Scheduling

Figure 7:
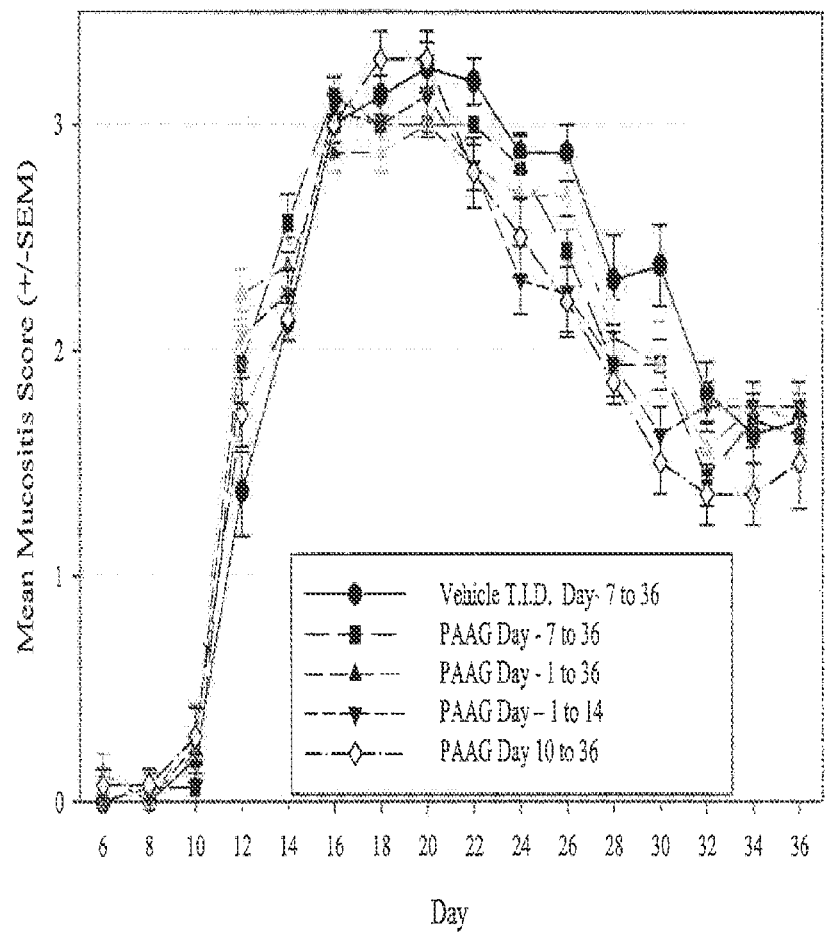
FIG. 7 depicts an exemplary comparison of the mean mucositis scores for a vehicle control and 200 ppm PAAG administered thrice daily at four different time windows.
Figure 8:
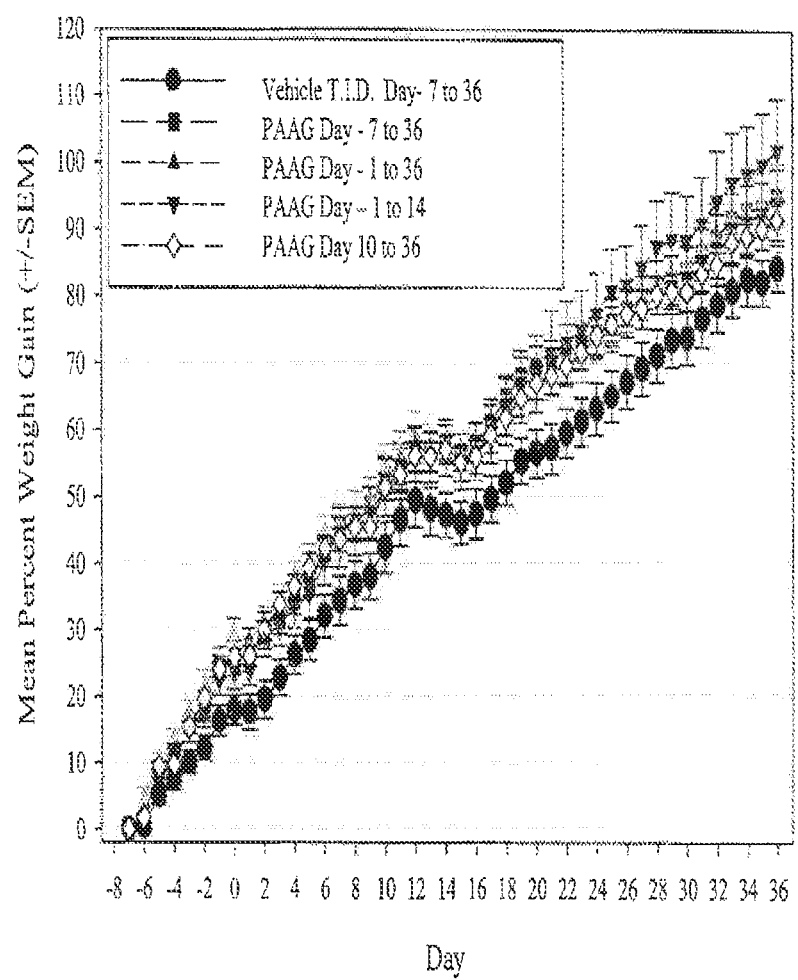
FIG. 8 depicts an exemplary comparison of the mean percent weight gain for a vehicle control and 200 ppm PAAG administered thrice daily at four different scheduling windows.
Figure 9:
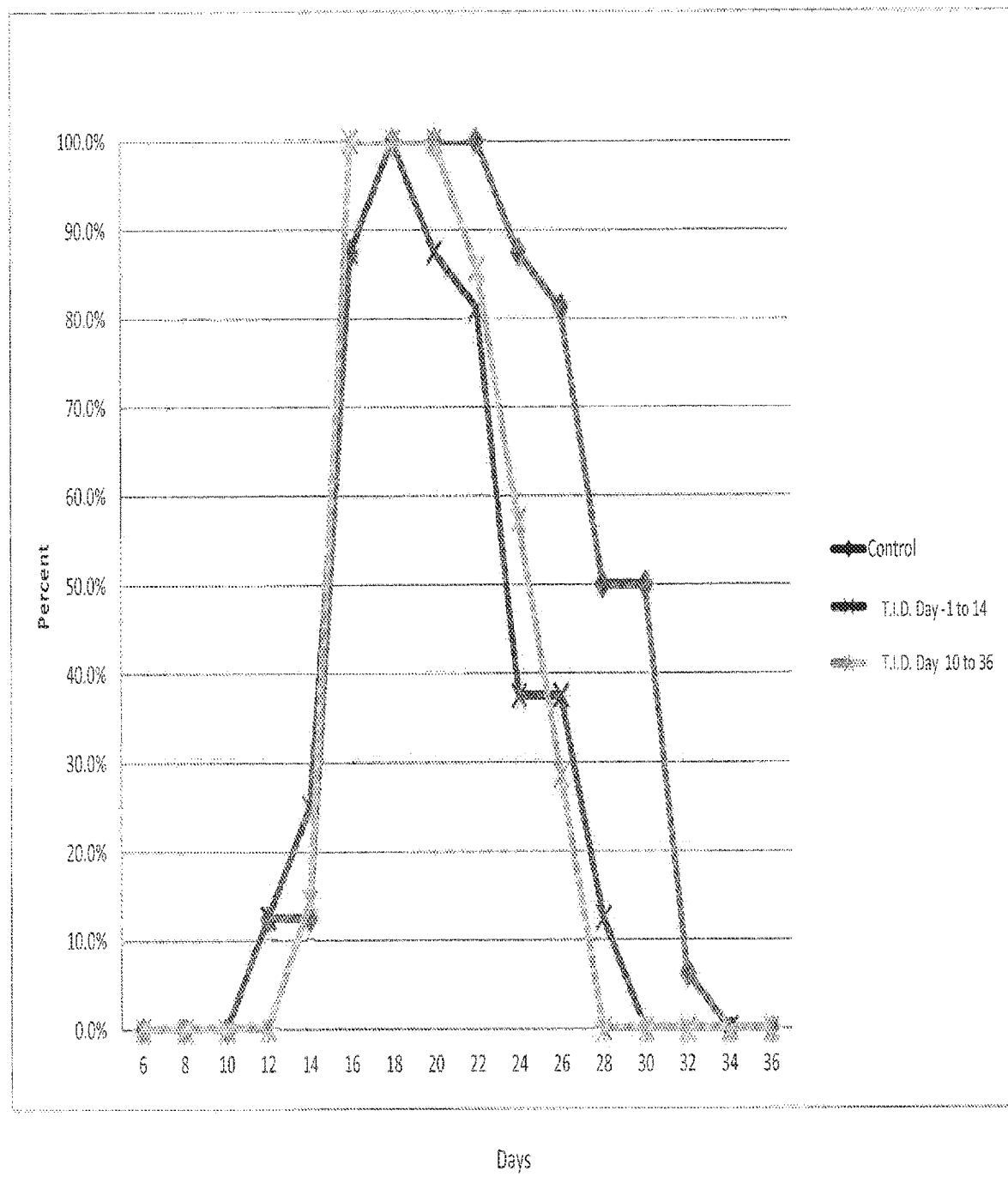
FIG. 9 depicts an exemplary comparison of the percentage of animals with a score of 3 or greater for a vehicle control and 200 ppm PAAG administered thrice daily at two different scheduling windows.

Oral mucositis scheduling study was performed as described above with PAAG (86 kDa and 30% functionalization) added to the indicated final concentrations. The mean mucositis scores for a vehicle control and 200 ppm PAAG administered thrice daily from Day −7 to 36, Day −1 to 36, Day −1 to 14, or Day 10 to 36 is shown in FIG. 7. A comparison of the mean percent weight gain for mice dosed with vehicle control and 200 ppm PAAG from Day −7 to 36, Day −1 to 36, Day −1 to 14, or Day 10 to 36 is shown in FIG. 8. Mice dosed with 200 ppm PAAG administered thrice daily from Day −1 to 14 or from Day 10 to 36 have a reduced mean mucositis score relative to mice dosed with 200 ppm PAAG thrice daily from Day −7 to 36 or from Day −1 to 36. Shown in FIG. 9 is a comparison of the percentage of animals with a score of 3 or greater in mice dosed with a vehicle control and those dosed with 200 ppm PAAG administered thrice daily at Day −1 to 14 and Day 10 to 36.

Example 4: IL-8 Production Response Study

Methods

The human myeloid cell line (U937) was propagated in RPMI 1640 supplemented with 10% (v/v) fetal bovine serum and 2 mm L-glutamine. Cells were seeded at $6 \times 10^5$ cells per well in 24 well plates in RPMI 1640 additionally supplemented with 0.1 ug PMA for 48 hours to activate U937 cells to be macrophage-like. Cell media was replaced with media without fetal bovine serum and PMA for at least 2 hours. The duration of pretreatments of Lactoferrin (100 ng/ml), and PAAG (200 ug/ml) was one hour before cells and media being rinsed twice with D-PBS. Cells were then subjected to media containing LPS (10 ng/ml) for IL-8 stimulation. Supernatants were extracted and stored after 4 hours from the time of LPS stimulation. An IL-8 ELISA was performed according to the BioLegend protocol to measure IL-8 production.

Figure 10:
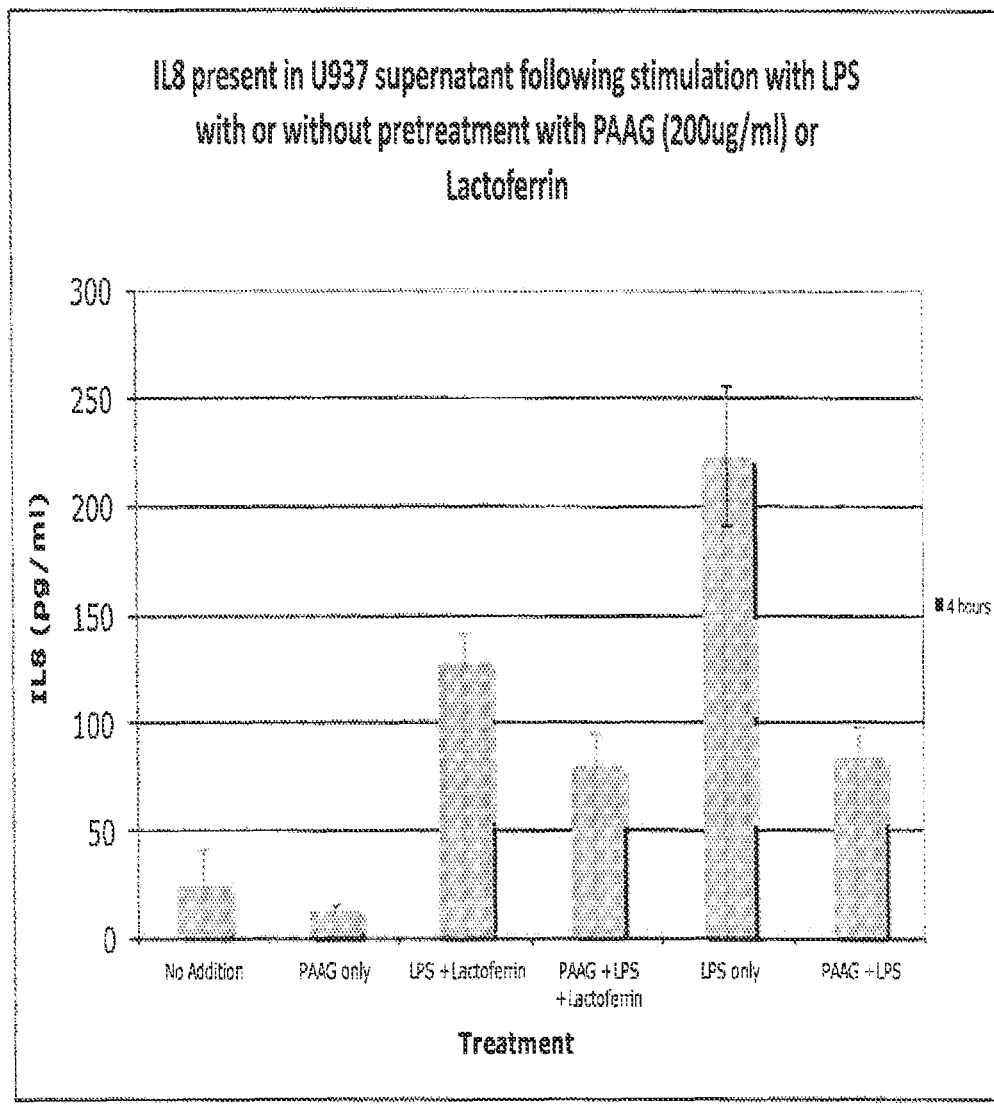
FIG. 10 depicts an exemplary comparison of the production of IL8 in U937 cells following stimulation with LPS with or without pretreatment with 100 ppm PAAG or lactoferrin.

Production of I-L8 in U937 Cells Following Stimulation with LPS is Reduced when Pretreated with 100 ppm PAAG IL-8 production was performed as described, with PAAG (86 kDa and 30% functionalization), LPS, and Lactoferrin added to the indicated final concentrations prior to rinsing and activation by LPS. As shown in FIG. 10, pretreatment with PAAG reduced the LPS activated IL-8 response relative to the response pretreated with control or lactoferrin.

Example 5: Nasal Epithelium/MRSA Binding Assays

Methods

Figure 11:
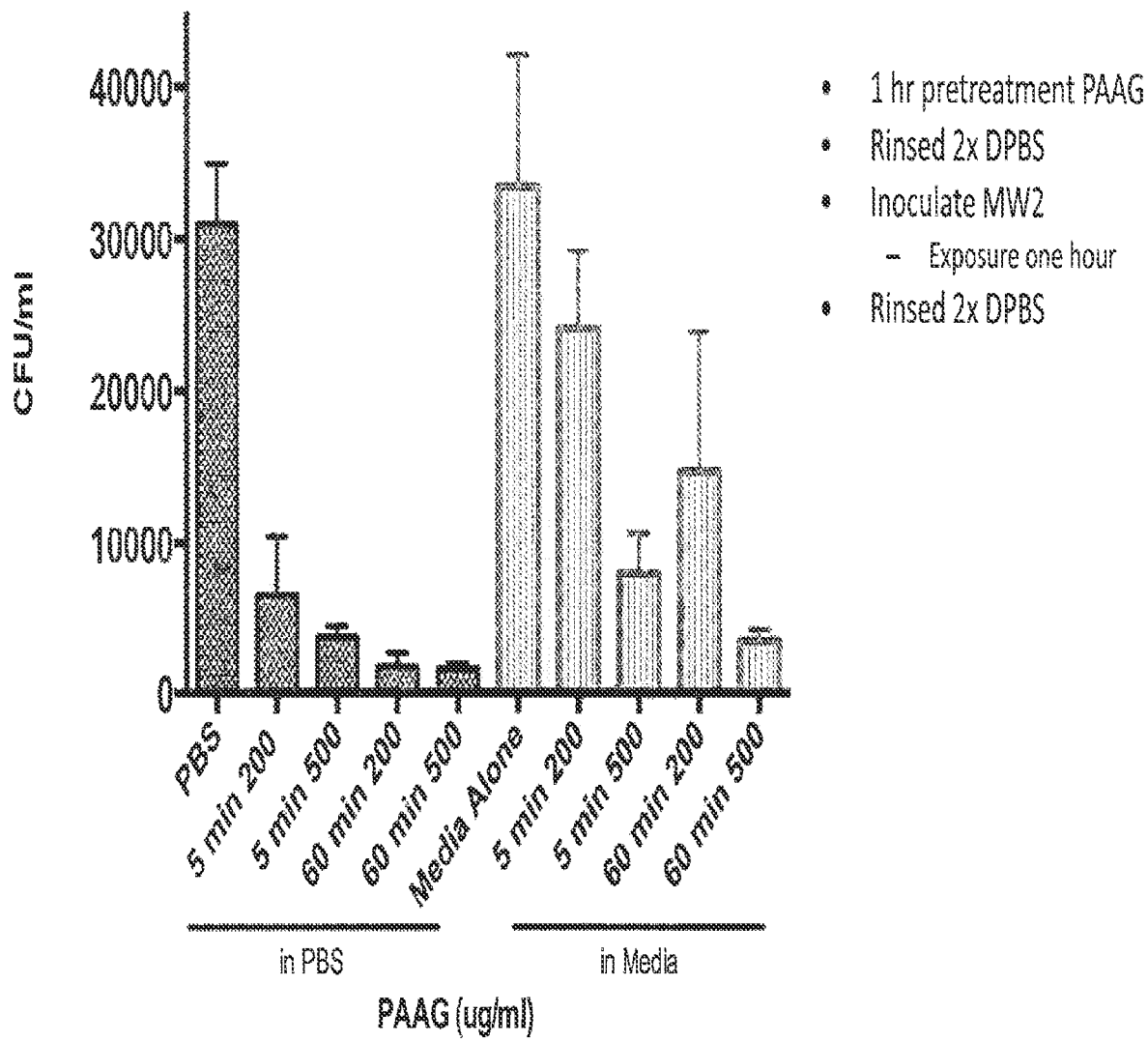
FIG. 11 depicts an exemplary comparison of binding of MRSA to nasal epithelial cells following pretreatment with media, 200 or 500 ppm PAAG.

The nasal epithelium cell line (RPMI-2650) were grown in Eagle's Minimal Essential Media (EMEM) supplemented with 10% (v/v) fetal bovine serum and 2 mm L-glutamine. RPMI 2650 cells were seeded at $2.5 \times 10^5$ per well in 24 well plates and incubated at 37° C. and in atmosphere of 5% $CO_2$ for 24 hours. The cells were then rinsed twice with D-PBS and replaced with (EMEM) without fetal bovine serum for another 24 hours. An overnight culture of MRSA strain MW2 (ATCC BAA-1707) using LB-broth was grown 24 hours before inoculation. PAAG (86 kDa and 30% functionalization) was dissolved in either EMEM without fetal bovine serum or D-PBS in their respective concentrations for pretreatment. Pretreatment of PAAG consisted of rinsing cells of prior cell culture media with D-PBS once and adding media with 200 or 500 ppm PAAG for either 5 min or one hour and with 200 or 500 ppm PAAG. Upon completion of pretreatment, cells were rinsed twice with D-PBS to remove any non-adherent PAAG and inoculated with MW2 in growth phase at an MOI of 1:100 for one hour. Cells were then rinsed twice with D-PBS before being lysed using 0.5% Triton X-100 in D-PBS. Supernatants were extracted and serially diluted, plated and counted for bacterial attachment. Pretreatment of PAAG Decreases Binding of MRSA to Nasal Epithelial Cells Pretreatment and binding studies were performed as described above, with the PAAG added to the indicated final concentrations. As shown on FIG. 11, pretreatment of cells with 200 or 500 ppm PAAG for 5 and 60 minutes decreases binding of MRSA to nasal epithelial cells as compared to PBS and media controls.

Example 6: Bacterial Attachment or Invasion Study

Methods

Caco2 Attachment.

The gut epithelium cell line (Caco2) were grown in Eagle's Minimal Essential Media (EMEM) supplemented with 10% (v/v) fetal bovine serum and 2 mm L-glutamine. Caco2 cells were seeded at $2.5 \times 10^5$ per well in 24 well plates and incubated at 37° C. and in atmosphere of 5% $CO_2$ for 24 hours to confluency. The cells were then rinsed twice with D-PBS and replaced with (EMEM) without fetal bovine serum for another 24 hours. Cells were rinsed with D-PBS twice and replaced with media containing no fetal bovine serum. Pretreatment of the cells with PAAG 200 ug/ml (86 kDa, 30% functionalization; 37 kDa, 22% functionalization; and 27 kDa, 21% functionalization) dissolved in media without serum for one hour was performed and the cells were then rinsed twice with D-PBS to remove any non-adherent PAAG. After rinsing, the cells were inoculated with *Acinetobacter baumaunii* in growth phase at a multiplicity of infection (MOI) of 1:100 for one hour. Cells were then rinsed twice with D-PBS before being lysed using 0.5% Triton X-100 in D-PBS. Supernatants were extracted and serially diluted, plated and counted for bacterial attachment.

*Burkholderia cepacia* Macrophage Uptake.

The myeloid cell line (U937) were grown in RPMI 1640 supplemented with 10% (v/v) fetal bovine serum and 2 mm L-glutamine. Cells were seeded at $6 \times 10^5$ cells per well in 24 well plates in RPMI 1640 additionally supplemented with 0.1 ug PMA for 48 hours to activate U937 cells to be macrophage-like. Cell media was replaced with cell media without fetal bovine serum and PMA for at least 2 hours. Treatments consisted of either PAAG (200 ug/ml) treated on cells for one hour and being rinsed with D-PBS twice before inoculation or with PAAG treatment with no rinse. Upon completion of pretreatment with PAAG, cells were inoculated with *Burkholderia cepacia* in growth phase with an MOI of 1:10 for 45 min. After inoculation period media is supplemented with 50 ug/ml of gentamicin for another 45 min. Cells were then rinsed twice with D-PBS before being lysed using 0.5% Triton X-100 in D-PBS and serially diluted, plated and counted for bacterial uptake.

Results

Figure 12A:
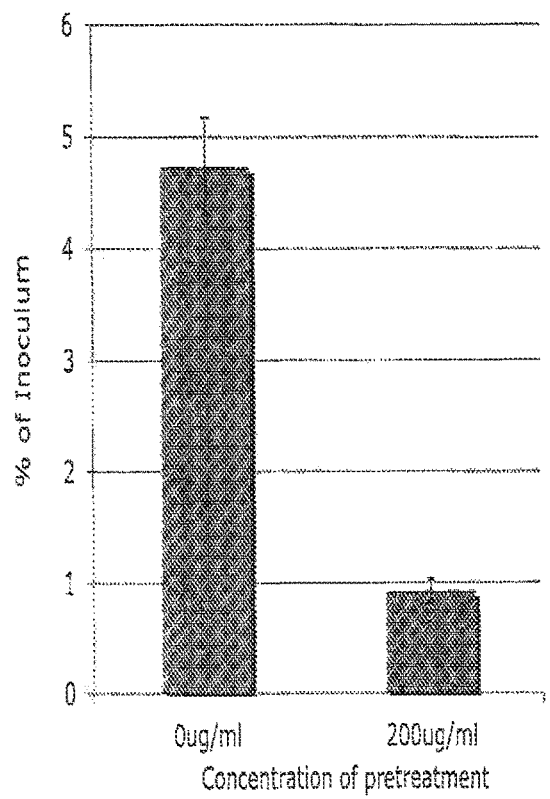
FIG. 12A depicts an exemplary comparison of attachment of *Acinetobacter baumannii* into CaCo2 cells following various pretreatments of the cells by vehicle or 200 ppm PAAG.

Pretreatment and binding studies were performed as described above for Caco2 cells with *Acinetobacter* attachment and *Burkholderia cepacia* macrophage uptake studies, with the PAAG (86 kDa and 30% functionalization) added to the indicated final concentrations. As shown in FIG. 12A, pretreatment of Caco2 cells with 200 μg/mL PAAG decreases the percentage of bacteria bound to Caco2 cells relative to untreated cells, as measured by inoculum present in extracted supernatant.

Figure 12B:
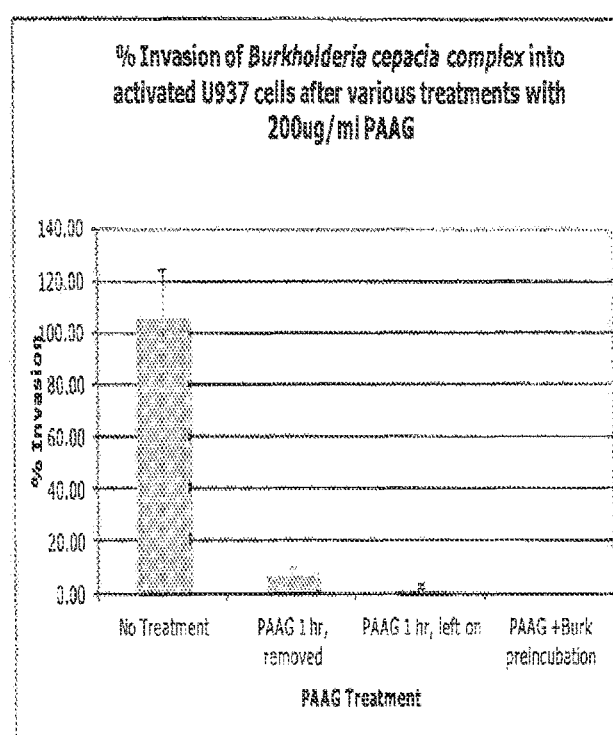
FIG. 12B depicts the comparison of invasion of *Burkholderia cepacia* complex into CaCo2 cells following various pretreatments of the cells by vehicle or 200 ppm PAAG.

As shown in FIG. 12B, pretreatment of the myeloid cell line (U937) with 200 μg/mL PAAG decreases the percentage of bacterial invasion by *Burkholderia cepacia* relative to untreated cells.

Figure 13:
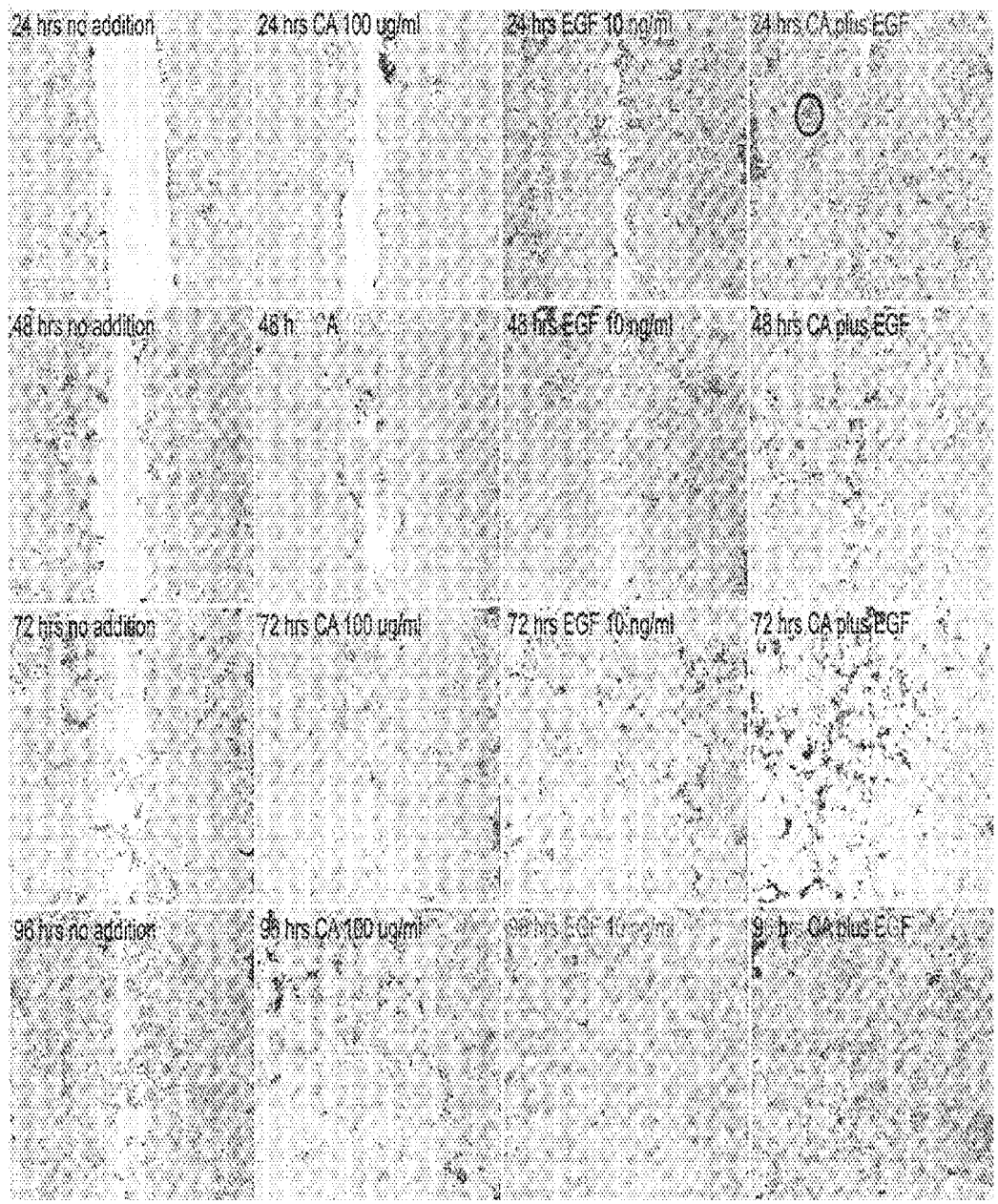
FIG. 13 depicts exemplary A431 epidermal cells, scratched and treated for 24, 48, 72 or 96 hours with nothing, PAAG (here noted as CA), EGF or PAAG (CA)+EGF. The circle on top right is a bubble.

Example 7: Examination of Protective Effect of PAAG on Damaged Epithelial Cells Methods A431 epidermal cells were seeded into 4-well chamber slides in DMEM plus 10% FBS at a density to be confluent the next day ($5 \times 10^5$/well (~1.8 $cm^2$)). The following day, a scratch was made across the confluent monolayer using a sterile 10 μl tip. The medium was aspirated and the wells rinsed with DMEM to remove floating debris. Serum free DMEM was added to all wells, plus or minus PAAG (18 kD, 25% functionalization) or EGF as a positive control. Cells were treated for 24, 48, 72 or 96 hours. Cells were fixed with paraformaldehyde at the indicated times and stained with hematoxylin for better visualization. A representative scratch at time 0 is duplicated at the top of each column of treatments for comparison depicted in FIG. 13.

Results

Scratches "heal" faster than control with either the PAAG or EGF. The combination of PAAG and EGF together resulted in even faster healing, suggesting that PAAG works with EGF to enhance cellular EGF activity. This observation has been reproduced in a number of different cell lines and in in vivo animal models of mucosal damage. Interestingly, this effect is not observed in subconfluent or non-damaged monolayers.

Example 8: Necrotic Enteritis Model Poultry Study of Mortality

Methods

In a lethal necrotic enteritis model poultry study of over 1000 birds, PAAG was given orally in the drinking water to chicks infected with *Clostridium perfringens* (CP) after sensitization by coccidia. Doses of PAAG (22 kD, 36% functionalization) in water ad libitum were given 1 day prior to CP infection and for 5 days post infection. Mortality was assessed 14 days after infection.

Results

Figure 14:
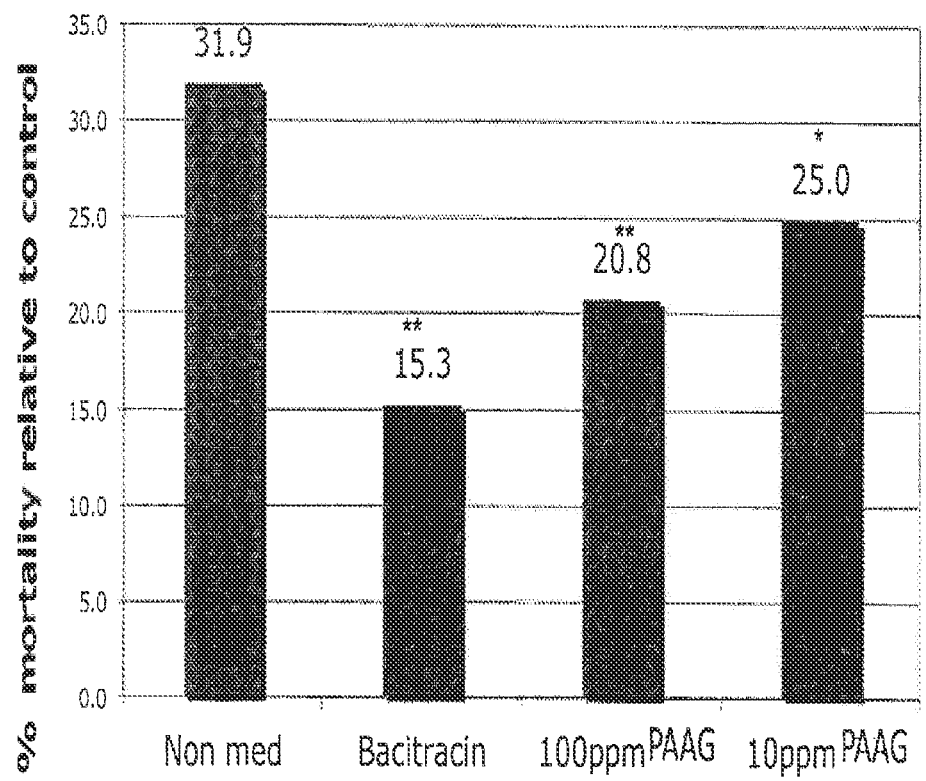
FIG. 14 depicts an exemplary necrotic enteritis model of pathogenic infection showing % mortality of chicks 14 days after exposure to lethal doses of *C. perfringens* with coccidian sensitization. Bacitracin and 100 ppm PAAG delivered ad libitum in water reduced mortality with statistical significance relative to control. 10 ppm was numerically significant vs. control.
Figure 15:
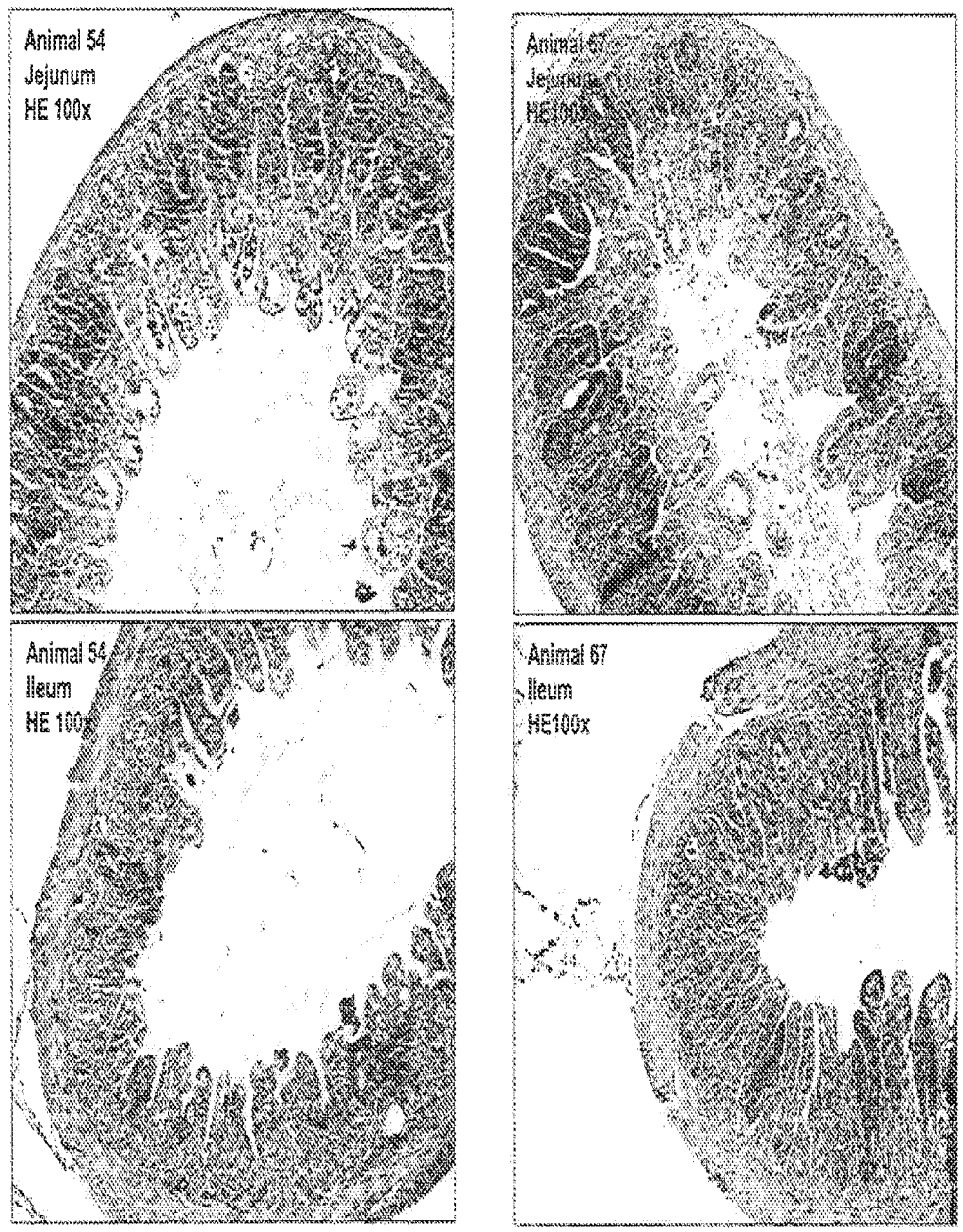
FIG. 15 depicts exemplary photomicrographs of selected mice at 4 days post-irradiation, with 13 Gy-radiation without treatment (Animal 54) and with PAAG treatment (Animal 67).

While 32% of the control animals died, only 15% of the treated animals died as shown in FIG. 14. Bacitracin and 100 ppm PAAG delivered ad libitum in water reduced morality with statistical significance relative to control. 10 ppm was numerically insignificant versus control.

Example 9: Evaluation of PAAG-Mediated Radioprotection on Intestinal Bacterial Translocation in C57BL/6 Mice Study Design Seventy two C57BL/6 mice were enrolled in this experiment. Mice were randomized into four groups of eighteen animals each: non-irradiated controls and active PAAG, irradiated control and active PAAG. On day 0, mice in groups 3 and 4 were exposed to 13.0 Gy radiation at a rate of 1.0 Gy/min (with 5% long bone protection). Mice were treated according to TABLE 3. PAAG (50 mg/kg) or vehicle was administered in drinking water. Six animals were euthanized at 2, 3, and 4 days after radiation exposure, and the ileum and jejunum were fixed then analyzed by a pathologist blinded to the sample identification. At the time of euthanasia, their small intestines were removed, flushed with saline, and divided into three segments. The most proximal 5 cm from the first segment, middle 7 cm from the middle segment, and distal 5 cm from the third segment were removed, flushed with saline, and the middle 3 cm from each excised and snap frozen. Remaining tissue was placed in 10% neutral buffered formalin for histology. The mesenteric lymph nodes (MLN) were also collected from all the animals and assessed as the full 6 animal sample set for total bacterial count at day 4.

TABLE 3

| Group | Radiation Dose | Treatment | Route | Euthanasia Time points | N at Each Time Point |
|---|---|---|---|---|---|
| 1 | n/a | n/a | n/a | Days 2, 3, 4 | 6 |
| 2 | n/a | PAAG 50 mg/kg | PO | Days 2, 3, 4 | 6 |
| 3 | 13.0 Gy | Vehicle | PO | Days 2, 3, 4 | 6 |
| 4 | 13.0 Gy | PAAG 50 mg/kg | PO | Days 2, 3, 4 | 6 |

Tissue Examination

Small intestinal segments were removed at necropsy and fixed as described above. Tissues were embedded in paraffin, sectioned at 5 microns, and stained with hematoxylin and eosin (HE) and gram stain. Slides were evaluated for 4 parameters by a board certified veterinary pathologist as below.

The % of epithelial loss was estimated to the nearest 10%. Inflammation, crypt loss, and crypt regeneration were scored on a scale of 0-4 where 0=no change, 1=mild change, 2=moderate change, 3=marked change, and 4=severe change.

Results

FIGS. 15-27 depict the data generated for the study. In all graphs bars represent group means with standard errors shown. Statistical analysis was performed using GraphPad Prism software and statistical significance is noted in the chart and/or tables when appropriate.

Figure 16:
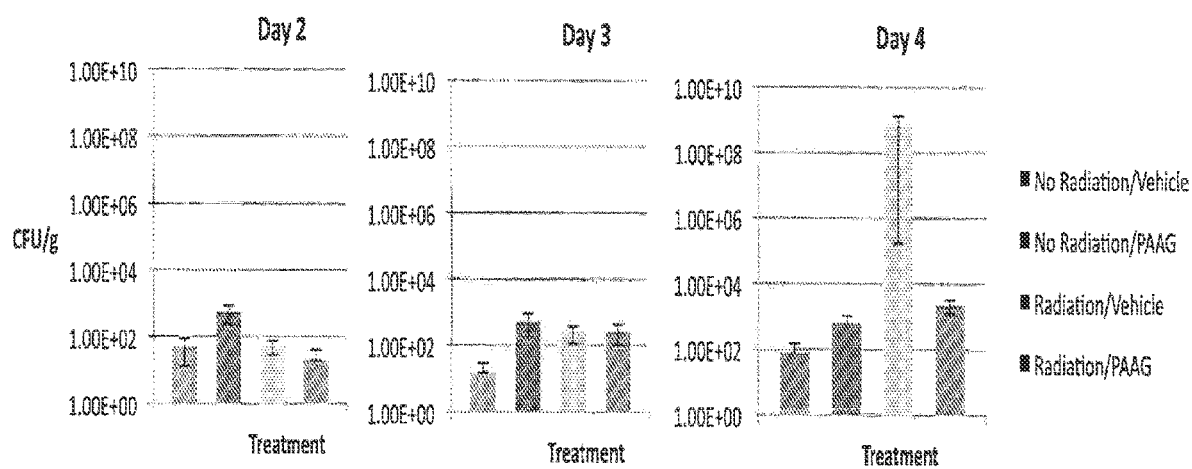
FIG. 16 depicts exemplary total bacterial colony forming units (CFU) per gram of mesenteric lymph nodes in control or irradiated mice treated with vehicle or PAAG once per day via oral gavage at day 2, 3 and 4 starting 24 hours after TBI.
Figure 17:
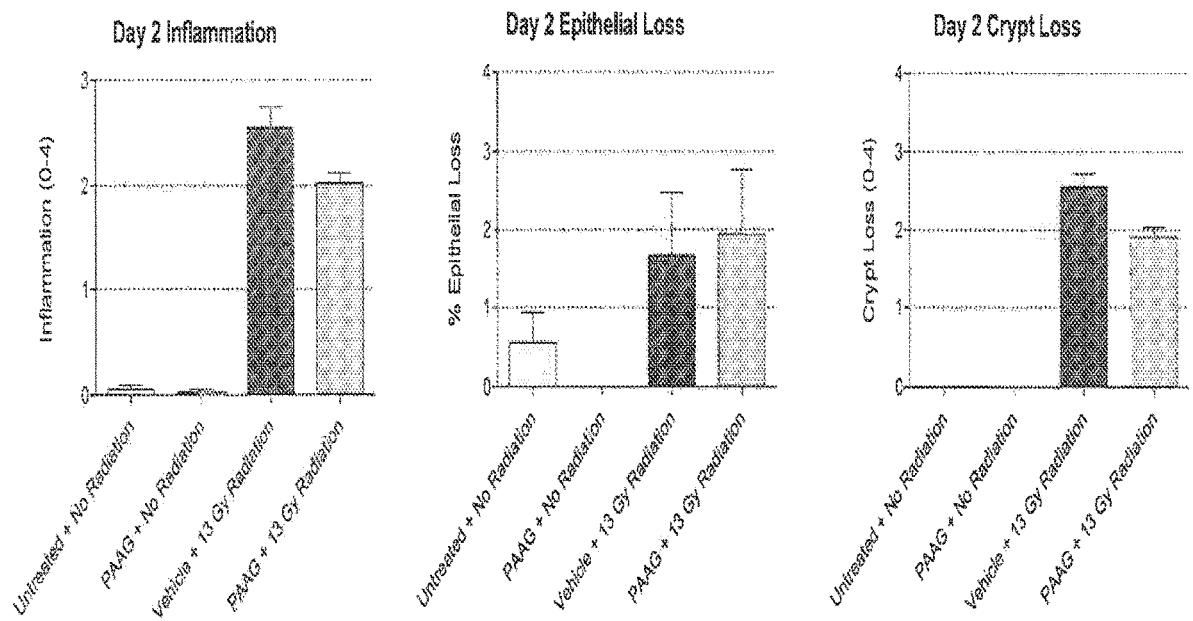
FIG. 17 depicts exemplary inflammation, epithelial loss, crypt loss, and crypt regeneration on day 2
Figure 18:
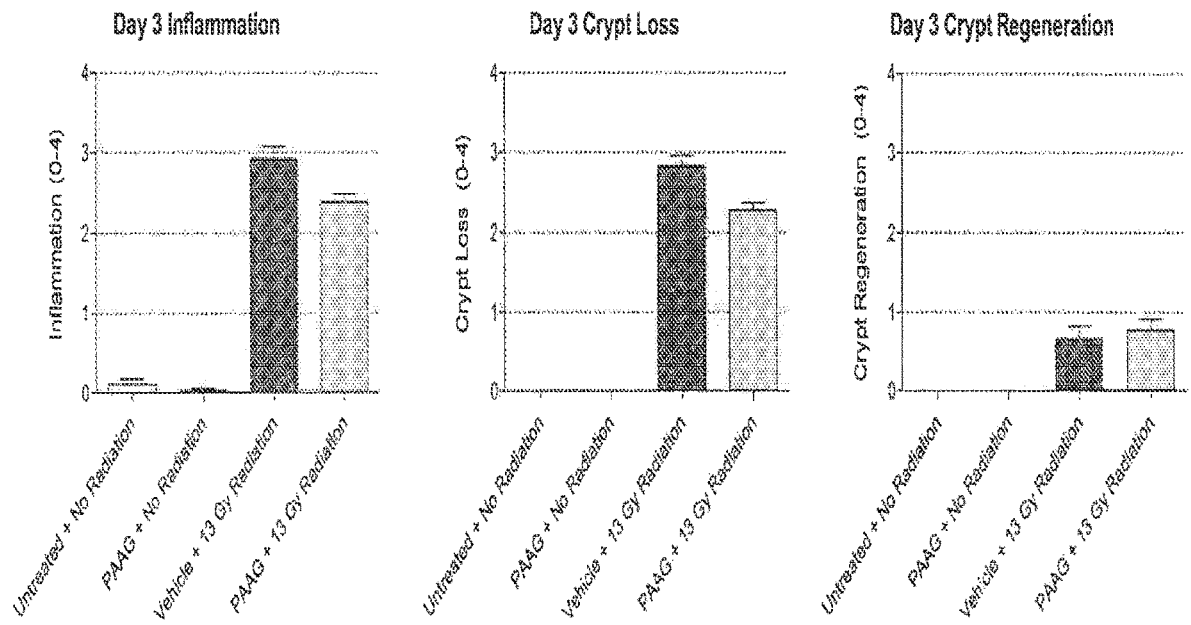
FIG. 18 depicts exemplary inflammation, crypt loss, and crypt regeneration on day 3.

PAAG treatment partially protected C57BL/6 mice from the gastrointestinal effects of total body irradiation. Irradiated, vehicle-treated mice had marked crypt degeneration evident from 2-4 days post-irradiation. Crypt degeneration was associated with inflammation progressing from acute to chronic over the course of the experiment. Without crypt epithelial cells to replenish villous epithelium, villi became progressively shorter and were lined by more degenerate cells at later time points. In contrast, PAAG-treated mice had less severe crypt degeneration, reduced inflammation, and tended to retain healthier villous epithelium. The results of bacterial counts for the MLN demonstrate a dramatic reduction of circulating bacteria in the case of the treated mice. In FIG. 16, the colony forming units (CFU)/g of bacteria in the MLN for all 6 animals in the irradiated and non-irradiated groups is shown. For the irradiated animals, the PAAG treated group had dramatically less bacteria in the MLN than in the vehicle control group.

Figure 19:
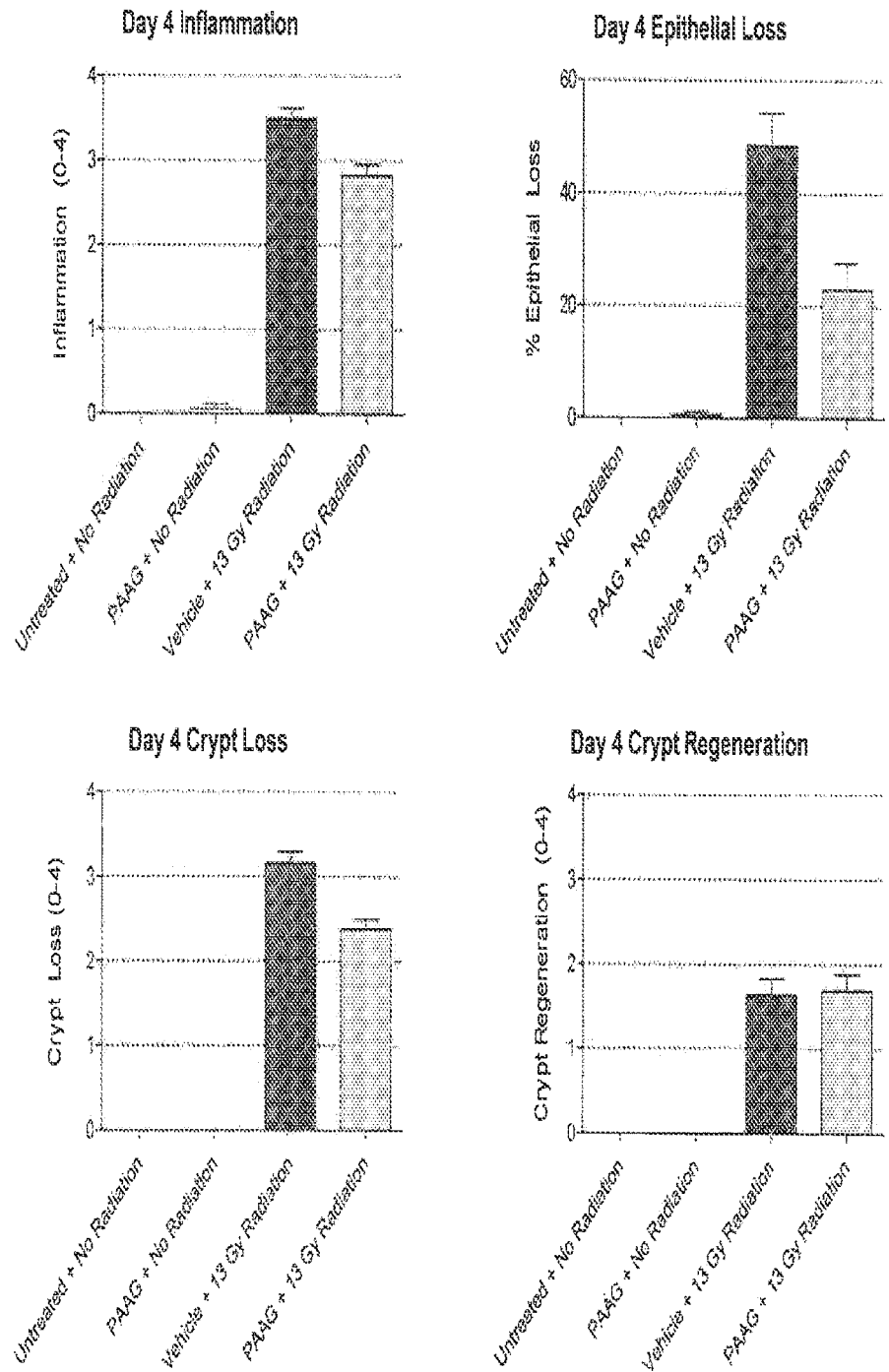
FIG. 19 depicts exemplary inflammation, epithelial loss, crypt loss, and crypt regeneration on day 4.
Figure 20:
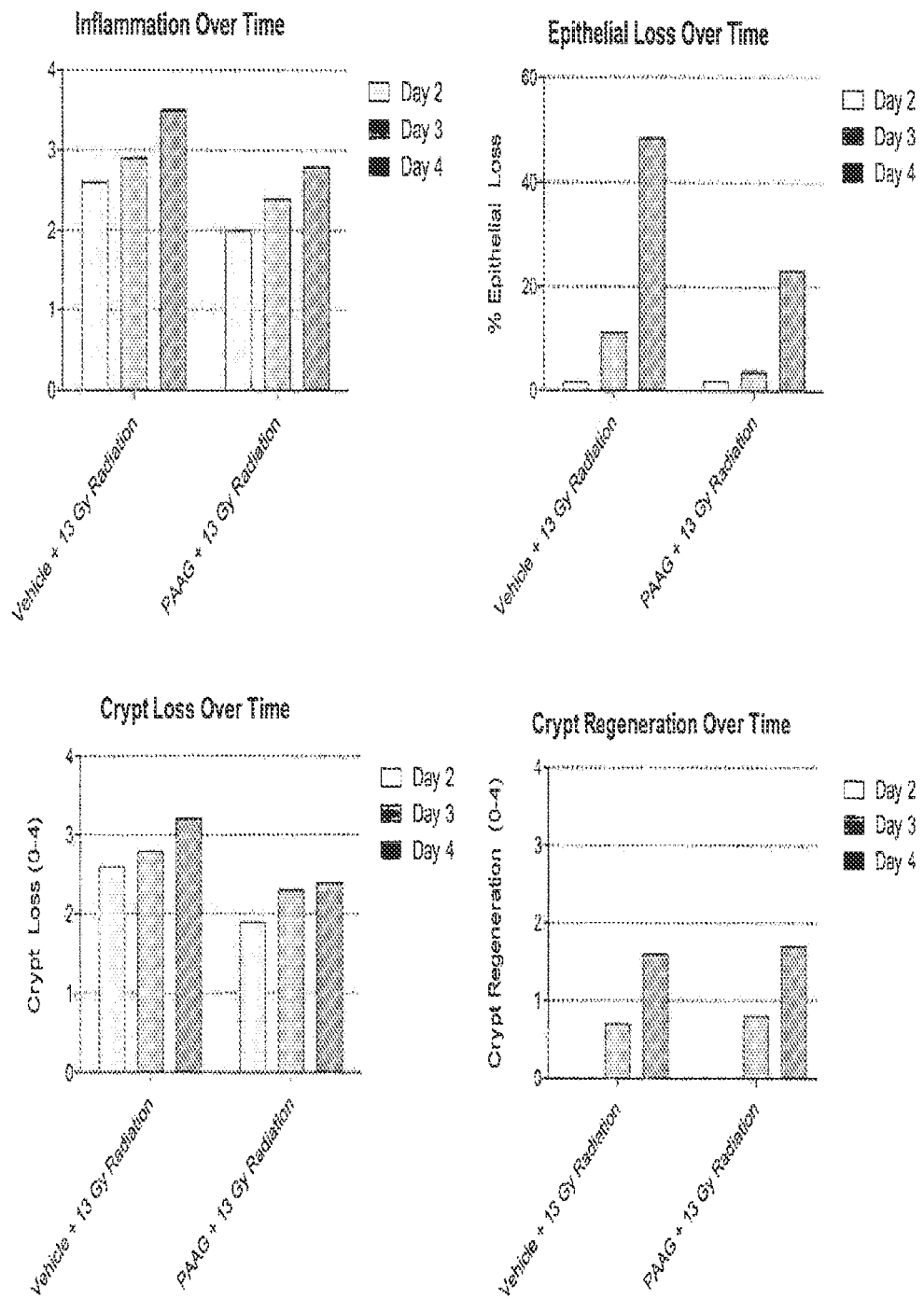
FIG. 20 depicts an exemplary increase in inflammation, epithelial loss, crypt loss, and crypt regeneration over time after radiation exposure.
Figure 21:
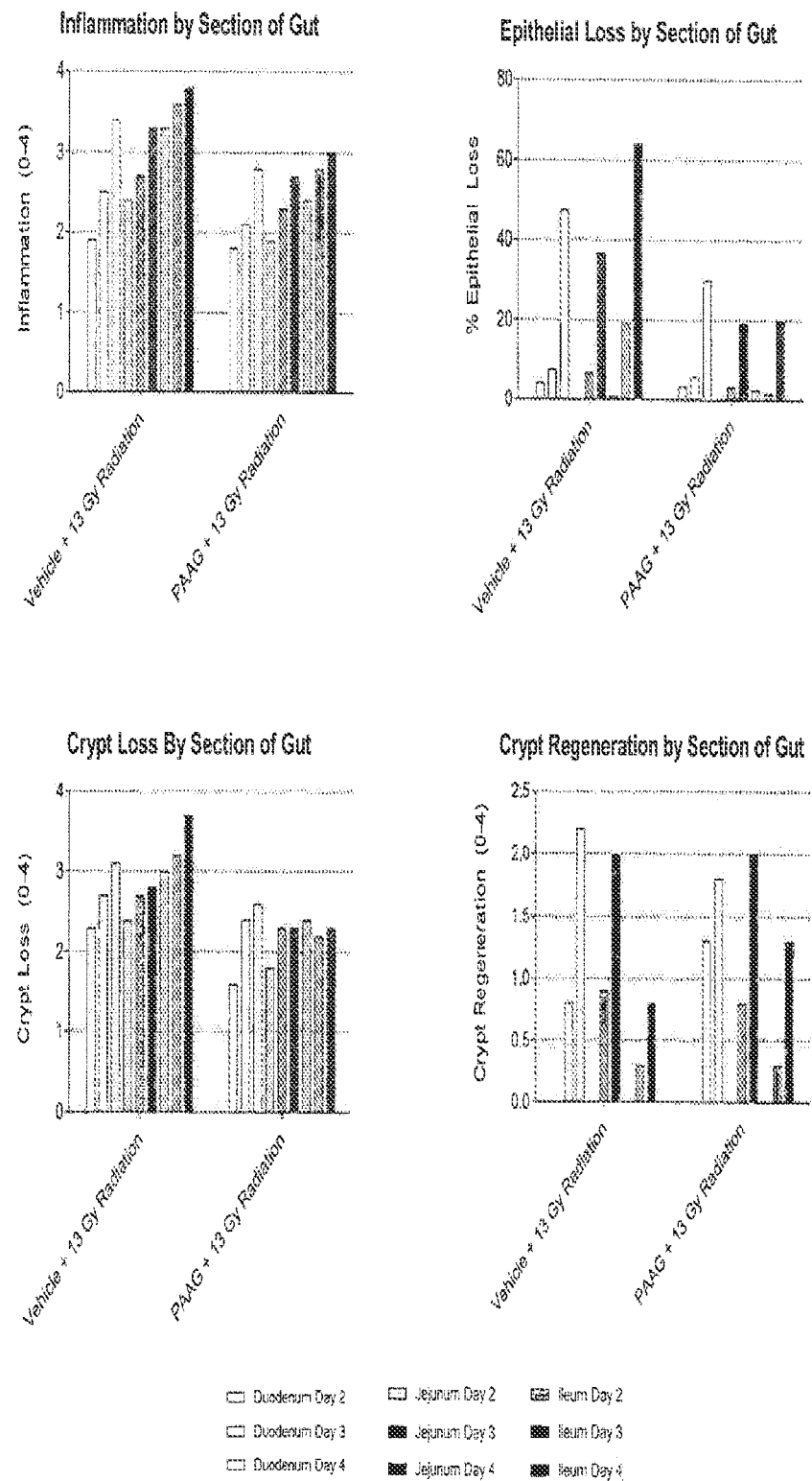
FIG. 21 depicts exemplary inflammation, epithelial loss, crypt loss, and crypt regeneration over time in different sections of gut after radiation exposure.

Quantitative analysis of the histological data at day 4 shows that PAAG reduced GI inflammation, reduced epithelial loss and reduced crypt loss relative to control in mice exposed to lethal ionizing radiation (FIG. 19). These findings support a radio-protective effect of PAAG which previous reports have linked to free radical scavenging (Nishimura et al, 2003) or to mucosal-protective properties (Ersin et al, 2000).

Data from day 4, in both groups and more severe in vehicle-treated animals, suggest susceptibility to bacterial translocation across damaged intestinal mucosa coincident with a loss of villous epithelium. Prior to day 4, crypt damage may be insufficient to cause significant bacterial infection and translocation to deeper tissue layers.

Description and Representative Photomicrographs:
Group 1, No Treatment+No Radiation:
All regions of small intestine were essentially normal.
Group 2, PAAG+No Radiation:
All regions of small intestine were essentially normal.
Group 3, Vehicle-Treatment+13 Gy Radiation:
All regions of the small intestine were affected with similar findings.

At day 2, there was moderate to marked crypt degeneration. Crypt lining cells were apoptotic after radiation injury. Nuclei were pyknotic, cytoplasm was shrunken and condensed, and cells detached from the underlying basement membrane and sloughed into the crypt lumen. Some cells had characteristics more suggestive of necrosis with lysis of cell walls. This tended to be in areas of active inflammation suggesting that inflammatory mediators may have played a role in cell necrosis. Inflammation was mixed with large numbers of neutrophils admixed with macrophages and lymphocytes. Overall, villi retained their normal height and structure and their epithelium was intact.

At day 3, there was progressive crypt degeneration and loss. In some crypts, epithelial cells were apoptotic or necrotic as described above. In other areas, there was simply a loss of crypts and replacement by lymphohistiocytic inflammation. There was mild crypt regeneration characterized by large, intensely basophilic cells with large nuclei and active mitoses. Villi were slightly blunted and villous epithelium was mildly degenerate.

At day 4, there was more severe loss of villous epithelium. The marked crypt loss was as would be expected for animals with chronic inflammation and early fibrosis. As opposed to the neurophils seen at day 2, inflammation was predominantly characterized by histiocytes admixed with lymphocytes. Some crypts were still degenerating (thick arrow in jejunum in FIG. 25), but overall there was simply a loss of normal crypts along the base of villi. Villi were shortened and blunted and the epithelium was vacuolated and degenerate. There was, however, regeneration of some crypts which was especially evident in the jejunum. Regenerating crypts (arrows in FIG. 25) are deeply basophilic, have large cells, and mitoses are often visible. In general, crypts were absent rather than overtly degenerate and the base of villi was lined by a mixed inflammatory cell population and fibroblasts instead of crypts. Crypt regeneration continued multifocally but was mild overall.

Group 4, PAAG-Treatment+13 Gy Radiation:

All regions of the small intestine were affected with similar findings.

At day 2, there was mild to moderate crypt degeneration. Crypt lining cells were apoptotic after radiation injury. Nuclei were pyknotic, cytoplasm was shrunken and condensed, and cells detached from the underlying basement membrane and sloughed into the crypt lumen. Some cells had characteristics more suggestive of necrosis with lysis of cell walls. This tended to be in areas of active inflammation suggesting that inflammatory mediators may have played a role in cell necrosis. Inflammation was mixed with scattered foci of neutrophils admixed with macrophages and lymphocytes. Overall, villi retained their normal height and structure and their epithelium was intact.

At day 3, there was progressive crypt degeneration and loss. In some crypts, epithelial cells were apoptotic or necrotic as described above. In other areas, there was simply a loss of crypts and replacement by lymphohistiocytic inflammation. There was mild to moderate crypt regeneration characterized by large, intensely basophilic cells with large nuclei and active mitoses. Villi were minimally blunted.

As in Group 3 animals, there was an increased loss of villous epithelium at day 4, but this loss was not as severe as in group 3 animals. Crypt loss was moderate to marked and associated with chronic inflammation and early fibrosis. As opposed to the neutrophils seen at day 2, inflammation was predominantly characterized by histiocytes admixed with lymphocytes. There was moderate to marked crypt regeneration, which was more prominent in the jejunum, and in some cases regenerating cells could be seen spreading onto the base of villi. For example, regenerating crypts (arrows in FIG. 27) are deeply basophilic, have large cells, and mitoses are often visible. Villi were shortened and blunted as in Group 3, but the epithelium is less degenerate. Inflammation was more chronic in nature and replaced crypts multifocally.

Figure 22:
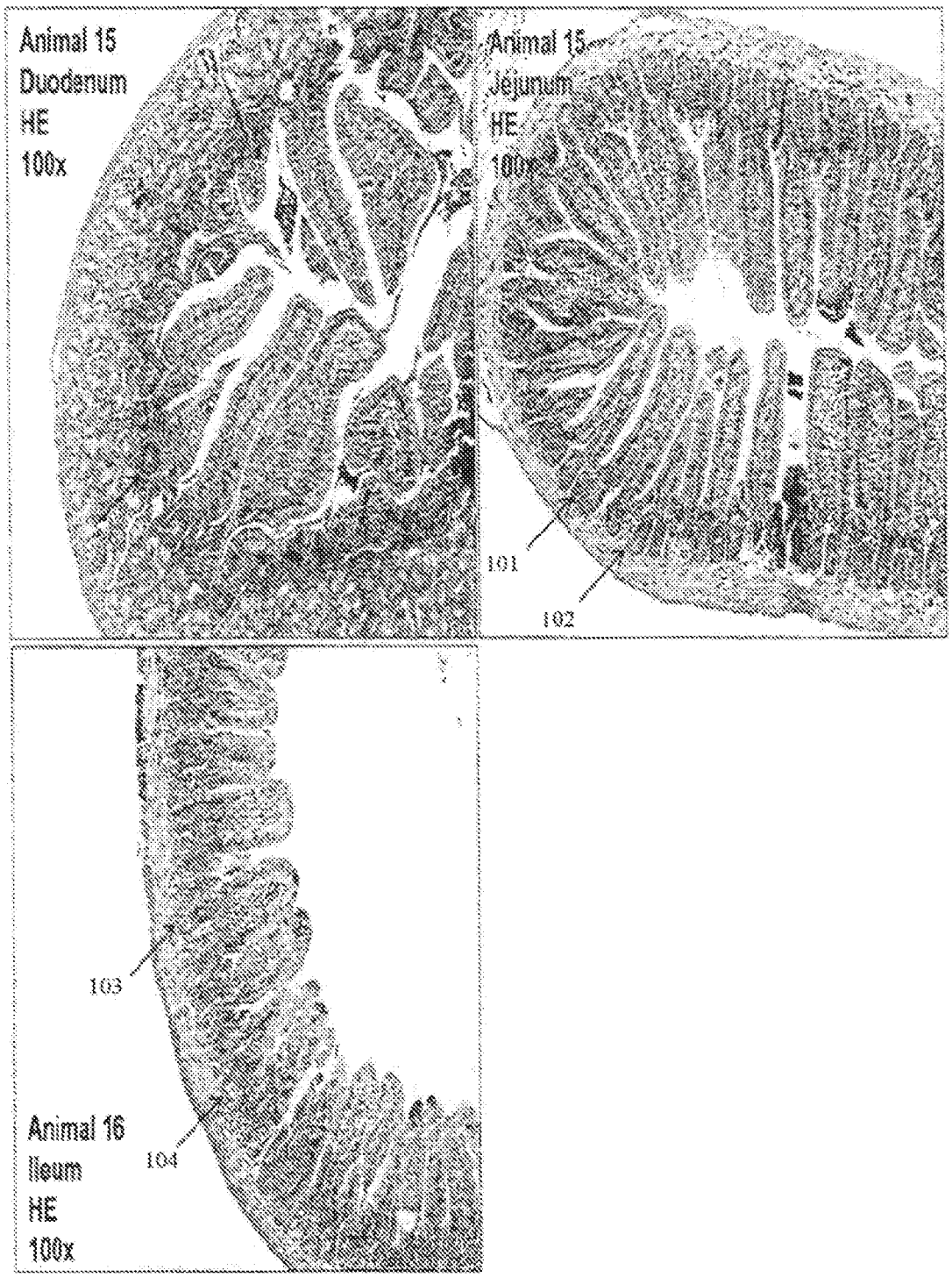
FIG. 22 depicts exemplary photomicrographs of small intestines of animals in Group 1 (untreated+no radiation).
Figure 23:
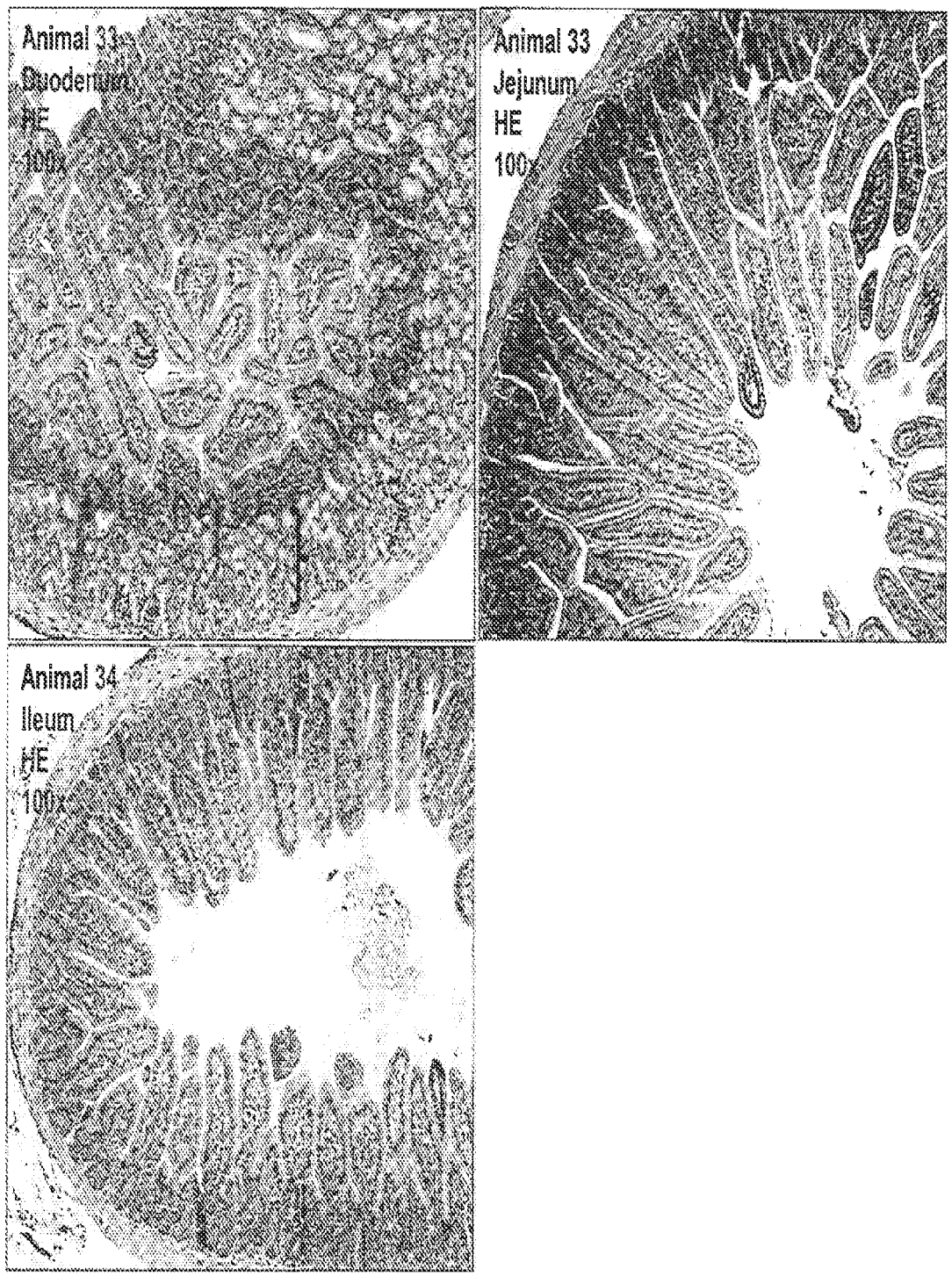
FIG. 23 depicts exemplary photomicrographs of small intestines of animals in Group 2 (PAAG+no radiation).
Figure 24:
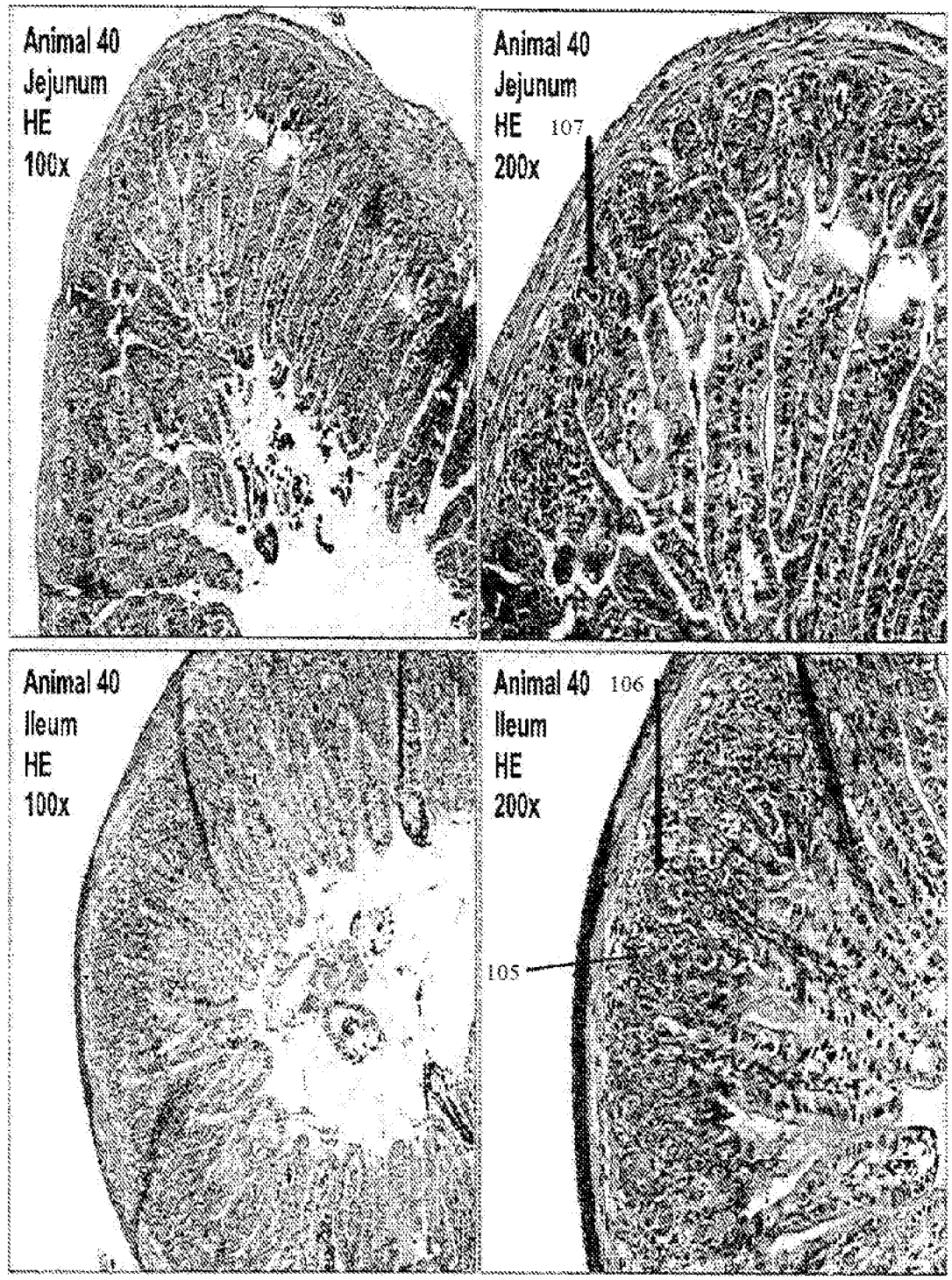
FIG. 24 depicts exemplary photomicrographs at 2 days post-irradiation in group 3 animals (vehicle+13 Gy radiation).
Figure 25:
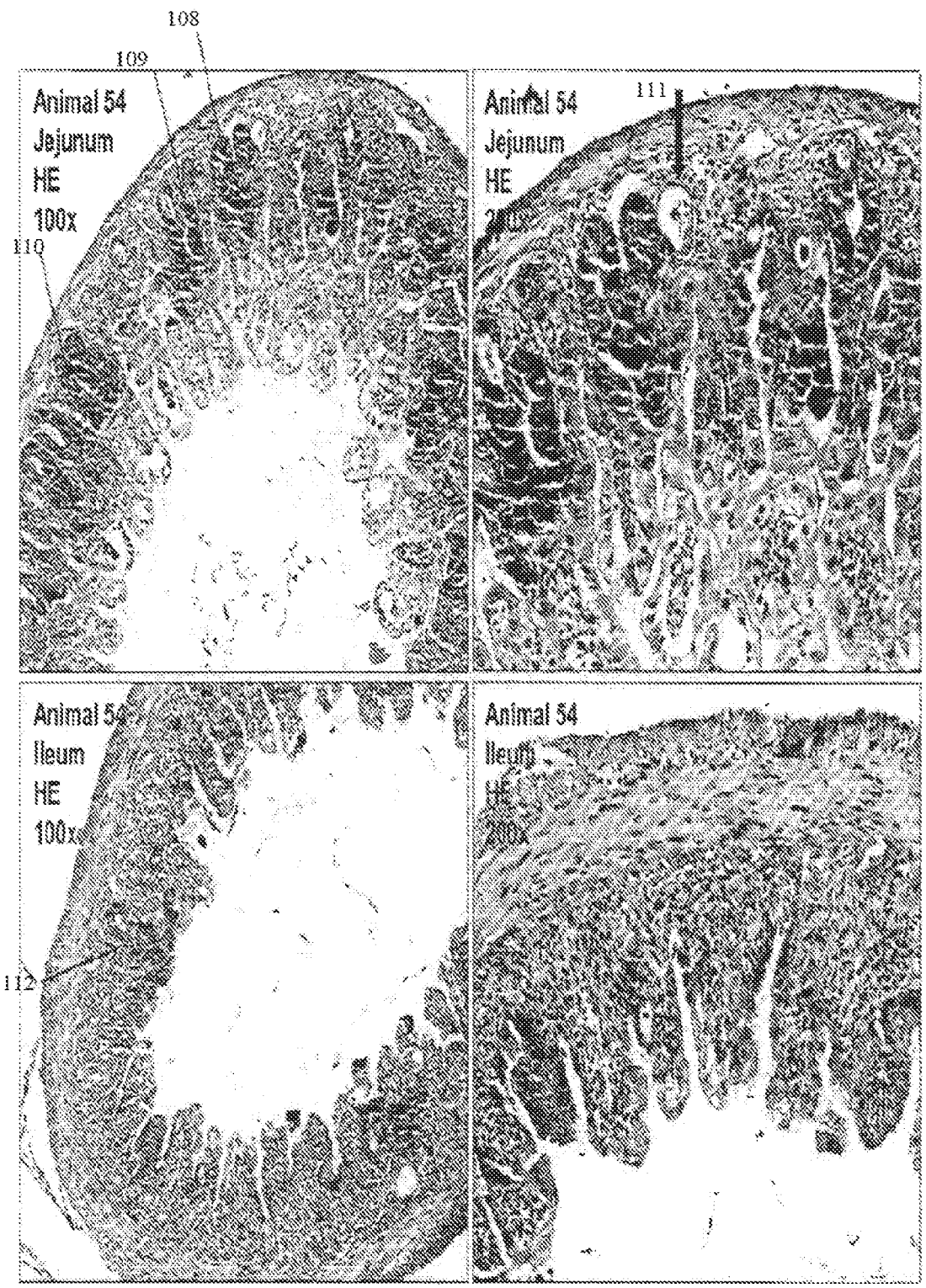
FIG. 25 depicts exemplary photomicrographs at 4 days post-irradiation animals in group 3 (vehicle+13 Gy radiation).
Figure 26:
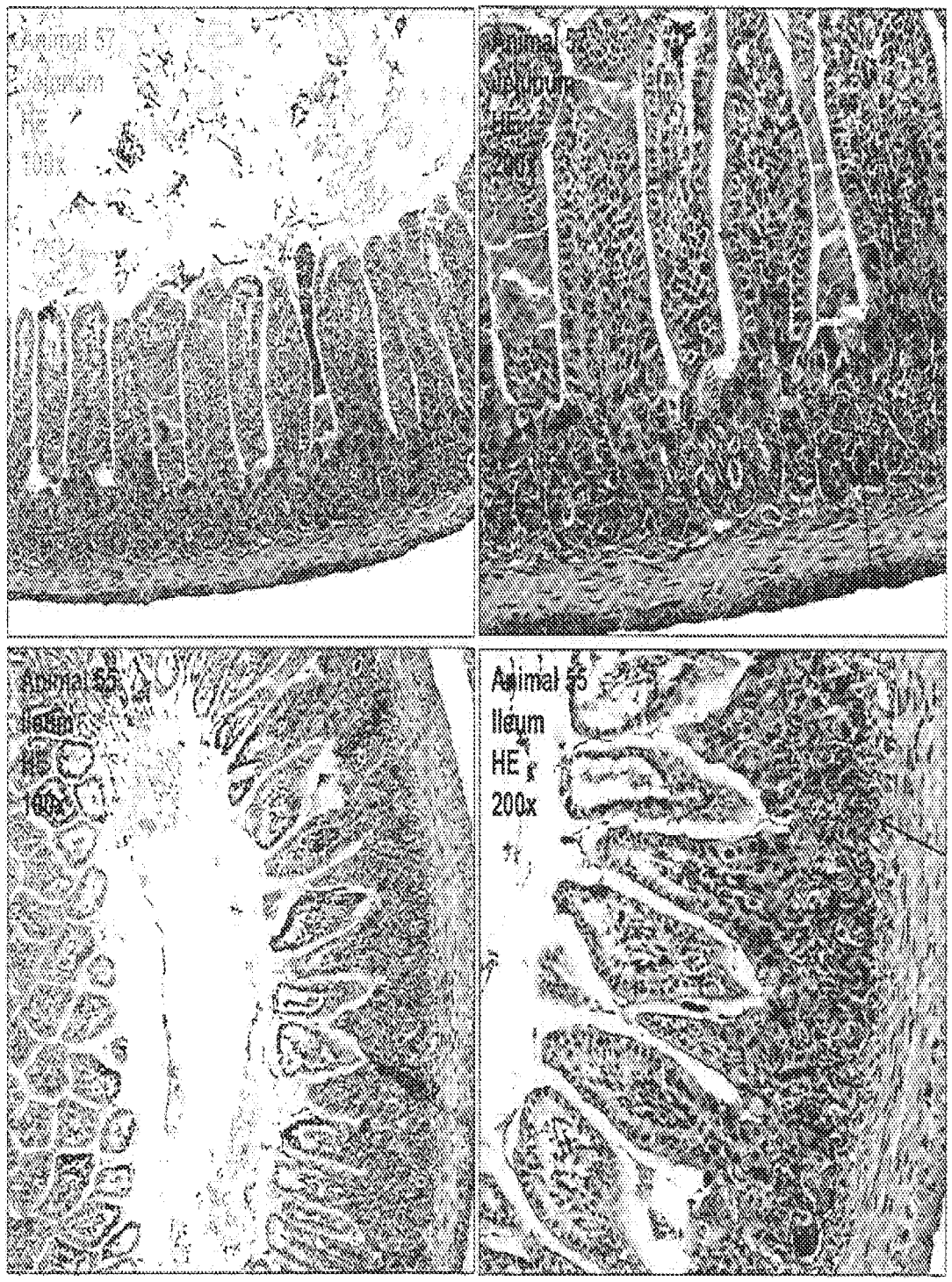
FIG. 26 depicts exemplary photomicrographs at 2 days post-irradiation animals in group 4 (PAAG+13 Gy radiation).
Figure 27:
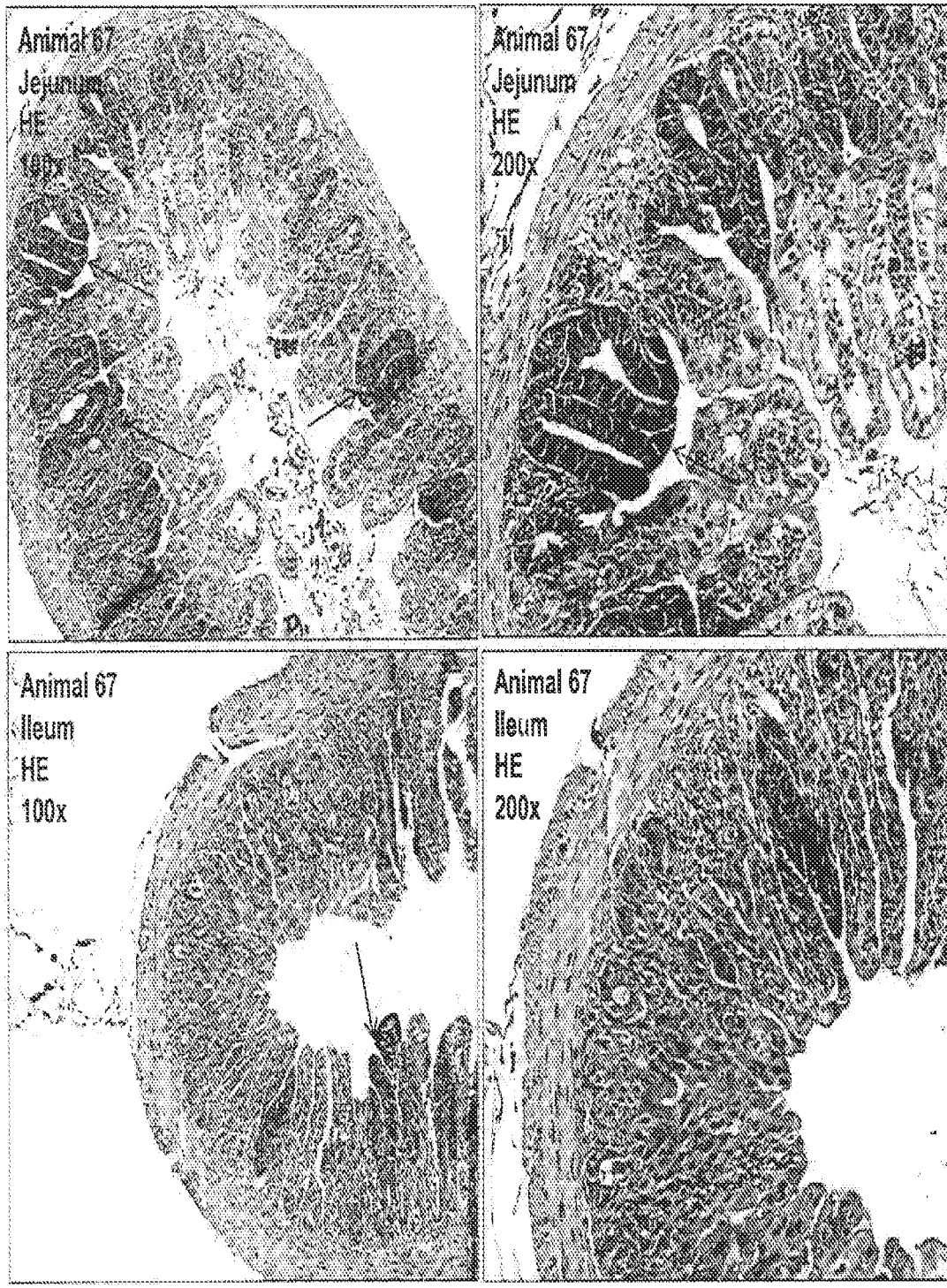
FIG. 27 depicts exemplary photomicrographs at 4 days post-irradiation animals in group 4 (PAAG+13 Gy radiation).

See FIGS. 22-27 for representative photomicrographs. In FIG. 22, arrows labeled 101, 102, 103, and 104 refer to regenerating crypts. In FIG. 24, arrow labeled 105 refers to regenerating crypts, and arrows labeled 106 and 107 refer to degenerating crypts. In FIG. 25, arrows labeled 108, 109, 110, and 112 refer to regenerating crypts, and arrow labeled 111 refers to degenerating crypts.

Summary

PAAG treatment partially protected C57BL/6 mice from the GI effects of total body irradiation. Irradiated, vehicle-treated mice had marked crypt degeneration evident from 2-4 days post-irradiation. Crypt degeneration was associated with inflammation progressing from acute to chronic over the course of the experiments. Villi became progressively shorter and were lined by more denegerate cells at later time points, which would be expected without crypt epithelial cells to replenish villous epithelium. In contrast, PAAG-treated mice had less severe crypt degeneration, reduced inflammation, and tended to retain healthier villous epithelium, suggesting a radio-protective effect of PAAG.

Example 10: Evaluation of Effect of PAAG on Irradiation Biomarkers

Methods

Control or irradiated mice were treated with vehicle or PAAG once a day via oral gavage at day 2, 3, and 4 starting 24 after total body irradiation with 5% long bone protection.

Pro-Calcitonin Levels in Plasma are not Affected by PAAG

Pro-calcitonin (PCT) is a circulating plasma marker that has been used to indicate systemic inflammation and has been used in radiation studies to detect GI inflammation. PCT serum levels have been shown to increase in relation to the magnitude of bacteremia in mice.

Figure 28:
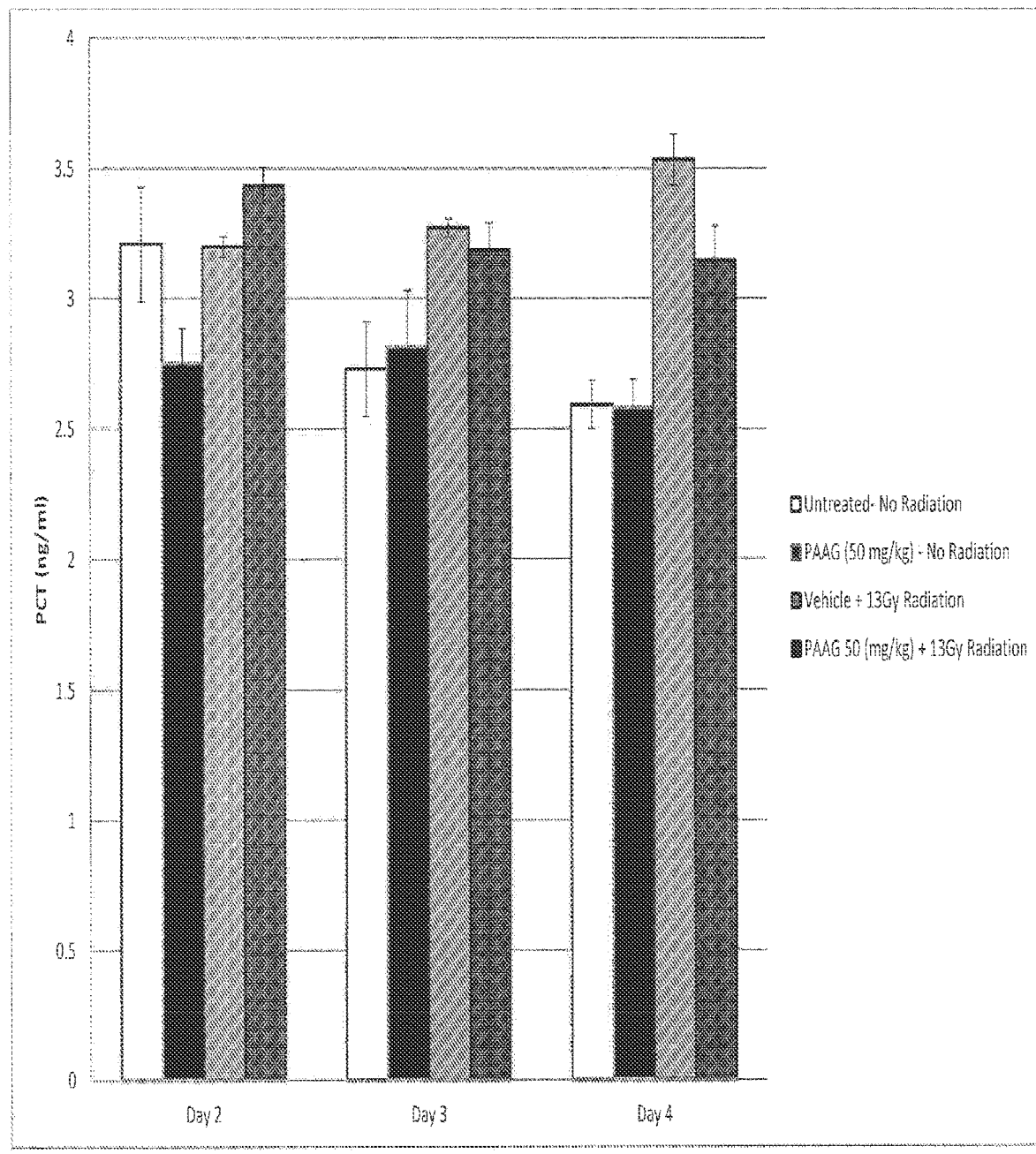
FIG. 28 depicts exemplary Pro-calcitonin (PCT) in plasma for mice treated and untreated with radiation and PAAG.

PAAG reduced circulating plasma levels of PCT relative to controls in mice exposed to a potentially lethal dose of ionizing radiation (13 Gy), as shown on FIG. 28.

Citrulline Levels are Increased in Plasma by Treatment with PAAG

Citrulline is an unnatural amino acid and metabolic end product produced by small bowel enterocytes (cells specific to the GI tract). Levels of citrulline are reduced when enterocytes are damaged or reduced. Citrulline is mainly produced from viable enterocytes of the small bowel and has been used for quantifying radiation-induced epithelial cell loss (Lutgens 2003, Int. J. Rad. Oncol. Biol. Phys. 57 (4), 1067) and as a marker of GI damage. Decreased serum citrulline levels correlate with loss of cell viability or damage to the bowel.

Figure 29:
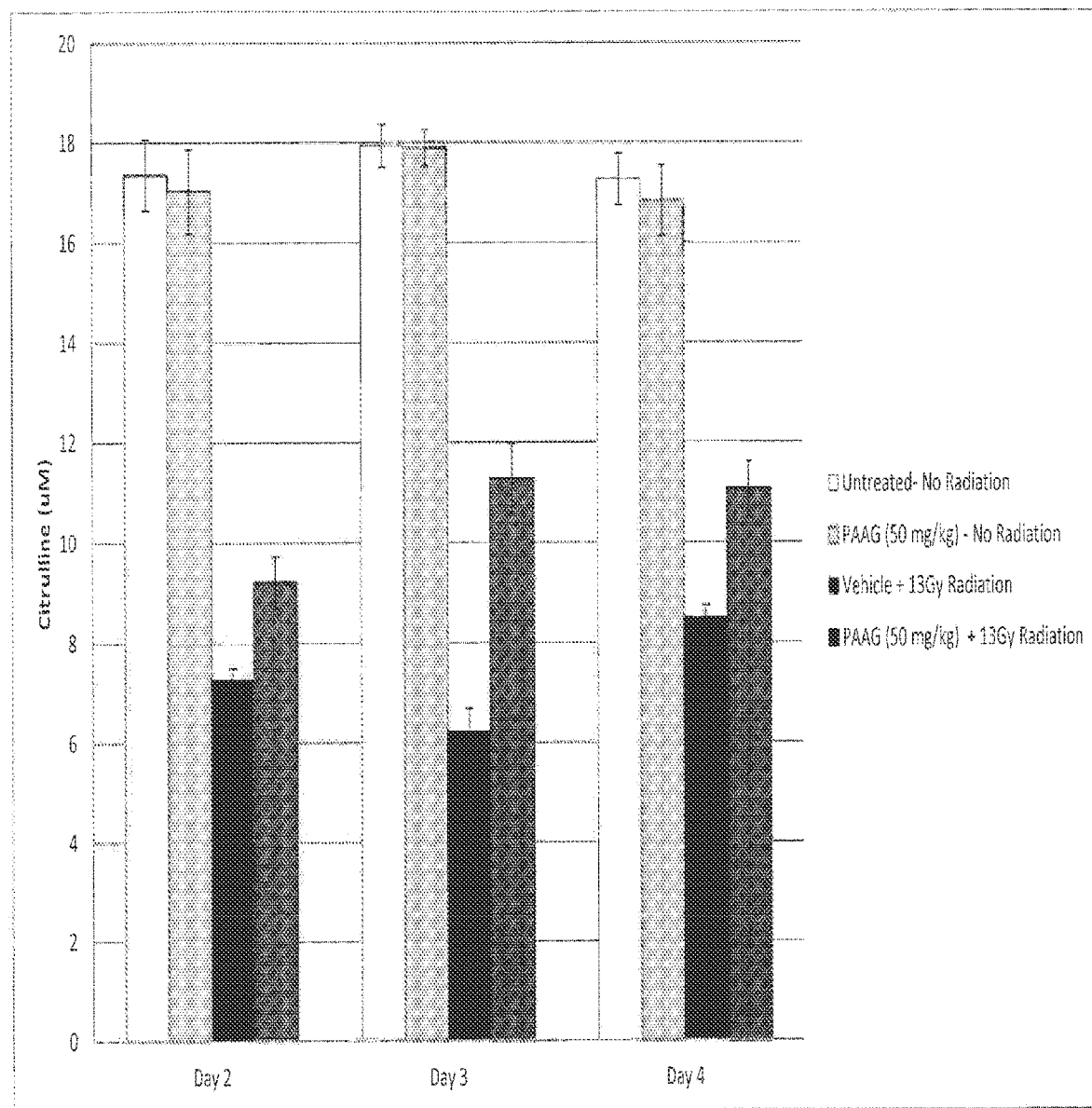
FIG. 29 depicts exemplary citrulline levels in plasma for mice treated and untreated with radiation and PAAG.

PAAG increased circulating amounts of citrulline relative to control on day 3 and 4 in mice relative to control after exposure to lethal ionizing radiation, as shown on FIG. 29. Plasma citrulline was dramatically reduced upon animal exposure to 13 Gy radiation, however, PAAG treated irradiated animals had statistically less citrulline reduction than untreated irradiated animals (P values below), indicating less epithelial cell loss. This result indicates that administration of PAAG reduces damage to enterocytes in the GI tract.

Figure 30:
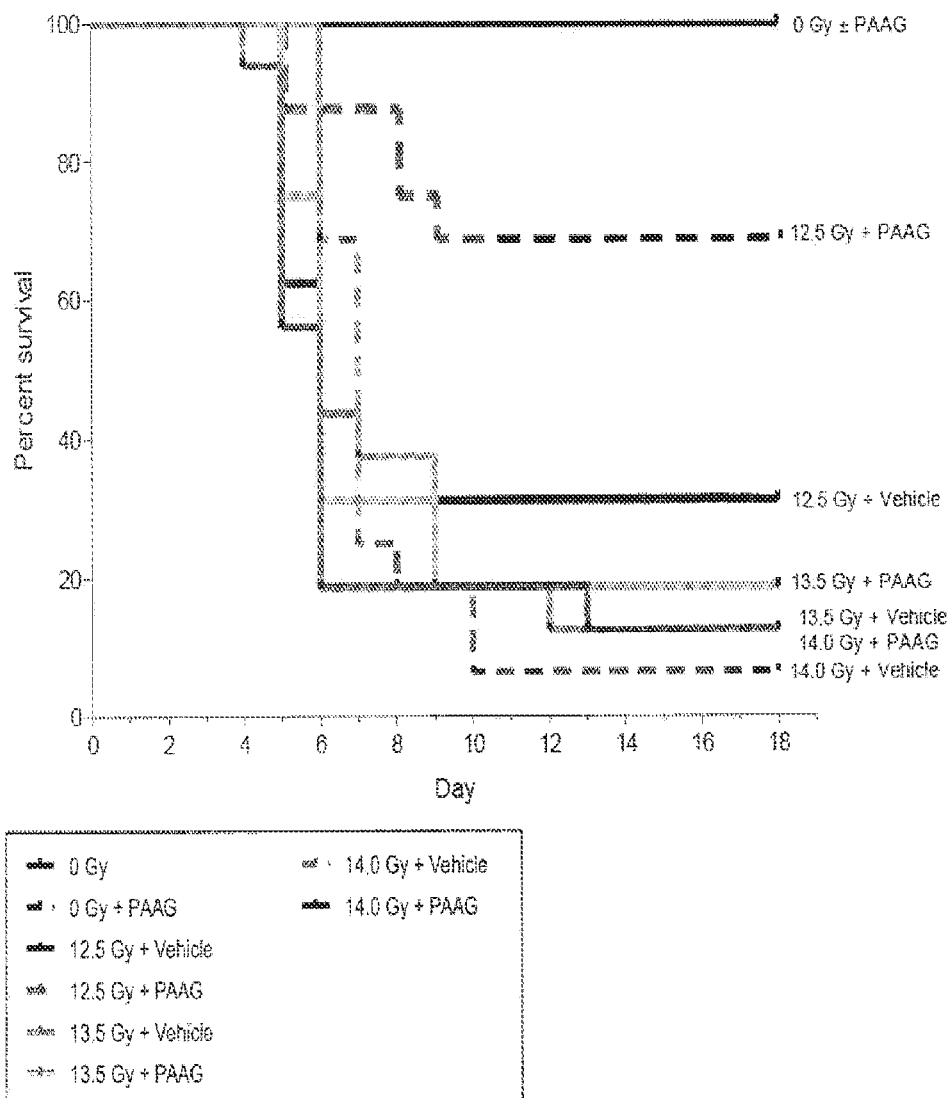
FIG. 30 depicts an exemplary effect of PAAG and radiation treatment on survival.

Example 11: Kaplan-Mayer Survival Plot after Three Doses of Radiation Treated with Vehicle or PAAG Male CB57BL/6 mice of the same weight and age were subjected to radiation doses of 12.5, 13.5 and 14.0 Gy. Animals were given the same dose of PAAG (50 mg/kg once a day) by oral gavage as in the previous study. Eighteen (18) animals were studied in each of 8 arms: irradiated control and active PAAG at each dose. Mortality data is shown in FIG. 30 for three doses of total body radiation treated with vehicle or PAAG given via oral gavage daily. 12.5 Gy dose treated with vehicle or PAAG are numerically significant. 13.5 Gy dose treated with vehicle or PAAG, or 14.0 Gy dosed with vehicle or PAAG are not statistically different.

This study confirms the study shown above in Example 1 suggesting that the activity of PAAG reduced mortality after significant LD70 ionizing radiation. The study also suggests that when the damage is too great, PAAG may not be able to overcome the overwhelming inflammatory response of the GI tract. No adverse effects were observed at any dose.

What is claimed is:

1. A method of treating a subject identified as having been exposed to radiation, trauma, or shock, wherein the radiation, trauma, or shock results in gastrointestinal (GI) damage, the method comprising administering a therapeutically effective amount of a compound to the subject, wherein the compound is a compound of Formula (I):

Formula (I)

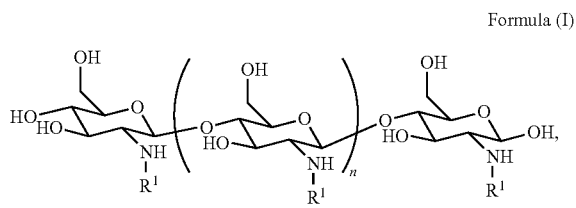

wherein:
n is an integer between 20 and 6000; and
each $R^1$ is independently selected for each occurrence from hydrogen, acetyl,

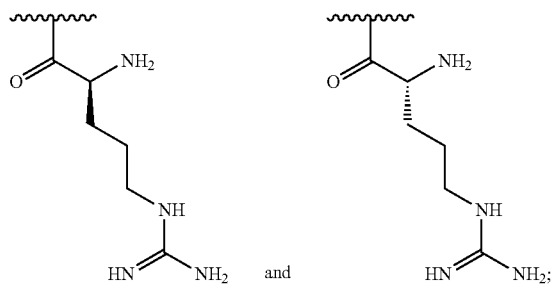 [SMILES: *C(=O)[C@@H](N)CCCNC(=N)N ; "and" ; *C(=O)[C@H](N)CCCNC(=N)N]

wherein at least 25% of $R^1$ substituents are H, at least 1% of $R^1$ substituents are acetyl, and at least 2% of $R^1$ substituents
are

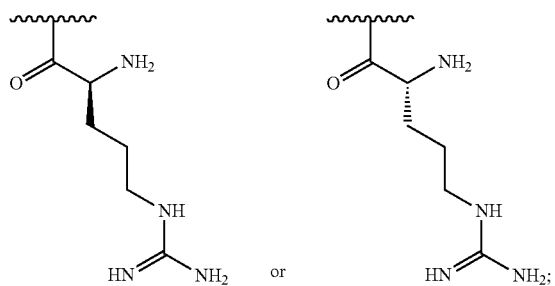 [SMILES: *C(=O)[C@@H](N)CCCNC(=N)N ; "or" ; *C(=O)[C@H](N)CCCNC(=N)N]

wherein upon administration of the compound, the compound treats, reduces the severity, or delays the onset of sepsis or reduces the likelihood of mortality in the subject, thereby treating the subject.

2. The method of claim 1, wherein the subject has a bacterial infection, chemical damage or radiation damage.

3. The method of claim 2, wherein the infection or damage results in leaky gut.

4. The method of claim 1, wherein the method reduces the severity of sepsis or a symptom thereof or decreases the likelihood of mortality from the radiation, trauma or shock relative to a subject not administered with the compound.

5. The method of claim 1, wherein the subject has sepsis or a symptom of sepsis resulting from radiation, trauma or shock.

6. The method of claim 1, wherein the trauma or shock is a bacterial, viral, or fungal infection resulting in GI damage.

7. The method of claim 6, wherein the bacterial infection is from one of the following bacteria: *Salmonella enterica* serovar *Typhimurium, Shigella flexneri, E. Coli,* and *P. aeruginosa.*

8. The method of claim 1, wherein the method reduces inflammation in the subject from the radiation, trauma or shock in the subject.

9. The method of claim 1, wherein the trauma results from exposure to a toxic chemical or poison.

10. The method of claim 1, wherein the trauma results from multi-organ failure from physical damage and trauma to the body, burns, blast injury, systemic infection, blood loss (hypotension), or traumatic brain injury.

11. The method of claim 1, wherein the shock results from excessive stimuli, commensals, injury, heat, autoantigens, tumors, or necrotic cells.

12. The method of claim 1, wherein the subject has necrotizing enterocolitis, necrotic enteritis, short bowel syndrome, or short gut syndrome.

13. The method of claim 1, wherein the compound is administered at regular intervals.

14. The method of claim 1, wherein the subject is treated within 1 hour, 2 hours, 3 hours, 4 hours, 5 hours, 6 hours, 8 hours, 10 hours, 12 hours, 16 hours, 20 hours, 24 hours, 2 days, 3 days, 4 days, 5 days, 6 days, 1 week, or 2 weeks after exposure to radiation, trauma, shock, or infection.

15. The method of claim 1, wherein the compound is functionalized at between 18% and 30%.

16. The method of claim 1, wherein the molecular weight of the compound is from 50 to 150 kDa.

17. The method of claim 1, wherein the polydispersity index of the compound is from 1.0 to 2.5.

18. A method of reducing permeability of the gastrointestinal tract of a subject identified as having been exposed to radiation trauma, or shock, the method comprising administering a therapeutically effective amount of a compound to the subject,
wherein the compound is a compound of Formula (I):

Formula (I)

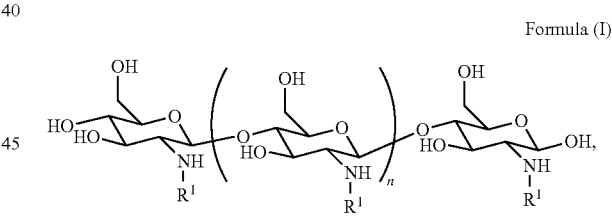

wherein:
n is an integer between 20 and 6000; and
each $R^1$ is independently selected for each occurrence from hydrogen, acetyl,

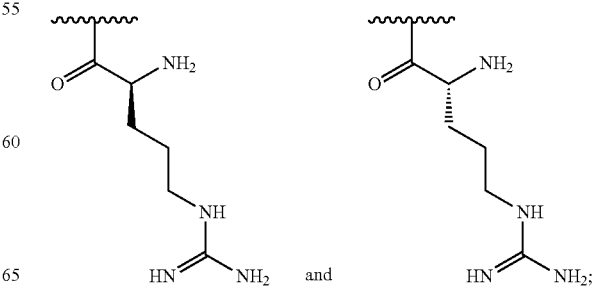

wherein at least 25% of $R^1$ substituents are H, at least 1% of $R^1$ substituents are acetyl, and at least 2% of $R^1$ substituents are
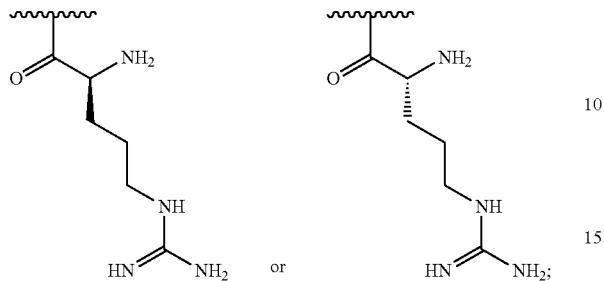
wherein upon administration of the compound, the compound reduces permeability of the gastrointestinal tract of a subject.
19. The method of 18, wherein the permeability is a result of shock, trauma, or exposure to infection in the GI.
* * * * *

UNITED STATES PATENT AND TRADEMARK OFFICE
CERTIFICATE OF CORRECTION

| | |
|---|---|
| PATENT NO. | : 11,975,018 B2 |
| APPLICATION NO. | : 17/150406 |
| DATED | : May 7, 2024 |
| INVENTOR(S) | : Shenda M. Baker et al. |

It is certified that error appears in the above-identified patent and that said Letters Patent is hereby corrected as shown below:

In the Claims

Column 49, Claim 4, Line 60, replace "of mortality from the radiation, trauma or shock" with -- of mortality from the radiation, trauma, or shock --.

Column 49, Claim 5, Line 64, replace "of sepsis resulting from radiation, trauma or" with -- of sepsis resulting from radiation, trauma, or --.

Column 50, Claim 8, Line 6, replace "inflammation in the subject from the radiation, trauma or" with -- inflammation from the radiation, trauma, or --.

Signed and Sealed this
Eleventh Day of June, 2024

Katherine Kelly Vidal
*Director of the United States Patent and Trademark Office*